United States Patent
Patterson et al.

(10) Patent No.: US 10,507,210 B2
(45) Date of Patent: Dec. 17, 2019

(54) KINASE INHIBITOR PRODRUG FOR THE TREATMENT OF CANCER

(71) Applicant: Auckland UniServices Limited, Auckland (NZ)

(72) Inventors: Adam Vorn Patterson, Auckland (NZ); Jeffrey Bruce Smaill, Auckland (NZ); Shevan Silva, Auckland (NZ); Christopher Paul Guise, Auckland (NZ); Matthew Roy Bull, Auckland (NZ); Victoria Jackson, Auckland (NZ); Tillman Pearce, South San Francisco, CA (US); Nipun Davar, South San Francisco, CA (US)

(73) Assignee: Auckland UniServices Limited, Auckland (NZ)

( * ) Notice: Subject to any disclaimer, the term of this patent is extended or adjusted under 35 U.S.C. 154(b) by 0 days.

(21) Appl. No.: 15/531,677

(22) PCT Filed: Dec. 3, 2015

(86) PCT No.: PCT/US2015/063806
§ 371 (c)(1),
(2) Date: May 30, 2017

(87) PCT Pub. No.: WO2016/090174
PCT Pub. Date: Jun. 9, 2016

(65) Prior Publication Data
US 2017/0360790 A1  Dec. 21, 2017

Related U.S. Application Data

(60) Provisional application No. 62/187,750, filed on Jul. 1, 2015, provisional application No. 62/167,849, filed on May 28, 2015, provisional application No. 62/150,729, filed on Apr. 21, 2015, provisional application No. 62/087,212, filed on Dec. 3, 2014.

(51) Int. Cl.

| | | |
|---|---|---|
| *A61K 31/519* | (2006.01) | |
| *A61K 31/724* | (2006.01) | |
| *A61K 9/00* | (2006.01) | |
| *A61K 31/517* | (2006.01) | |
| *A61K 45/06* | (2006.01) | |
| *A61K 47/40* | (2006.01) | |

(52) U.S. Cl.
CPC .......... *A61K 31/519* (2013.01); *A61K 9/0019* (2013.01); *A61K 31/517* (2013.01); *A61K 31/724* (2013.01); *A61K 45/06* (2013.01); *A61K 47/40* (2013.01)

(58) Field of Classification Search
CPC .................................................. A61K 31/519
USPC .................................................. 514/264.11
See application file for complete search history.

(56) References Cited

U.S. PATENT DOCUMENTS

| | | | |
|---|---|---|---|
| 5,202,231 A | 4/1993 | Drmanac et al. | |
| 5,445,934 A | 8/1995 | Fodor et al. | |
| 5,525,464 A | 6/1996 | Drmanac et al. | |
| 5,695,940 A | 12/1997 | Drmanac et al. | |
| 5,744,305 A | 4/1998 | Fodor et al. | |
| 5,795,716 A | 8/1998 | Chee et al. | |
| 5,800,992 A | 9/1998 | Fodor et al. | |
| 7,799,782 B2 * | 9/2010 | Munson | C07D 231/56 514/234.5 |
| 8,188,102 B2 * | 5/2012 | Lee | C07D 401/12 514/266.2 |
| 8,404,839 B2 * | 3/2013 | Dobson | A61K 31/517 544/293 |
| 9,073,916 B2 | 7/2015 | Smaill et al. | |
| 9,101,632 B2 | 8/2015 | Smaill et al. | |
| 2012/0202832 A1 * | 8/2012 | Smaill | A61K 31/519 514/264.11 |
| 2013/0053409 A1 * | 2/2013 | Butterworth | C07D 401/02 514/272 |
| 2013/0288240 A1 * | 10/2013 | Rimkunas | C07K 16/40 435/6.11 |
| 2014/0141000 A1 * | 5/2014 | Chiu | A61K 31/517 424/136.1 |

FOREIGN PATENT DOCUMENTS

| | | | |
|---|---|---|---|
| EP | 0717113 A2 | 6/1996 | |
| EP | 0730663 A1 | 9/1996 | |
| EP | 2983591 A1 | 2/2016 | |
| JP | 2014-513706 A | 6/2014 | |
| JP | 2014-177456 A | 9/2014 | |
| WO | WO 1995011995 A1 | 5/1995 | |
| WO | WO 1997029212 A1 | 8/1997 | |
| WO | WO 2010104406 A1 | 9/2010 | |
| WO | WO 2010104406 A8 | 9/2010 | |
| WO | WO2011/028135 | * 3/2011 | |
| WO | WO 2012/156437 A1 | 11/2012 | |
| WO | WO 2014/140989 A2 | 9/2014 | |

(Continued)

OTHER PUBLICATIONS

Yokoo et al., PLOS ONE, 2015, 10(11):1-20.*
Hickinson et al. Clin Cancer Res, 2010, 16(4): 1159-69(abstract).*
Ch et al., Invest New Drugs, 2013, 31(3): 516-24 (abstract).*
Bose et al., Expert Opin Investig Drugs, 2009, 18(11): 1735-51 (abstract).*
Song et al., Zhongguo Fei Ai Za Zhi, 2013, 16(3): 138-43 (abstract).*
Johnston et al., Drugs Today (Barc), 2006, 42(7): 441-53 (abstract).*
Ramalingam et al., J Clin Oncol, 2012, 30(27): 3337-44 (abstract).*
Kato et al., Molecular Cancer Therapeutics, 2013, 12(11), Supplement (abstract).*
Yokoo et al. publication, PLOS ONE, 2015, 10(11):1-20.*
Abravaya et al., "Detection of point mutations with a modified ligase chain reaction (Gap-LCR)", Nucleic Acids Research, 23(4):675-682 (1995).

(Continued)

*Primary Examiner* — Rei Tsang Shiao
(74) *Attorney, Agent, or Firm* — Cooley LLP; J. Dean Farmer; Daniel A. Wespe

(57) ABSTRACT

Compositions containing and methods of administering TH-4000 are useful in treatment of cancer alone or in combination with other anti-cancer agents.

24 Claims, 28 Drawing Sheets

(56) References Cited

FOREIGN PATENT DOCUMENTS

WO     WO 2014169035 A1     10/2014

OTHER PUBLICATIONS

Bai et al., "Detection and Clinical Significance of Intratumoral EGFR Mutational Heterogeneity in Chinese Patients with Advanced Non-Small Cell Lung Cancer", Plos ONE, 8(2):e54170 (2013).
Barany, "Genetic disease detection and DNA amplification using cloned thermostable ligase", Proc. Natl. Acad. Sci. USA, 88(1):189-93 (1991).
Berge et al., "Pharmaceutical Salts", Journal of PhaEP_rmaceutical Sciences, 66(1):1-19 (1977).
Brewster et al., "Cyclodextrins as pharmaceutical solubilizers", Adv Drug Deliv Rev., 59(7):645-666 (2007).
Calvo et al., "Assessment of erlotinib pharmacodynamics in tumors and skin of patients with head and neck cancer", Annals of Oncology, 18(4):761-767 (2007).
ClinicalTrials.gov, NCT01631279, published Oct. 15, 2013, (online), [retrieved from internet on Feb. 23, 2016] <URL:http://clinicaltrials.gov/archive/NCT01631279/2013 _ 10_ 15>.
Cotton et al., "Reactivity of cytosine and thymine in single-base-pair mismatches with hydroxylamine and osmium tetroxide and its application to the study of mutations", Proc. Natl. Acad. Sci. USA, 85(12):4397-4401 (1988).
Cross et al., "AZD9291, an Irreversible EGFR TKI, Overcomes T790M-Mediated Resistance to EGFR Inhibitors in Lung Cancer", Cancer Discovery, 4(9):1046-1061 (2014).
Di Lorenzo et al., "Expression of Epidermal Growth Factor Receptor Correlates with Disease Relapse and Progression to Androgen-independence in Human Prostate Cancer", Clinical Cancer Research, 8:3438-3444 (2002).
European Patent Office, Supplementary European Search Report for European Application No. 15865257.8, (dated Jun. 18, 2018).
Faham et al., "A novel in Vivo Method to Detect DNA Sequence Variation", Genome Research, 5(5):474-482 (1995).
Felip et al., "A Phase Ii Pharmacodynamic Study of Erlotinib in Patients with Advanced Non-Small Cell Lung Cancer Previously Treated with Platinum-Based Chemotherapy", Clinical Cancer Research, 14(12):3867-3874 (2008).
Fischer et al., "DNA fragments differing by single base-pair substitutions are separated in denaturing gradient gels: Correspondence with melting theory", Proc. Natl. Acad. Sci. USA, 80(6):1579-1583 (1983).
Franovic et al., "Translational up-regulation of the EGFR by tumor hypoxia provides a nonmutational explanation for its overexpression in human cancer", PNAS, 104(32):13092-13097.
Hamilton et al., "Effects of Smoking on the Pharmacokinetics of Erlotinib", Clinical Cancer Research, 12(7):2166-2171 (2006).
Hynes et al., "ERBB Receptors and Cancer: The Complexity of Targeted Inhibitors", Nature Reviews Cancer, 5(5):341-354 (2005).
International Search Report and Written Opinion of Corresponding PCT Application No. PCT/US2015/063806 (Publication No. WO 2016/090174 A1) dated Mar. 3, 2016 (15 pages).
Iyer et al., "The Transcriptional Program in the Response of Human Fibroblasts to Serum", 283(5398):83-87 (1999).
Johnston, "Gene chips: Array of hope for understanding gene regulation", Current Biology, 8(5):R171-R174 (1998).
Kan et al., "Antenatal diagnosis of sickle-cell anxmia by DNA analysis of amniotic-fluid cells", The Lancet, 312(8096):910-912 (1978).
Kubota et al., "2-Hydroxypropyl-β-Cyclodextrin Acts as a Novel Anticancer Agent", Haematologica, The Hematology Journal: Official Organ of the European Hematology Association, Fondazione Ferrata Storti, IT, 99(Suppl.1):593-594, Abstract (2014).
Landegren et al., "A Ligase-Mediated Gene Detection Technique", Science, 241(4869):1077-1080 (1988).
Luo et al., "Correlation of pharmacokinetics with the antitumor activity of Cetuximab in nude mice bearing the GEO human colon carcinoma xenograft", Cancer Chemother Pharmacol, 56(5):455-464 (2005).
Maskos et al., "A novel method for the parallel analysis of multiple mutations in multiple samples", Nucleic Acids Research, 21(9):2269-2270 (1993).
Maurice Wilkins Centre for Molecular Biodiscovery, "Local cancer drug approved for first clinical trial in United States and New Zealand", online news article, A Centre of Research Excellence hosted by the University of Auckland (Aug. 30, 2012), <URL:http://www.mauricewilkinscentre.org/news/local-cancer-drug-approved-for-first-clinical-trial-in-united-states-and-new-zealand.aspx>.
Minakata et al., "Hypoxia induces gefitinib resistance in non-small-cell lung cancer with both mutant and wild-type epidermal growth factor receptors", Cancer Science, 103(11):1946-1954 (2012).
Murakami et al., "Hypoxia Increases Gefitinib-Resistant Lung Cancer Stem Cells through the Activation of Insulin-Like Growth Factor 1 Receptor", Plos ONE, 9(1):e86459 (2014).
Myers et al., "Detection of Single Base Substitutions by Ribonuclease Cleavage at Mismatches in RNA:DNA Duplexes", Science, 230(4731):1242-1246 (1985).
Newton et al., "Analysis of any point mutation in DNA. The amplification refractory mutation system (ARMS)", Nucleic Acids Research, 17(7):2503-2516 (1989).
Nikiforov et al., "Genetic Bit Analysis: a solid phase method for typing single nucleotide polymorphisms", Nucleic Acids Research, 22(20):4167-4175 (1994).
Orita et al., "Rapid and Sensitive Detection of Point Mutations and DNA Polymorphisms Using the Polymerase Chain Reaction", Genomics, 5(4):874-879 (1989).
Orum et al., "Single base pair mutation analysis by PNA directed PCR clamping", Nucleic Acids Research, 21(23):5332-5336 (1993).
Patterson et al., "PR610: A novel hypoxia selective tyrosine kinase inhibitor in phase 1 clinical trial", Molecular Cancer Therapeutics, 12(Suppl 1), Abstract: B278 (2013).
Patterson et al., "TH-4000, a hypoxia-activated EGFR/Her2 inhibitor to treat EGFR-TKI resistant T790M-negative NSCLC", Journal of Clinical Oncology, 33(Suppl 15), Abstract:e13548 (2015).
Posadas et al., "A Prospective Analysis of Imatinib-induced c-KIT Modulation in Ovarian Cancer: A Phase II Clinical Study With Proteomic Profiling", Cancer, 110(2):309-317 (2007).
Saiki et al., "Genetic analysis of amplified DNA with immobilized sequence-specific oligonucleotide probes", Proc. Natl. Acad. Sci. USA, 86(16):6230-6234 (1989).
Sharma et al., ""Oncogenic Shock": Explaining Oncogene Addiction through Differential Signal Attenuation", Clin Cancer Res., 12(14 Pt 2):43925-43955 (2006).
Sharma et al., "Epidermal growth factor receptor mutations in lung cancer", Nat Rev Cancer, 7(3):169-181 (2007).
Sharma et al., "Oncogene addiction: setting the stage for molecularly targeted cancer therapy", Genes Dev., 21(24):3214-3231 (2007).
Simon et al., "Accelerated Titration Designs for Phase I Clinical Trials in Oncology", J Natl Cancer Inst., 89(15):1138-1147 (1997).
Smith et al., "Modulation of erlotinib pharmacokinetics in mice by a novel cytochrome P450 3A4 inhibitor, BAS 100", British Journal of Cancer, 98(10):1630-1632 (2008).
Soh J, et al., "Oncogene Mutations, Copy Number Gains and Mutant Allele Specific Imbalance (MASI) Frequently Occur Together in Tumor Cells", PLoS One, 4(10):e7464 (2009).
Syvanen et al., "A Primer-Guided Nucleotide Incorporation Assay in the Genotyping of Apolipoprotein E", Genomics, 8(4):684-692 (1990).
Takezawa et al., "HER2 Amplification: A Potential Mechanism of Acquired Resistance to EGFR Inhibition in EGFR-Mutant Lung Cancers That Lack the Second-Site EGFR T790M Mutation", Cancer Discov., 2(10):922-933 (2012).
Taniguchi et al., "Intratumor heterogeneity of epidermal growth factor receptor mutations in lung cancer and its correlation to the response to gefitinib", Cancer Sci., 99(5):929-935 (2008).
The University of Auckland, "Local cancer drug approved for first clinical trial in United States and New Zealand", online news article (Aug. 30, 2012), <URL:https://www.auckland.ac.nz/en/about/news-

(56) References Cited

OTHER PUBLICATIONS events-and-notices/news/news-2012/2012/08/30/Local-cancer-drug-approved-for-first-clinical-trial-in-United-States-and-New-Zealand.html>.
The University of Auckland, "Local cancer drug approved for first clinical trial in United States and New Zealand", online news article (Aug. 30, 2012), <URL:https://www.fmhs.auckland.ac.nz/en/faculty/about/news-and-events/news/2012/08/30/local-cancer-drug.html>.
Thiede et al., "Simple and sensitive detection of mutations in the ras proto-oncogenes using PNA-mediated PCR clamping" Nucleic Acids Res., 24(5):983-984 (1996).
Threshold Pharmaceuticals, "Threshold Pharmaceuticals and ATOMIC Initiate First Phase 2 Clinical Trial of Tarloxotinib Bromide* (TH-4000) in Patients With Advanced EGFR-Mutant, T790M-Negative Non-Small Cell Lung Cancer" online (Aug. 11, 2015). (online) <http://files.shareholder.com/downloads/THLD/0x0x845469/7E0ECE76-5FA3-43EB-8055-F97735E49A5A/THLD_News_2015_8_11_General.pdf>.
Wagner et al., "Mutation detection using immobilized mismatch binding protein (MutS)", Nucleic Acids Res., 23(19):3944-3948 (1995).
Wallace et al., "Hybridization of synthetic oligodeoxyribonucleotides to Φχ 174 DNA: the effect of single base pair mismatch", Nucleic Acids Research, 6(11):3543-3557 (1979).
Wang et al., "HIF-2alpha-mediated activation of the epidermal growth factor receptor potentiates head and neck cancer cell migration in response to hypoxia", Carcinogenesis, 31(7):1202-1210 (2010).
Wang et al., "Regulation of endocytosis via the oxygen-sensing pathway", Nat Med., 15(3):319-324 (2009).
Wind et al., "Pharmacokinetics of Afatinib, a Selective Irreversible ErbB Family Blocker, in Patients with Advanced Solid Tumours", Clin Pharmacokinet, 52(12):1101-1109 (2013).
Wouters et al., "The Intriguing Interplay Between Therapies Targeting the Epidermal Growth Factor Receptor, the Hypoxic Microenvironment and Hypoxia-inducible Factors", Curr Pharm Des., 19(5):907-917 (2013).
Youil et al., "Screening for mutations by enzyme mismatch cleavage with T4 endonuclease VII", Proc Natl Acad Sci USA, 92(1):87-91 (1995).
Yun et al., "The T790M mutation in EGFR kinase causes drug resistance by increasing the affinity for ATP", Proc Natl Acad Sci USA, 105(6):2070-2075 (2008).
Lin et al., "EGFR-TKI resistance in NSCLC patients: mechanisms and strategies," Am J Cancer Res. 4(5): 411-435 (2014).
Fukazawa, A. et al. (2013) "Management of Skin Toxicity Associated with EGFR-targeted Monoclonal Antibody Treatment for Advanced Colorectal Cancer: A Single Center Experience" *Journal of Japanese College of Surgeons*, 38(2):279-285 (Japanese; English Abstract on p. 285).
Janjigian, Y.Y. et al. (2014) "Dual Inhibition of EGFR with Afatinib and Cetuximab in Kinase Inhibitor-Resistant *EGFR*-Mutant Lung Cancer with and without T790M Mutations" *Cancer Disc*, 4:1036-1045. NIH Public Access Author Manuscript; available in PMC Oct. 1, 2014, 11 printed pages.
Song et al. (2008) "Evaluation of 2-Hydroxypropyl-beta-Cyclodextrin as Solubilizing/Stabilizing Agent for Hydroxycamtothecin" *China Pharmacy*, 4:269-272 (Chinese; English Abstract).

\* cited by examiner

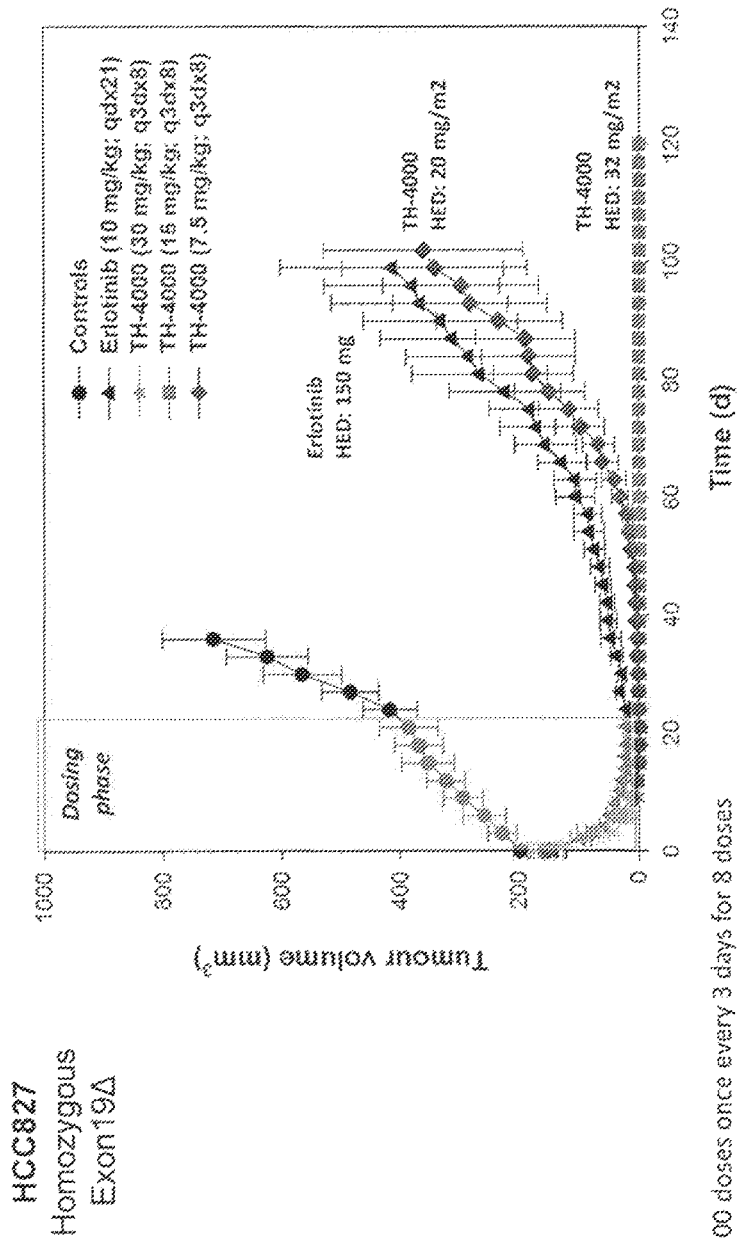

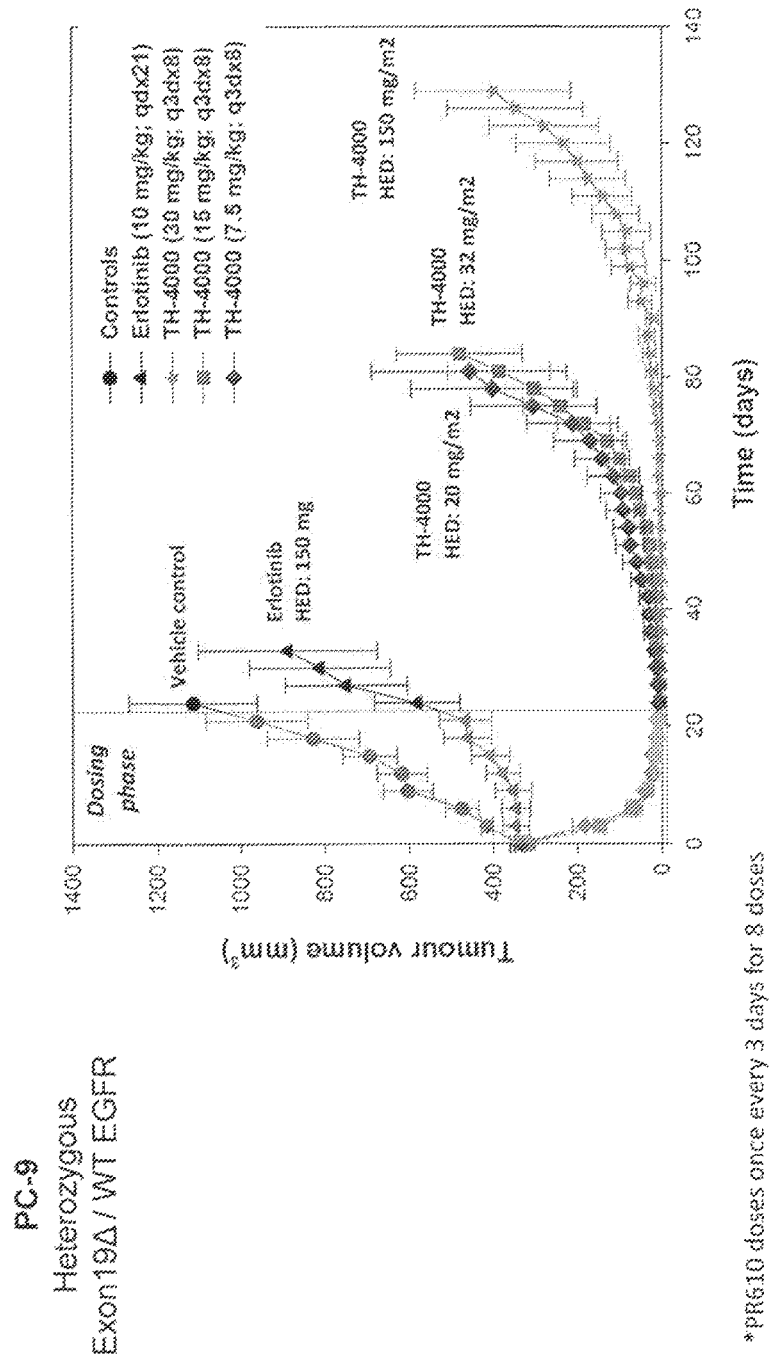

FIG 3. Hypoxin – Plasma vs Tumor PK
- Single administration of Hypoxin at 15 mg/kg [human PK equivalent = 32 mg/m$^2$]
  - Hypoxin clears rapidly from mouse plasma (T½ = 22 minutes)
  - Hypoxin has long residency in PC-9 xenograft (T½β = 39 hours)
  - Hypoxin-TKI has short half life in plasma (1.3 hours) but not tumor (84 hours)
  - Hypoxin-TKI tumor concentration remains above in vitro IC50 value for over 7 days
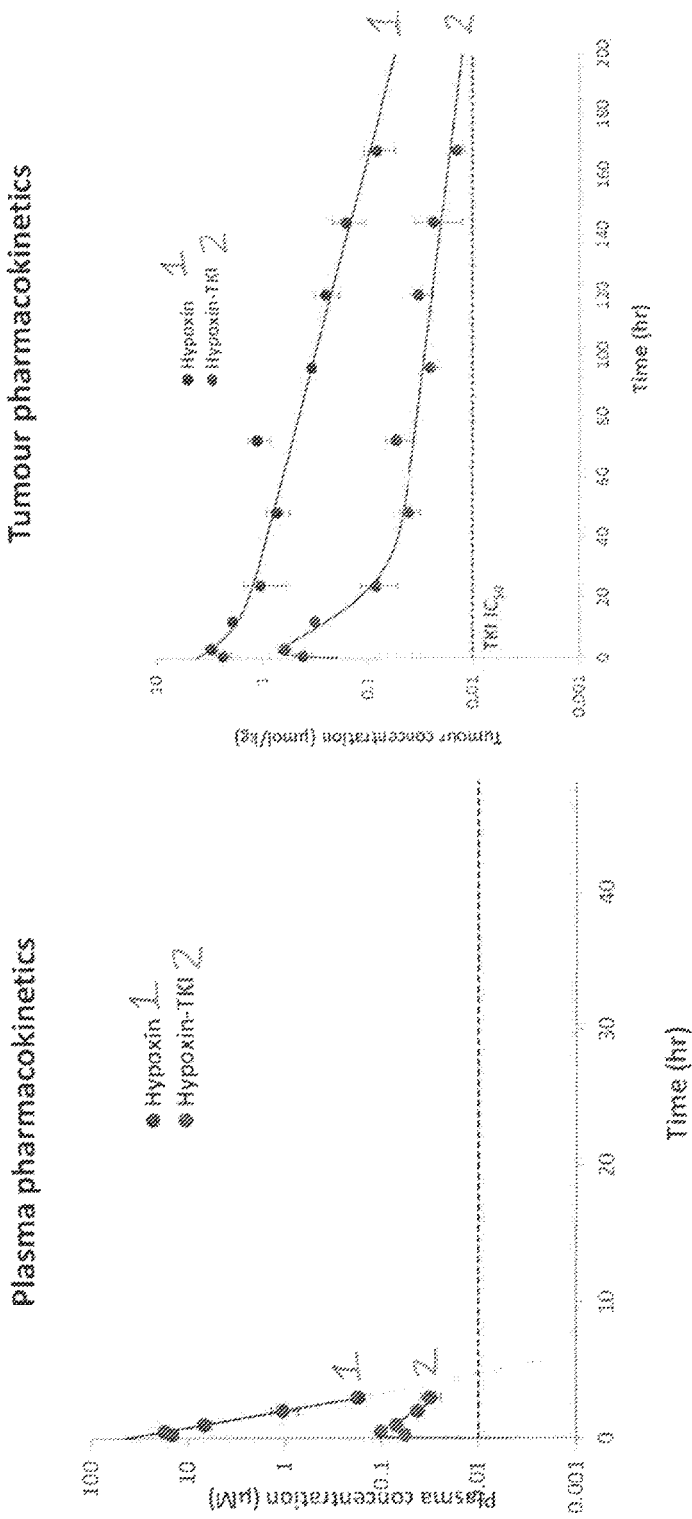

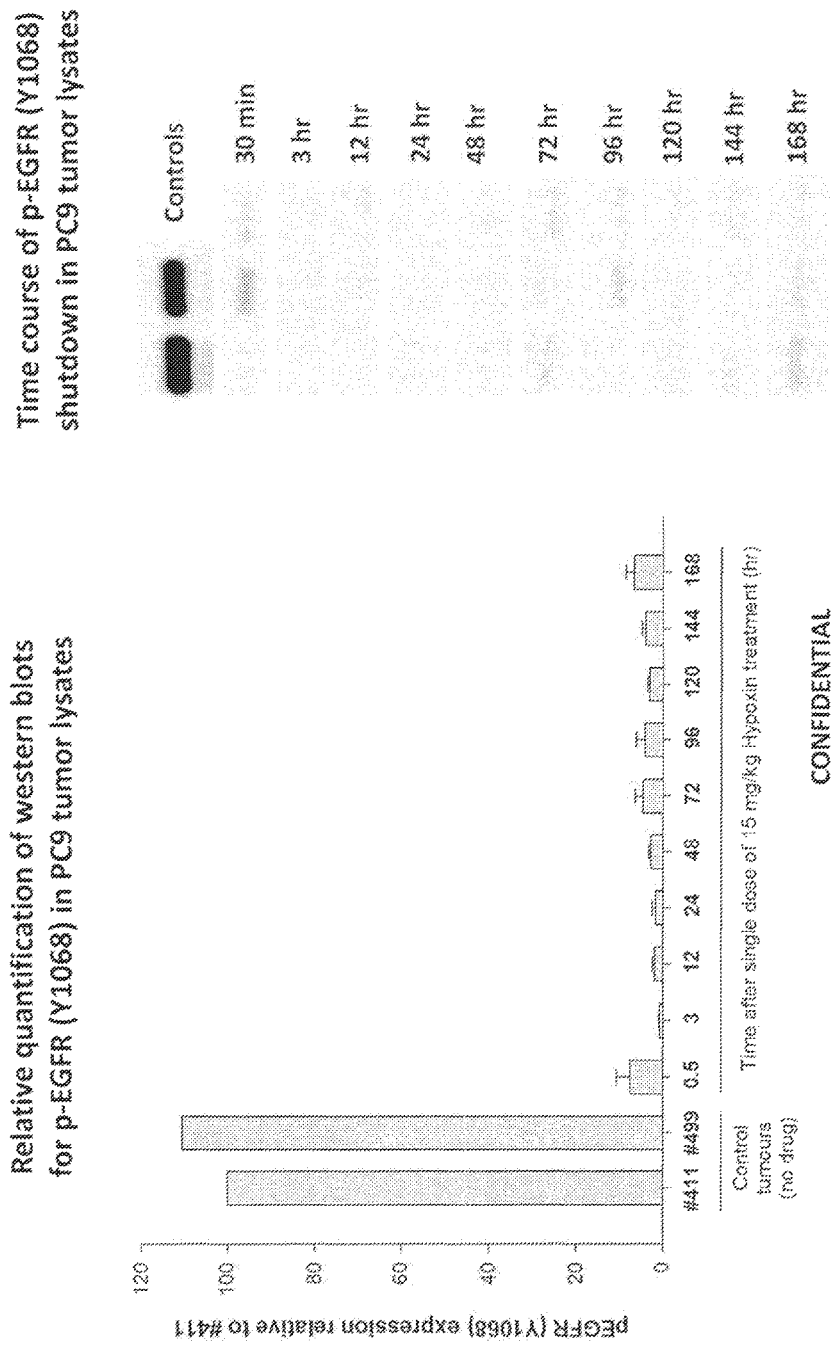
FIG 4. EGFR phosphorylation is inhibited for 7 days following a single dose of Hypoxin (15mg/kg, ip) in nude mice bearing PC9 tumors

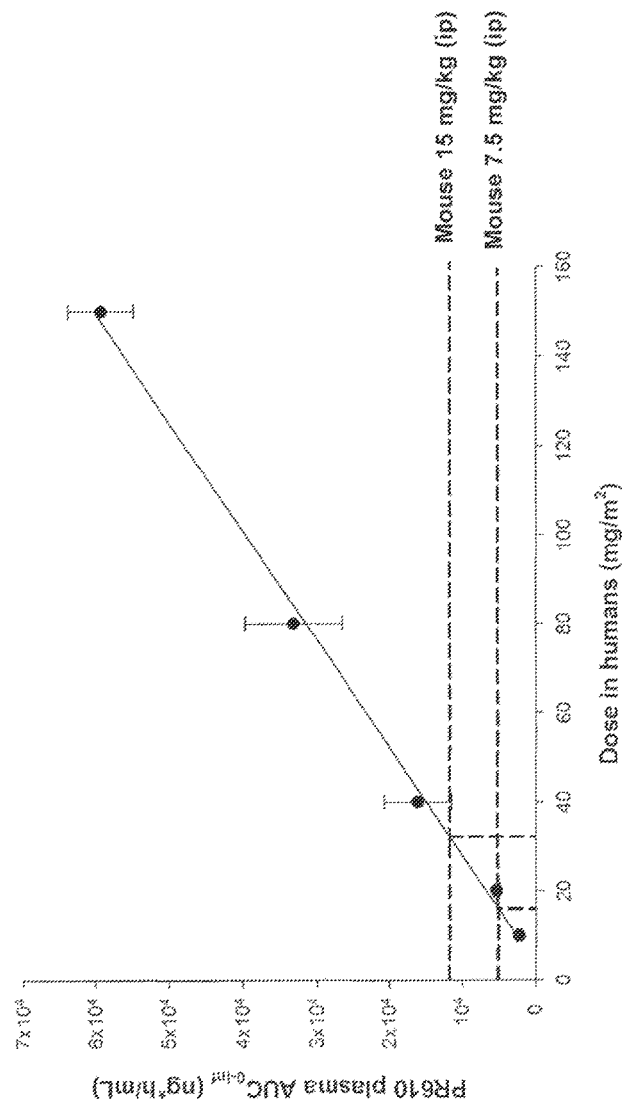

FIG. 6. TKI dependent target modulation in PC9 cells

- Western blot for inhibition of EGFR and ERK1/2 phosphorylation in PC9 cells following exposure to clinically relevant dose range of TKI with or without anoxic conditioning (18h)
- Dose-response for EGFR shutdown compares favourably for Hypoxin-TKI over AZD9291 in PC9 cells (Δ19/wt)
- Interpretation dependent on tumor PK of AZD9291 at plasma PK of 300 – 500 nmol/L

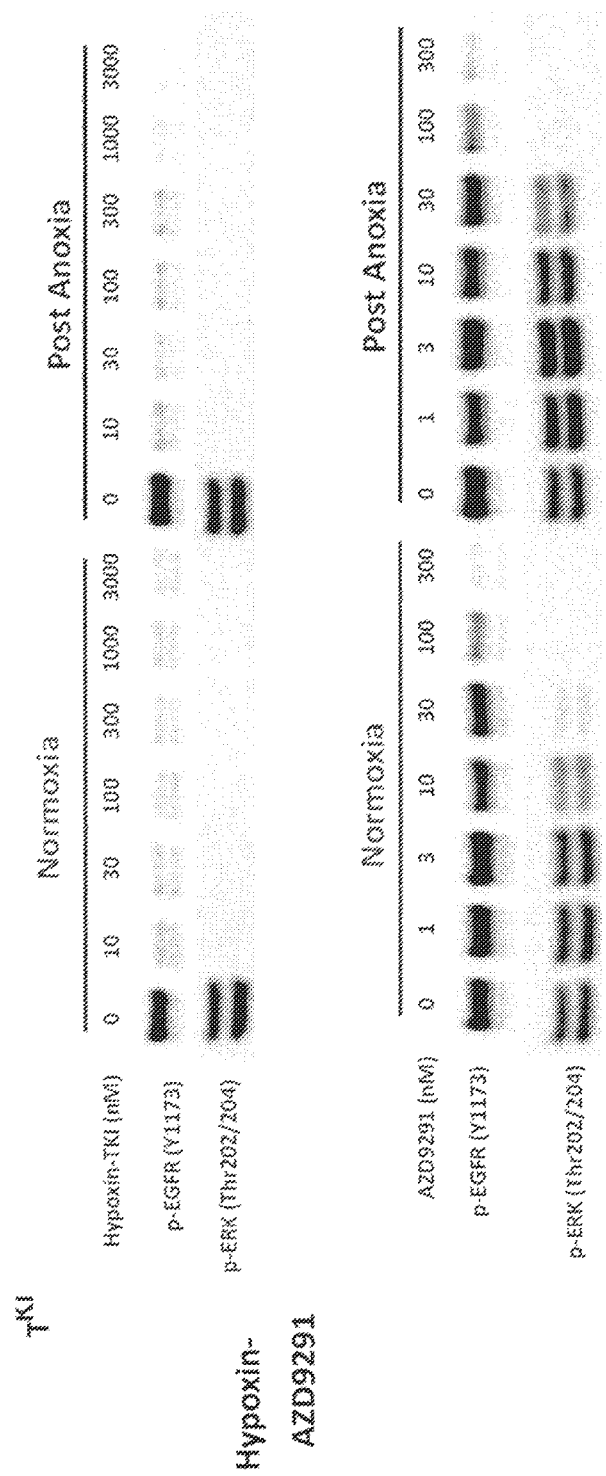

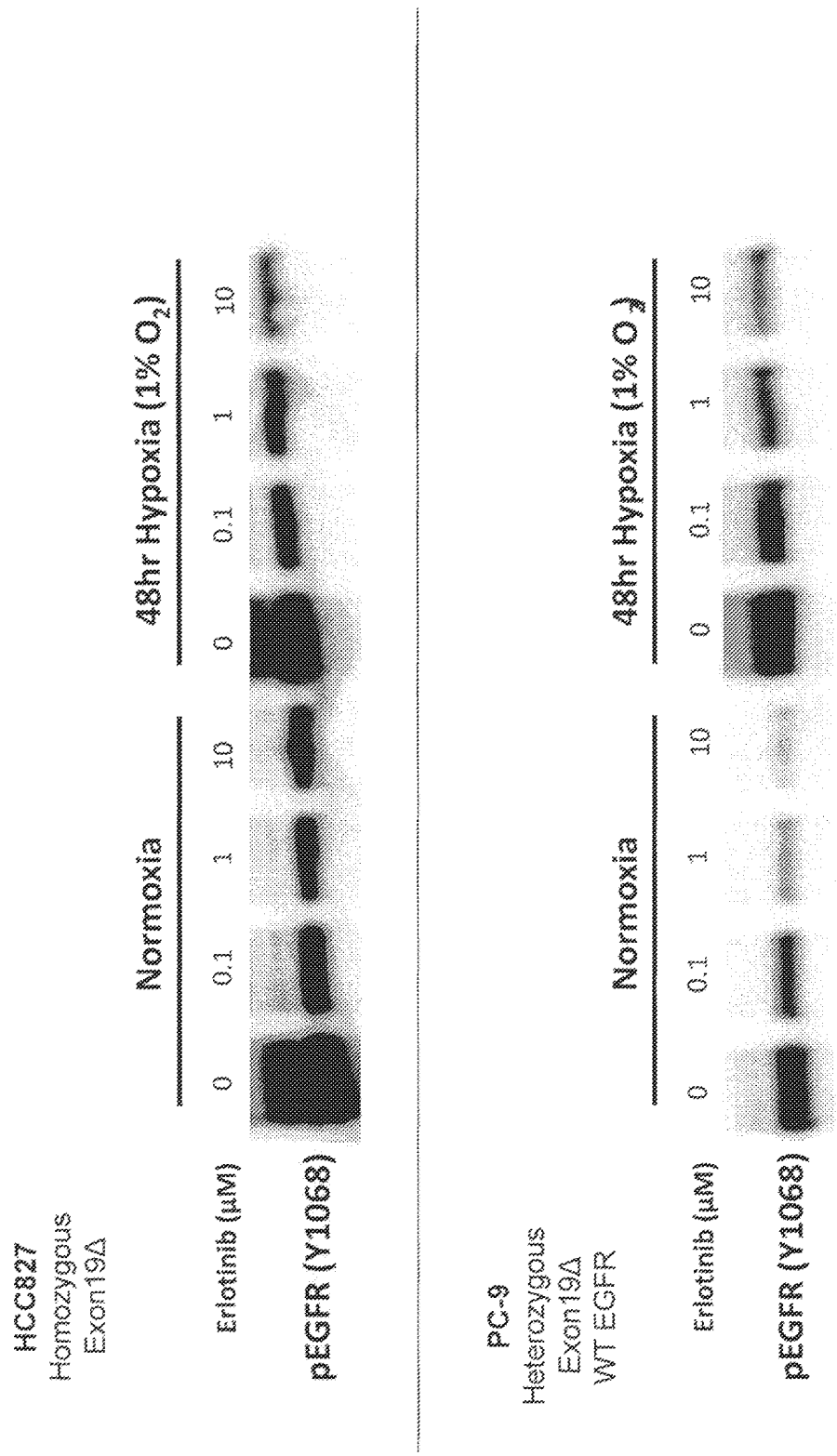

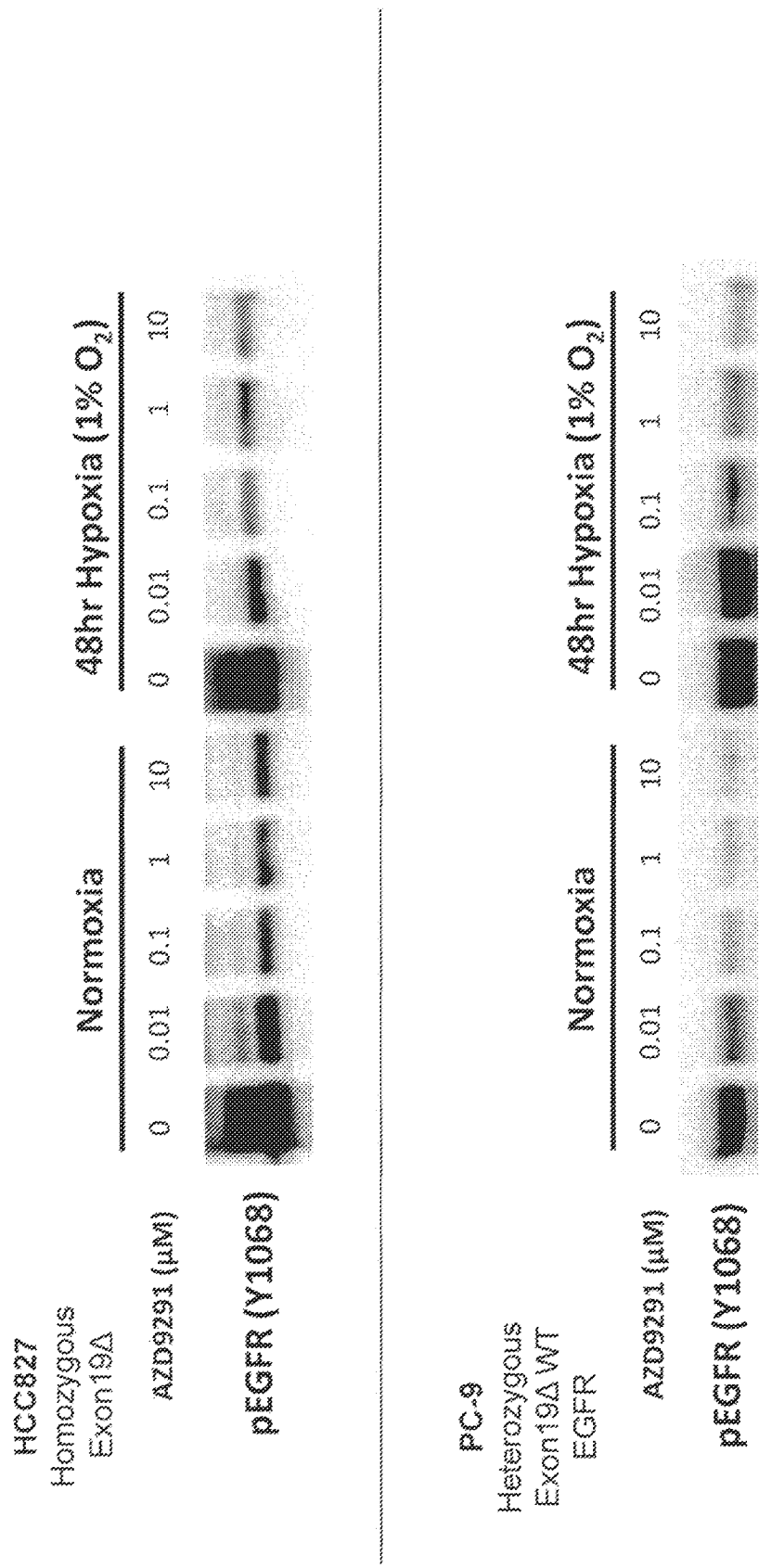
FIG. 8. AZD9291

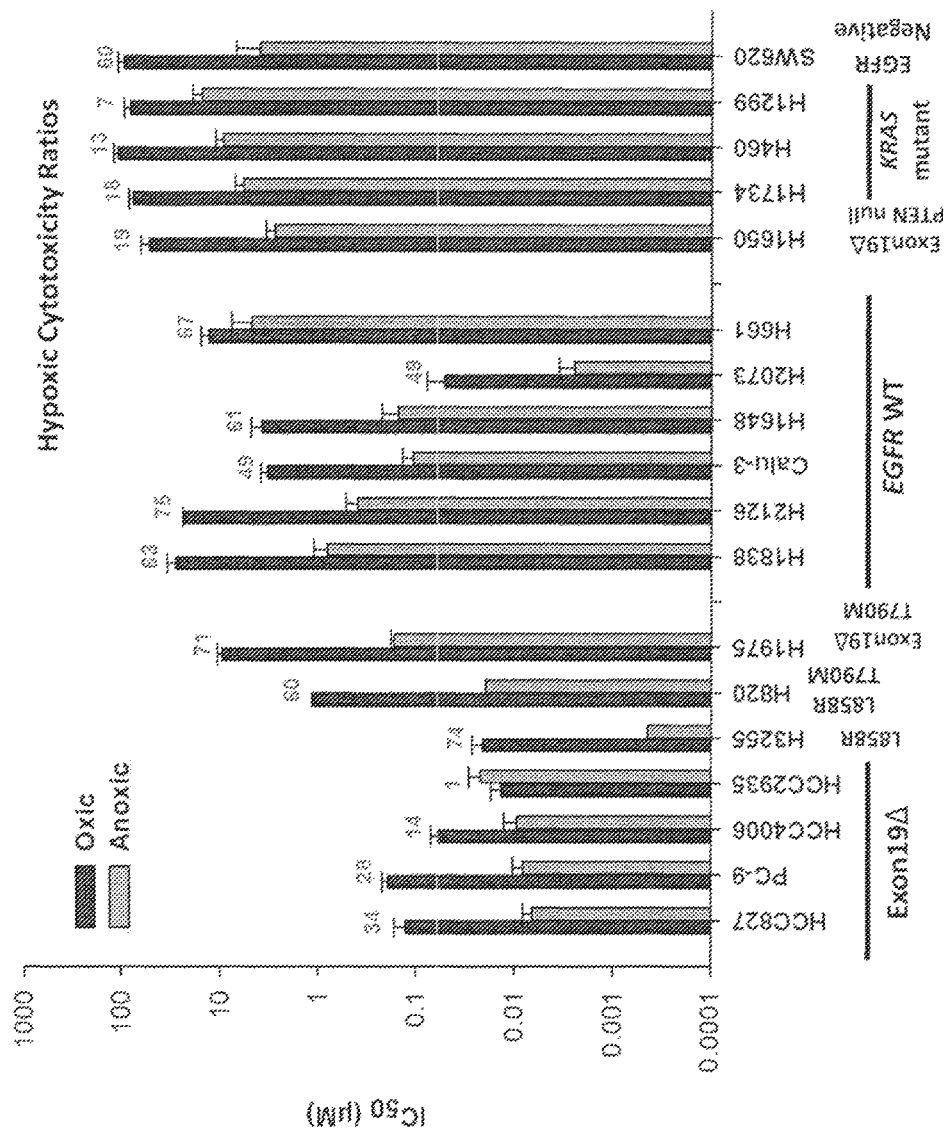
FIG 9. PR610 Oxic / Anoxic IC$_{50}$'s

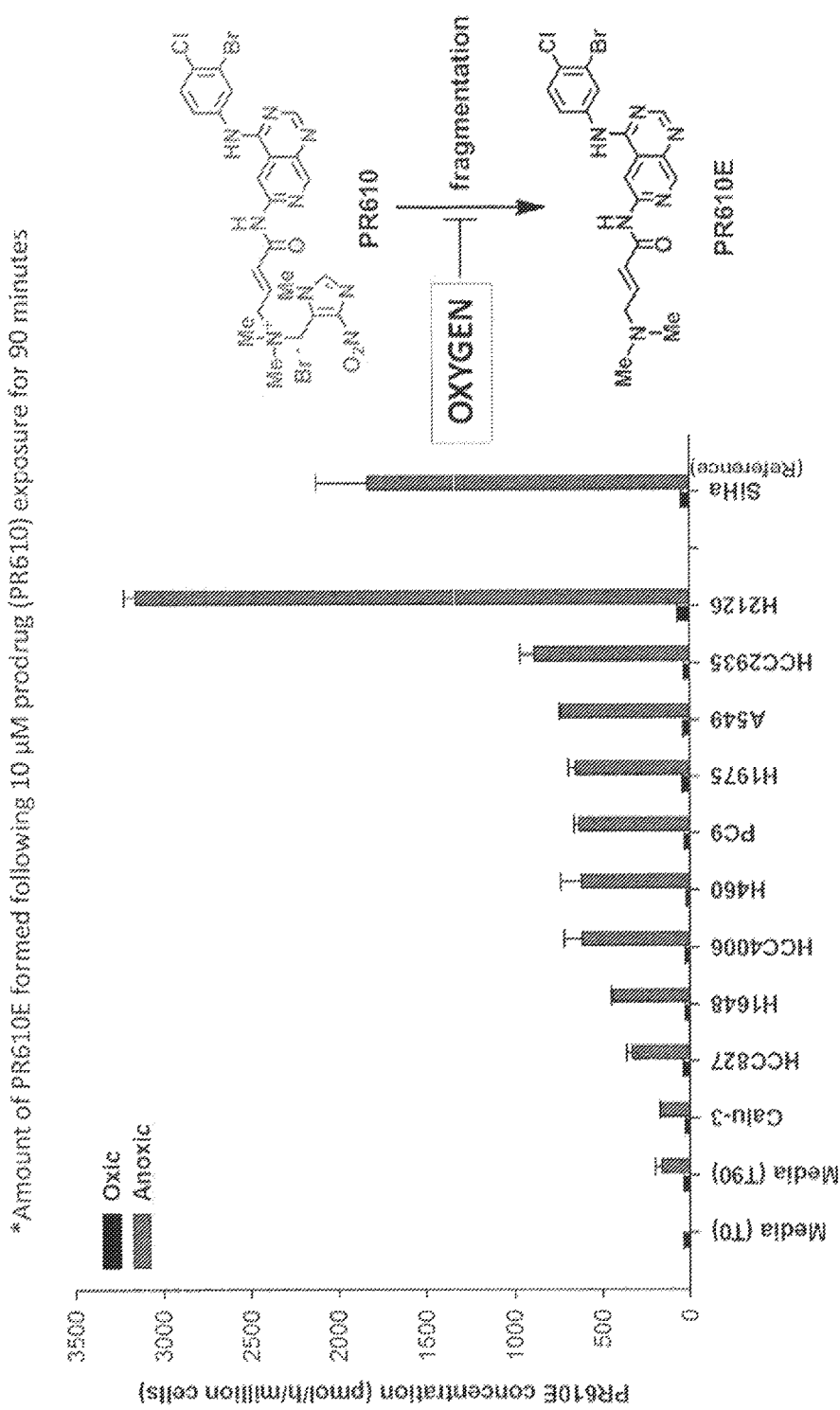

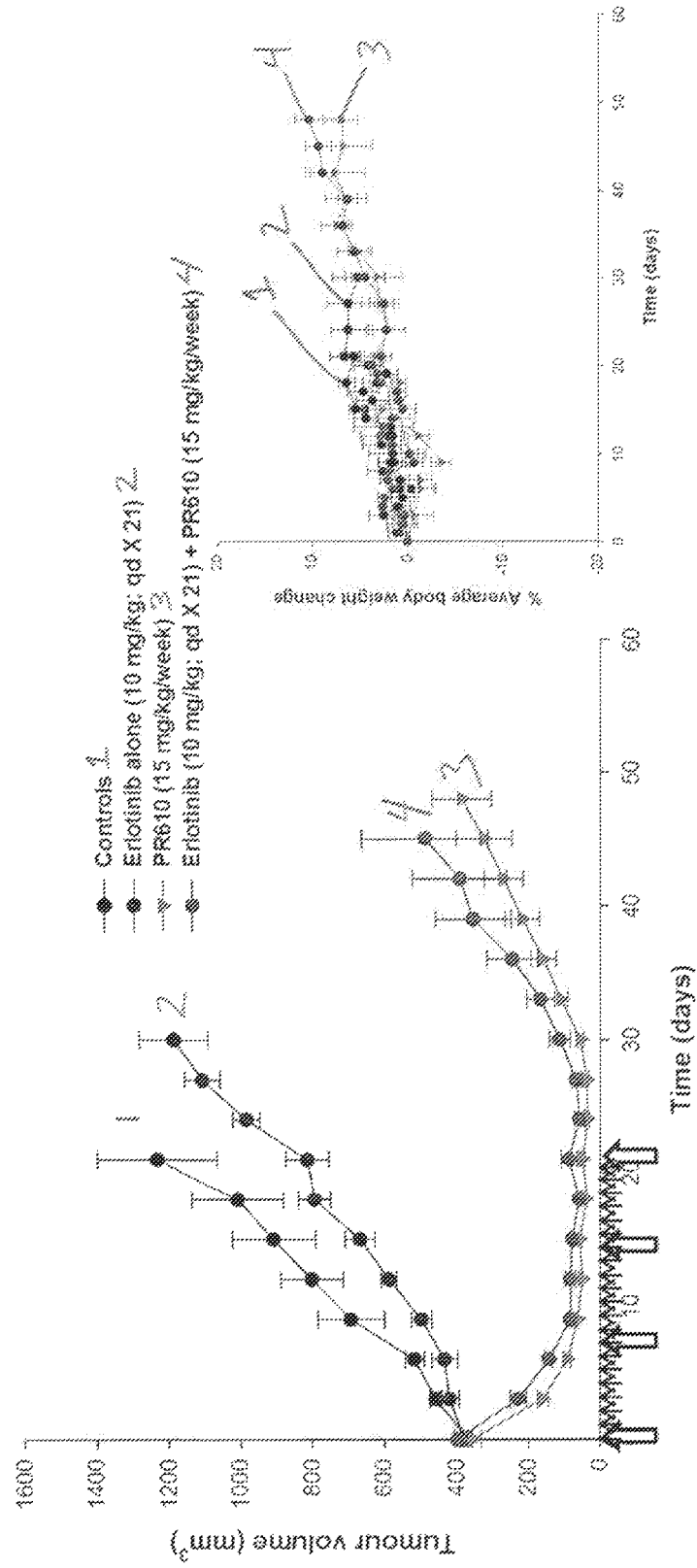

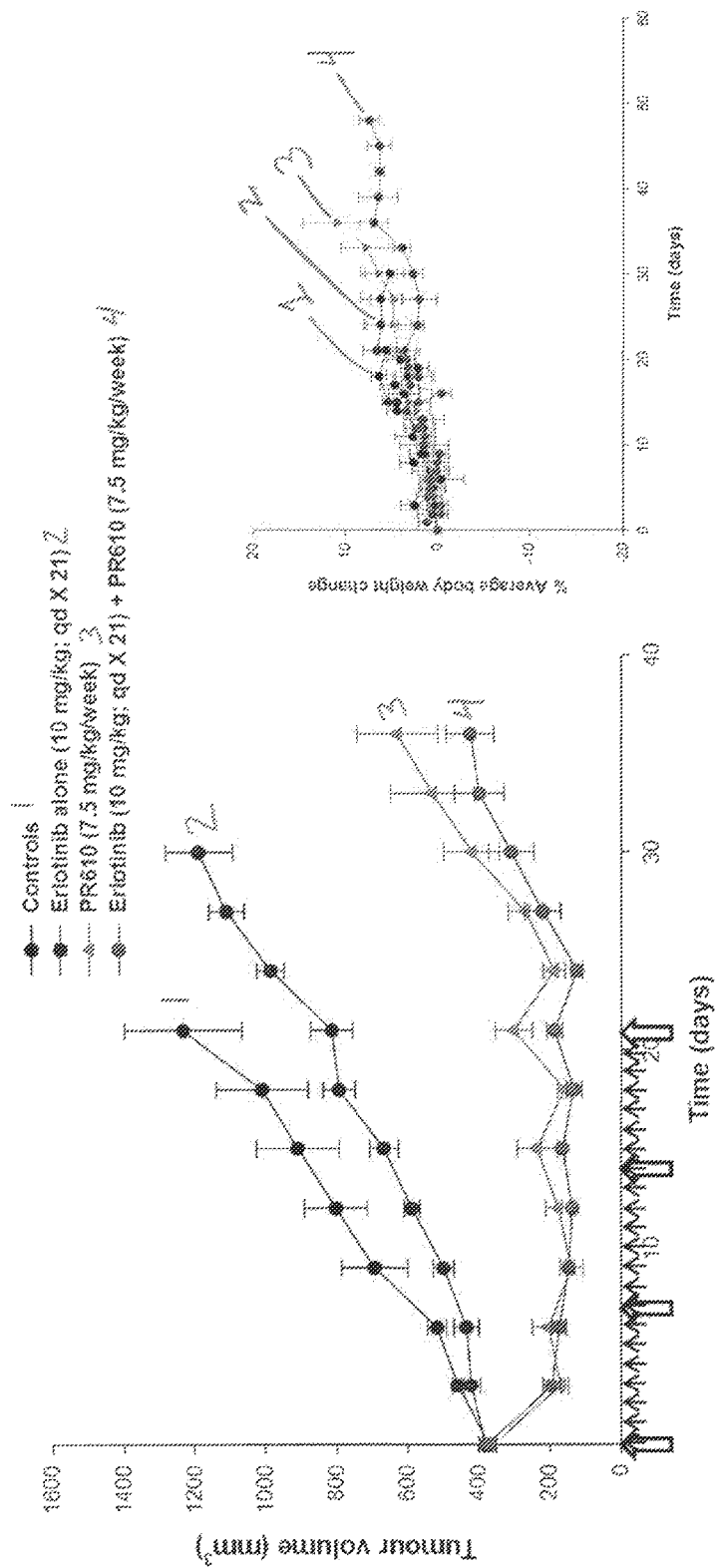
FIG 12. Daily Erlotinib + Weekly PR610 (combination)
- PR610 monotherapy at human equivalent of 16 mg/m²/week comparable to combination
- No benefit from addition of daily erlotinib

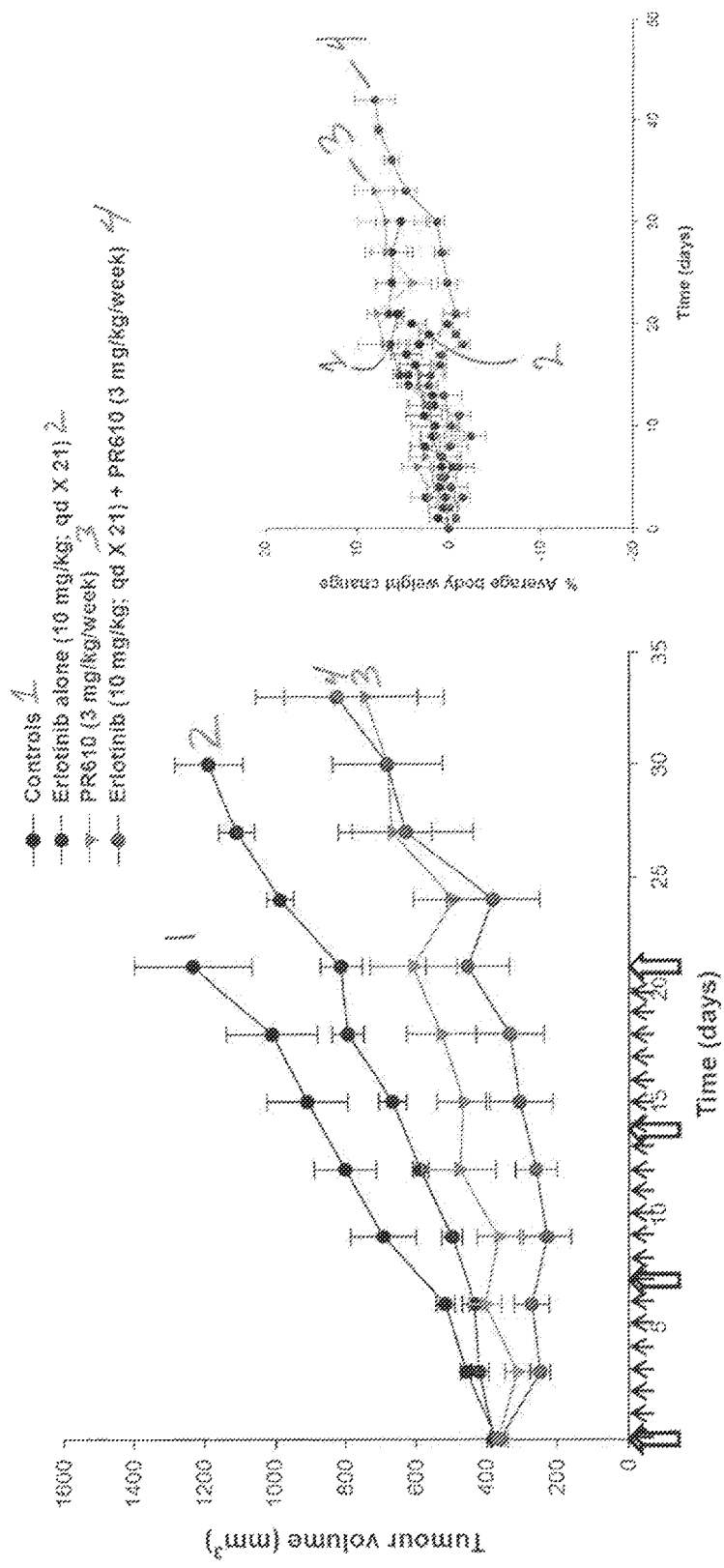

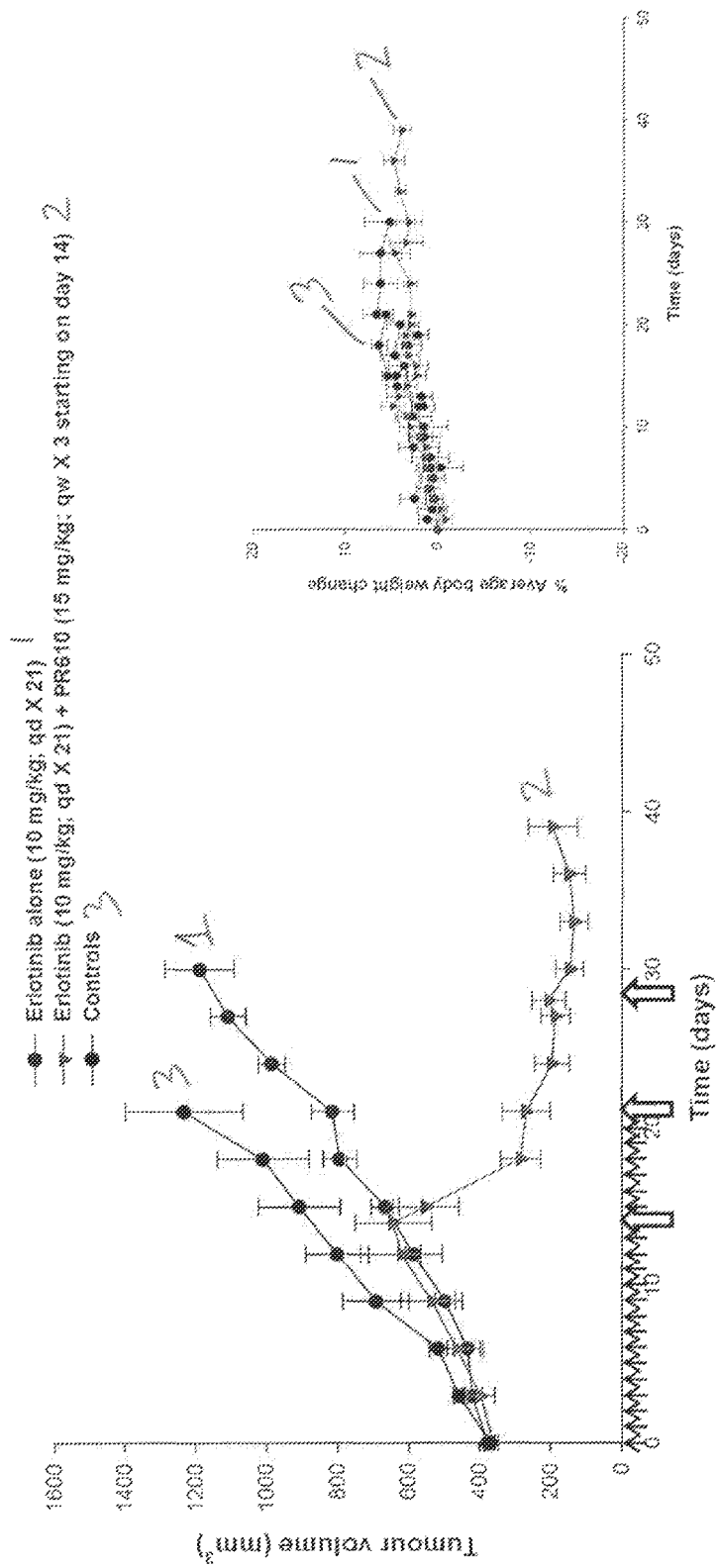
FIG 14. Erlotinib (HED 150 mg) ± weekly PR610 (HED 32 mg/m²) from day 14
- PC-9 tumors progress during erlotinib treatment (at HED)
- Introduction of PR610 at human equivalent of 32 mg/m² on day 14 regresses all tumors

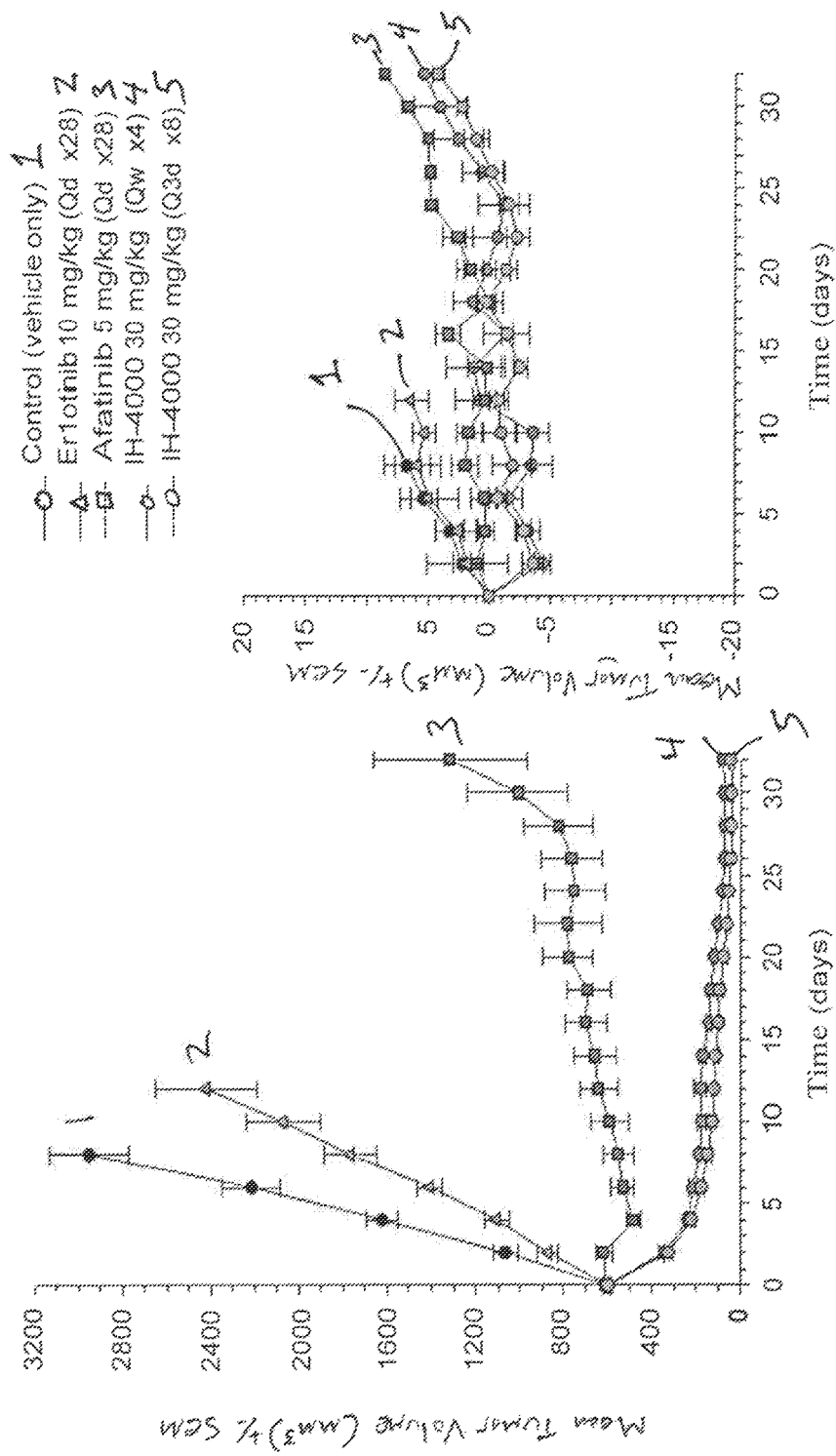
FIG 15. TH-4000 is active against the WT EGFR A431 xenograft at clinically relevant doses

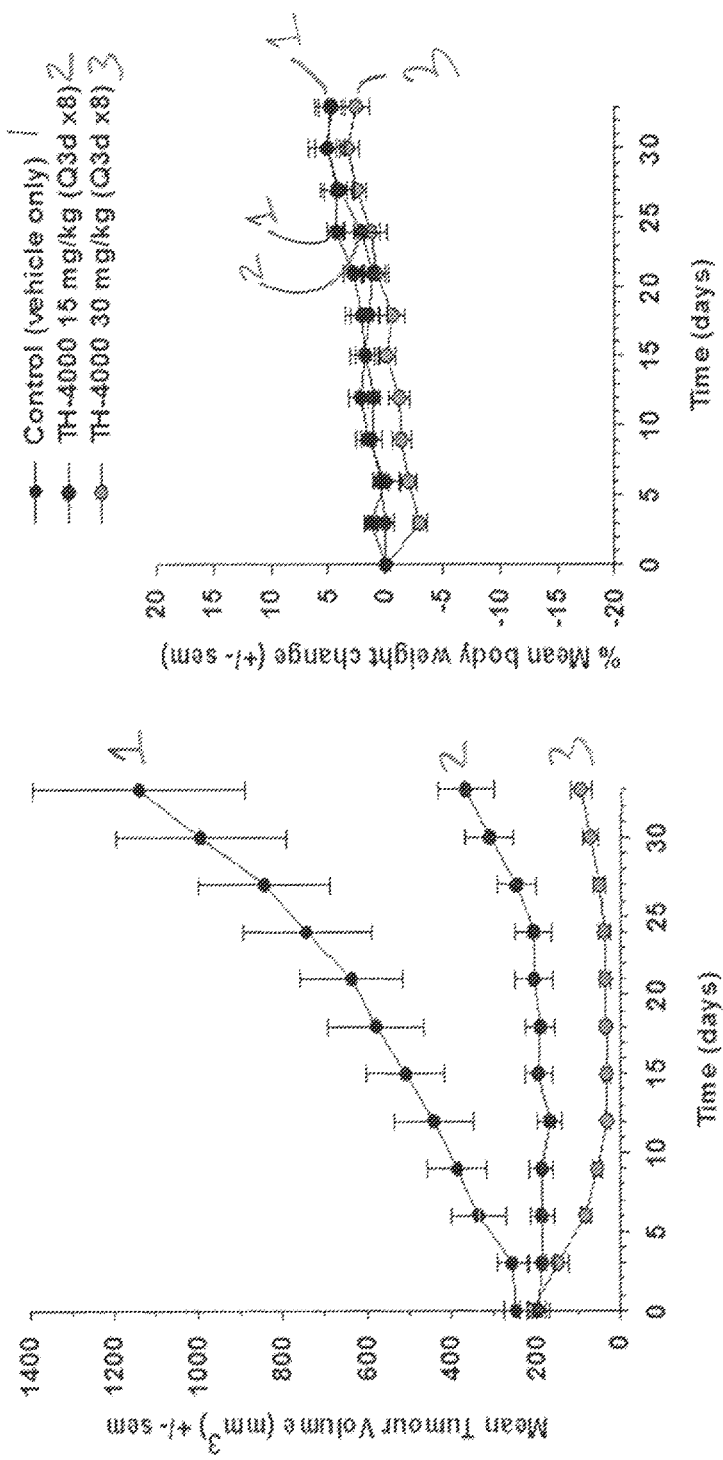
FIG 16. TH-4000 is active against the HER2-positive NCI-N87 gastric tumor xenograft

KINASE INHIBITOR PRODRUG FOR THE TREATMENT OF CANCER

RELATED APPLICATIONS

This application is a U.S. National Phase application, filed under 35 U.S.C. § 371, of International Application No. PCT/US2015/063806, filed on Dec. 3, 2015, which claims priority to, and benefit of, U.S. Provisional Application No. 62/087,212 filed Dec. 3, 2014; U.S. Provisional Application No. 62/150,729 filed Apr. 21, 2015; U.S. Provisional Application No. 62/167,849 filed May 28, 2015; and U.S. Provisional Application No. 62/187,750, filed Jul. 1, 2015. The contents of each of these applications are incorporated by reference in their entirety.

BACKGROUND OF THE INVENTION

Field of the Invention

The present invention provides compositions containing kinase inhibitors in active or prodrug form and methods for treating cancer and other hyperproliferative disease conditions with such compositions alone or in combination with other anti-cancer agents and therapies. In addition, this invention relates generally to analytical testing, and more particularly to the analysis of gene expression or hematology profiles as biomarkers for predicting the effectiveness of Epidermal Growth Factor Receptor (EGFR) tyrosine kinase inhibitors (TKI) in treating cancer. In addition, the present invention relates to kits for use in identifying patients with cancer at risk for resistance to EGFR TKIs. Accordingly, the present invention relates to the fields of medicine, pharmacology, chemistry, and biology.

Background

Kinases play a central role in the regulation of wide variety of cellular processes which has led to the development of kinase inhibitors as therapeutic agents in the treatment of a wide range of disorders, including cancer. Treating cancer is challenging because it is difficult to kill cancer cells while not affecting, or affecting to a lesser extent, normal cells. Killing or otherwise detrimentally affecting normal cells during cancer treatment can cause adverse side effects in patients. EGFR TKIs such erlotinib, gefitinib and afatinib have been approved for the treatment of several cancers including non-small cell lung cancer (see e.g. Felip et al. Clinical Cancer Research, 2008, 14: 3867-3874; Smith et al., 2008, Br. J. Cancer, 98:1630-32; Hamilton et al., 2006, Clin. Can. Res. 12: 2166-71), squamous cell cancer of the head and neck or skin (see e.g. Calvo et al. Annals of Oncology, 2007, 18: 761-767); ovarian cancer (see e.g. Posada et al., Cancer, 2007, 109: 1323-1330). In addition, new drugs designed to target mutant forms of EGFR whilst sparing wild type EGFR like AZD9291, CO-1686 and the like have been developed for the treatment of cancerous tumors (Cross et al., 2014, Can. Discov. 4; 1046).

However, cancer cells can differ from certain normal cells in their level of oxygenation and can be more hypoxic than normal cells. Hypoxia can induce adaptations in gene regulation and associated cellular functions, specifically epidermal growth factor receptor (EGFR: HER1) (Franovic et al. 2007, PNAS: 104: 13092; Wang et al., 2009, Nature Med., 15: 319; Wang et al., 2010, Carcinogenesis, 31:1202; Minakata et al., 2012, Cancer Sci; 103(11): 1946-1954). Tumor hypoxia up-regulates wild type EGFR protein and its cognate ligand TGFα via several HIF dependent mechanisms (Curr Pharm Des 2013; 19:907). One consequence of up-regulation of wild type EGFR protein and cognate ligand in cancer cells is induction of resistance to tyrosine kinase inhibitors (TKI) such as erlotinib, gefitinib or afatinib, which display preferential inhibitory activity towards specific activating EGFR mutant forms (Yun et al, 2008, Proc Natl Acad Sci: 105:2070; Takezawa et al. Cancer Discover 2012; 2: 922-33; Camidge et al. Nat. Rev. Clin. Oncol. 2014; 11: 473-481; Murakami et al. 2014, Plos ONE 9(1):e86459). EGFR activating mutant positive non-small cell lung cancer (NSCLC) is often heterozygous (Soh J, et al. 2009, PLoS ONE 4(10): e7464; Bai et al., 2013, PLoS ONE 8: e54170), and the presence of the wild type allele is associated with limited response to TKI treatment regimens (Taniguchi et al., 2008, Cancer Sci; 99: 929-35). One possibility for overcoming this TKI-resistant state is to silence wild type EGFR signaling arising in hypoxic tumor regions, however conventional EGFR TKI lack the necessary therapeutic index to achieve this goal due to the dosing-limiting side effects associated with on-mechanism inhibition of wild type EGFR in the skin and gastrointestinal tract (Hynes et al., 2005. Nat Rev Can 5:341; Sharma et al., Clin. Cancer Res 2006; 12: 4392s-4395s; Sharma et al, Genes Dev. 2007 21: 3214-3231; Sharma et al., 2007 Nat Rev Can 7:169; Janjigian et al. Cancer Discovery 2014, 4: 1-10).

While progress has been made in this field, the totality of the available data indicate that significant non-responsiveness, due to EGFR genetic polymorphisms is undesirable in patients with cancer. Accordingly, new, safer and more effective methods for treating cancer that address EGFR resistance and non-responsive patients with EGFR genetic polymorphisms are needed, especially for high risk patients.

Certain agents have been made for treating cancer by targeting hypoxic cancer cells (see e.g. for example, PCT Patent Publication Nos. WO 2010/104406 and WO 2011/028135, each of which is incorporated herein by reference) which disclose hypoxia-activated prodrugs (HAP) of EGFR TKI. One such example of such a HAP EGFR TKI is TH-4000. Hypoxia-activated prodrugs (HAP) of EGFR TKI (exemplified by TH-4000) can overcome this mechanism of intrinsic resistance.

There remains a need for compositions and methods for treating cancer. The present invention meets these needs by providing compositions and methods related to the use of the hypoxia activated nitroimidazole prodrug of a kinase inhibitor, TH-4000 in therapy. The hypoxia-dependent metabolism provides tumor selective release of the EGFR TKI in hypoxic tumor cells. The present invention solves the resistance problem and provides methods for determining subjects who are at risk for resistance to EGFR treatment in patients with EGFR gene polymorphisms. The present invention satisfies this and other needs. The high local concentrations provide the necessary therapeutic index to silence wild type EGFR signaling in the hypoxic tumor compartment, as summarized below.

BRIEF SUMMARY OF THE INVENTION

In one aspect, the present invention relates to pharmaceutically acceptable compositions comprising the compound known as PR610, TH-4000 or Hypoxin shown below:

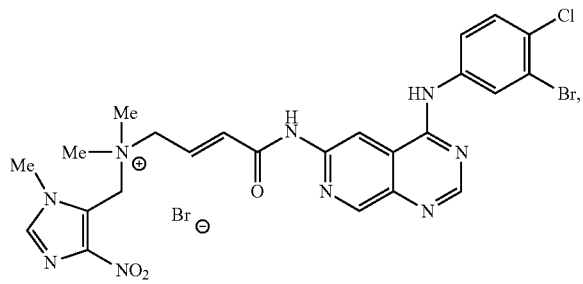 [SMILES: Cn1cnc([N+](=O)[O-])c1C[N+](C)(C)C/C=C/C(=O)Nc1cc2c(Nc3ccc(Cl)c(Br)c3)ncnc2cn1 ; [Br-]]

1 and a pharmaceutically acceptable carrier, excipient, or diluent, such as 2-hydroxylpropyl-β-cyclodextrin. TH-4000 is converted to the tyrosine kinase inhibitor TH-4000E (or PR610E) in vivo:

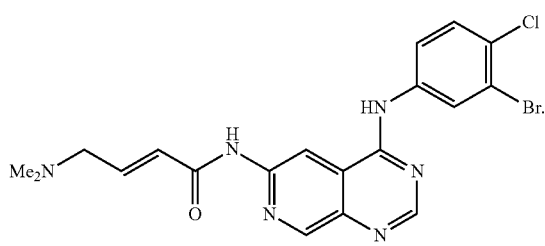 [SMILES: CN(C)C/C=C/C(=O)Nc1cc2c(Nc3ccc(Cl)c(Br)c3)ncnc2cn1]

In another aspect, the present invention provides pharmaceutically acceptable formulations comprising up to about 40 wt % 2-hydroxylpropyl-β-cyclodextrin. The formulation may be diluted (e.g. with an aqueous excipient) prior to administration to a patient.

In another aspect, the present invention provides a unit dose of a pharmaceutically acceptable formulation of TH-4000. In one embodiment, the unit dose of the pharmaceutically acceptable formulation comprises about 5 mg-about 700 mg or about 10 mg-about 180 mg or about 20 mg-about 150 mg of TH-4000. In one embodiment the unit dose comprises about 100 mg of TH-4000.

In another aspect, the present invention provides a method of treating cancer, by administering a therapeutically effective amount of TH-4000 in the range of about 9 mg/m$^2$-about 350 mg/m$^2$, about 10 mg/m$^2$-about 200 mg/m$^2$, about 15 mg/m$^2$-about 150 mg/m$^2$ about 40 mg/m$^2$-about 100 mg/m$^2$ to a patient in need of such treatment. In another embodiment, the present invention provides a method of treating cancer, by administering about 80 mg/m$^2$ TH-4000. In another embodiment, the present invention provides a method of treating cancer, by administering about 32 mg/m$^2$ TH-4000. In one embodiment, the present invention provides a method of treating cancer, by administering about 20 mg/m$^2$ TH-4000. In one embodiment, TH-4000 is administered by intravenous (i.v.) administration. In one embodiment, TH-4000 is administered by intraperitoneal administration. In one embodiment, the therapeutically effective amount of TH-4000 is administered at a frequency of at least once per day, at least once per week or at least once per month. In one embodiment, TH-4000 may be administered for a period of 1-3 weeks or up to at least 30 weeks or up, at least 1 day or up to at least 150 days or up. In some embodiments, longer periods of administration are employed.

In one embodiment, the cancer treated is selected from of non-small cell lung cancer, esophageal cancer, pancreatic cancer, rectal cancer, cancer of the head and neck, cancer of the skin, colon cancer, cervical cancer, bladder cancer, breast cancer, gastrointestinal stromal cancer (GIST), ovarian cancer, gastric cancer, endometrial cancer, uterine cancer, prostate cancer, liver cancer, melanoma, brain cancer and mesothelioma.

In another aspect, the present invention provides pharmaceutically acceptable formulations comprising other tyrosine kinase and/or EGFR inhibitors including, but not limited to erlotinib, dacomitinib, AZD9291. CO-1686, afatinib, gefitinib, rociletinib, cetuximab, icotinib. AZD-8931, lapatinib, dacomitinib, neratinib, AP-26113, Poziotinib, ASP-8273, TAS-121, panitumumab, nimotuzumab, catumaxomab, duligotuzumab and patritumumab.

These and other aspects and embodiments are described in the accompanying figures and detailed description of the invention.

BRIEF DESCRIPTION OF THE DRAWINGS

The invention will now be described in more detail, with reference to the accompanying Figures, in which:

FIGS. 1 and 2 show a comparison of erlotinib and TH-4000 in EGFR mutation-positive NSCLC at clinically relevant HED;

FIG. 3 compares TH-4000—Plasma vs Tumor PK;

FIG. 4 shows that EGFR phosphorylation is inhibited for 7 days following a single dose of TH-4000 (15 mg/kg, ip) in nude mice bearing PC9 tumors FIG. 5 gives human plasma AUC0-inf of TH-4000 as a function of dose (mg/m2);

FIG. 6 shows western blot of TKI dependent target modulation in PC9 cells

FIGS. 7 and 8 shows western blot of TKI dependent target modulation in PC9 cells with erlotinib and AZD9291

FIG. 9 compares TH-4000 Oxic/Anoxic IC50's

FIG. 10 shows TH-4000 metabolism in selected NSCLC cell lines

FIGS. 11-13 show comparative efficacy of TH-4000 administered weekly vs erlotinib administered daily in PC-9 xenografts in individual mice FIG. 14 compares erlotinib (HED 150 mg)+weekly TH-4000 (HED 32 mg/m2) from day 14.

FIG. 15 shows that TH-4000 is active against the WT EGFR A431 xenograft at clinically relevant doses.

FIG. 16 shows that TH-4000 is active against the HER2-positive NCI-N87 gastric tumor xenograft.

DETAILED DESCRIPTION OF THE INVENTION

Figure 17:
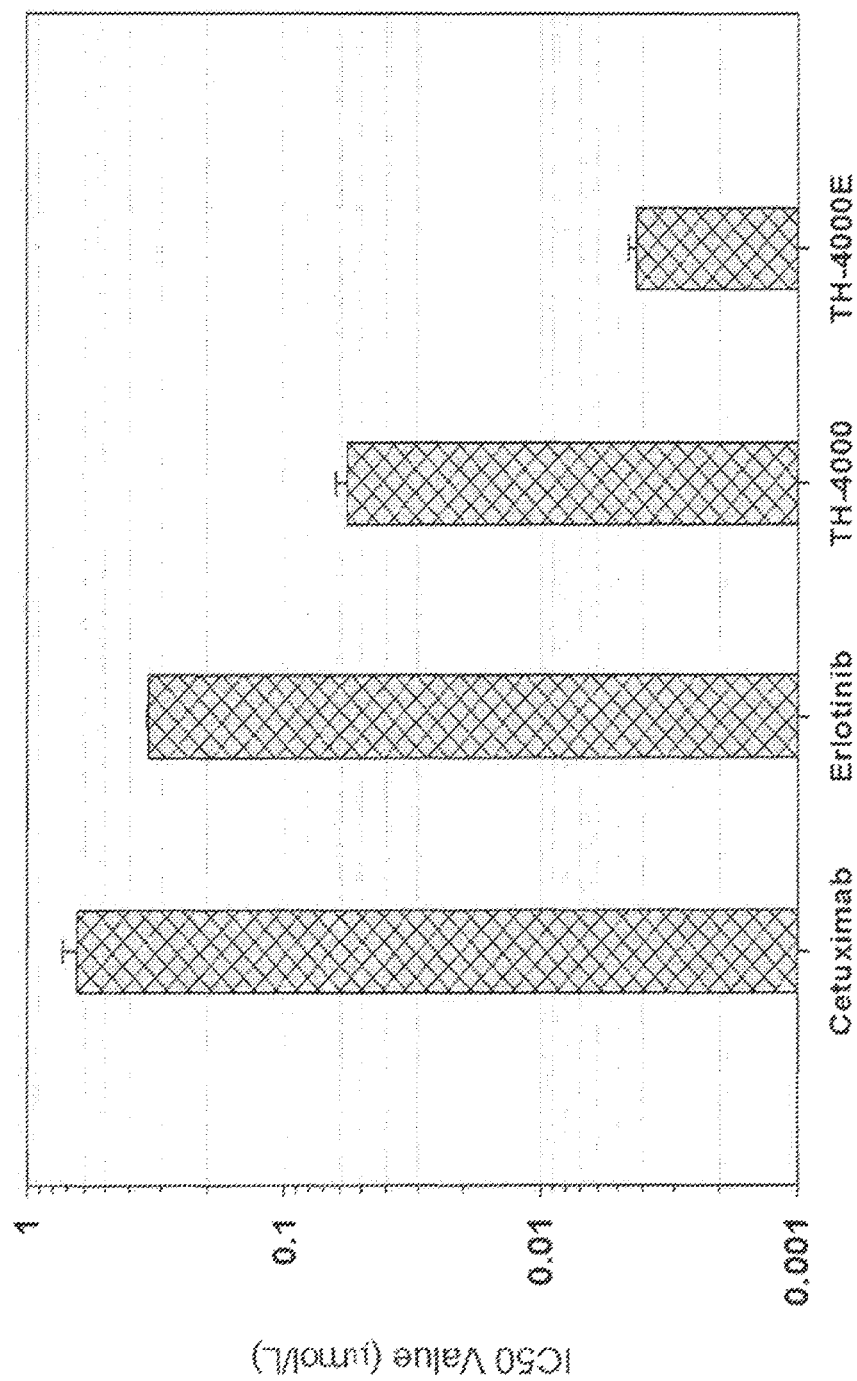
FIG. 17 shows antiproliferative activity of cetuximab, erlotinib, TH-4000 and TH-4000E in the human hypopharnygeal cell line FaDu following a five day continuous exposure under aerobic conditions.

This detailed description of the aspects and embodiments of the present invention is organized into sections as follows. Section I provides definitions of terms used herein. Section II describes the pharmaceutically acceptable formulations of the present invention. Section III provides treatment methods of the present invention. This detailed description is organized into sections only for the convenience of the reader, and disclosure found in any section is applicable to disclosure elsewhere in the specification.

Abbreviations and Definitions

The abbreviations used herein are conventional, unless otherwise defined. The following abbreviations are used: g=gram, $H_2O$=water; h=hour, $IC_{50}$=The concentration of an inhibitor that is required for 50% inhibition of an enzyme in vitro, µM=micromolar, µL=microliter, mg=milligram, mm=millimeter, mM=millimolar, mmol=millimole, mL=milliliter, mOD/min=millioptical density units per minute, min=minute, M=molar, ACLS=Advanced Cardiovascular Life Support, ADL=Activities of Daily Living, AE=Adverse Event, ALT=Alanine Aminotransferase, AST=Aspartate Aminotransferase, ATC=Anatomical Therapeutic Chemical, ATP=Adenosine Triphosphate. AUC=Area Under The Plasma Drug Concentration-Time Curve From 0 to Infinity. AUClast=Area Under The Plasma Drug Concentration-Time Curve From 0 to Last Quantifiable Concentration Time, BP=Blood Pressure, BQL=Below the Quantification Limit, Cmax=Maximum Plasma Concentration, CFR=Code of Federal Regulations, CL=Clearance, Cmax=Peak Plasma Concentration, CNS=Central Nervous System, CR=Complete Response, CRO=Clinical Research Organization, CT=Computed Tomography, CTC=Circulating Tumor Cell, CTCAE=Common Toxicity Criteria for Adverse Events, D5W=5% Dextrose in Water, DLT=Dose-Limiting Toxicity, DOR=Duration of response, ECG=Electrocardiogram, ECOG=Eastern Cooperative Oncology Group, eCRF=Electronic Case Report Form, EGFR=Epidermal Growth Factor Receptor, GI=Gastrointestinal, FDA=Food and Drug Administration, H=Hour, HAP=Hypoxia Activated Prodrug, HED=Human Equivalent Dose, HIV=Human Immunodeficiency Virus, HR=Heart Rate, HRT=Hormone Replacement Therapy, ICF=Informed Consent Form, ICH=International Conference on Harmonization, INR=International Normalized Ratio, IRB/EC=Institutional Review Board/Ethics Committee, IV=Intravenous, Kel=Elimination constant, LLT=Lowest Level Term, LLN=Lower Limit of Normal, MedDRA=Medical Dictionary for Regulatory Activities, MRI=Magnetic Resonance Imaging, MTD=Maximum Tolerated Dose, NSAID=Nonsteroidal Anti-inflammatory Drug, NSCLC=Non-small Cell Lung Cancer. OR=Overall Response, ORR=Overall Response Rate, OS=Overall Survival, PD=Progressive Disease, PET=Photon Emission Tomography. PFS=Progression-Free Survival, PK=Pharmacokinetics, PR=Partial Response, PT=Prothrombin Time or Preferred Term, QT=QT Interval, QTc=QT Interval Corrected for Heart Rate in ECG, QTcB=QTc Using Bazett's Formula, QTcF=QTc Using Fridericia's Formula, RECIST 1.1=Response Evaluation Criteria in Solid Tumors Version 1.1, RR=Respiratory Rate, SAE=Serious Adverse Event, SD=Stable Disease, SOC=System Organ Class, T½=Terminal Half-life, TdP=Torsades de Pointes, TGFα=Transforming Growth Factor-alpha, TH-4000E=TKI effector derived from TH-4000, TKI=Tyrosine Kinase Inhibitor, Tmax=Time to Peak Plasma Concentration, ULN=Upper Limit of Normal, Vβ=Volume of Distribution in Post-Distribution Phase, Vss=Volume of Distribution at Steady State, WT=Wild Type.

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

It is noted here that as used in this specification and the appended claims, the singular forms "a," "an," and "the" include plural reference unless the context clearly dictates otherwise.

"About" refers to ±20% of a quantity and includes, but is not limited to, ±15%, ±10%, and ±5% of the quantity.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

"Anti-cancer effects" include, but are not limited to, anti-tumour effects, the response rate, the time to disease progression and the survival rate. "Anti-tumor" effects include but are not limited to inhibition of tumor growth, tumor growth delay, regression of tumour, shrinkage of tumor, increased time to regrowth of tumor on cessation of treatment and slowing of disease progression.

"Cancer" refers to malignant tumors of potentially unlimited growth that can expand locally by invasion and systemically by metastasis. Examples of cancers include, but are not limited to non-small cell lung cancer, esophageal cancer, pancreatic cancer, rectal cancer, cancer of the head and neck, cancer of the skin, colon cancer, cervical cancer, bladder cancer, breast cancer, gastrointestinal stromal cancer (GIST), ovarian cancer, gastric cancer, endometrial cancer, uterine cancer, prostate cancer, liver cancer, melanoma, brain cancer and mesothelioma.

"Combination therapy" refers to the use of two or more drugs in therapy, i.e., use of a hypoxia activated prodrug as described herein together with conventional drugs used to treat blood cancer is a combination therapy. Administration in "combination" refers to the administration of two agents (e.g., a hypoxia activated prodrug and an agent known for treating a blood cancer) in any manner in which the pharmacological effects of both manifest in the patient at the same time. Thus, administration in combination does not require that a single pharmaceutical composition, the same dosage form, or even the same route of administration be used for administration of both agents or that the two agents be administered at precisely the same time. For example, and without limitation, it is contemplated that one or more of the following agents can be administered in combination with a hypoxia activated prodrug in accordance with the present invention.

As used herein, the term "condition" refers to a disease state for which the compounds, compositions and methods of the present invention are being used against.

As used herein, the term "clinical response" means any or all of the following: a quantitative measure of the response, no response, and adverse response (i.e., side effects).

As used herein, the term "clinical trial" means any research study designed to collect clinical data on responses to a particular treatment, and includes but is not limited to phase I, phase II and phase III clinical trials. Standard methods are used to define the patient population and to enroll subjects.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability): and glycosylation and/or other modifications of the translation product, if required for proper expression and function.

As used herein the term "gene" shall mean a segment of DNA that contains all the information for the regulated biosynthesis of an RNA product, including promoters, exons, introns, and other untranslated regions that control expression.

As used herein, the term "genotype" shall mean an unphased 5' to 3' sequence of nucleotide pair(s) found at one or more polymorphic sites in a locus on a pair of homologous chromosomes in an individual. As used herein, genotype includes a full-genotype and/or a sub-genotype.

As used herein the term "locus" shall mean a location on a chromosome or DNA molecule corresponding to a gene or a physical or phenotypic feature.

"Patient" refers to a mammal in need of treatment for cancer. Generally, the patient is a human. A patient can also be a "warm-blooded animal."

Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable carrier, excipient, or diluent" refers to a carrier, excipient, or diluent that is useful in preparing a pharmaceutical composition that is generally safe, non-toxic and neither biologically nor otherwise undesirable, and includes a carrier, excipient, or diluent that is acceptable for human pharmaceutical use as well as veterinary use. A "pharmaceutically acceptable carrier, excipient, or diluent" includes both one and more than one such carrier, excipient, or diluent.

"Pharmaceutically acceptable salt" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein the term "polymorphism" shall mean any sequence variant present at a frequency of >1% in a population. The sequence variant may be present at a frequency significantly greater than 1% such as 5% or 10% or more. Also, the term may be used to refer to the sequence variation observed in an individual at a polymorphic site. Polymorphisms include nucleotide substitutions, insertions, deletions and microsatellites and may, but need not, result in detectable differences in gene expression or protein function.

As used herein, the term "polymorphic site" shall mean a position within a locus at which at least two alternative sequences are found in a population, the most frequent of which has a frequency of no more than 99%.

As used herein, the term "polynucleotide" shall mean any RNA or DNA, which may be unmodified or modified RNA or DNA. Polynucleotides include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein the term "polypeptide" shall mean any polypeptide comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Reduction" of a symptom or symptoms (and grammatical equivalents of this phrase) refers to decreasing the severity or frequency of the symptom(s), or elimination of the symptom(s).

"Relapsed or refractory" refers to a type of blood cancer that is resistant to treatment with an agent, or responds to treatment with an agent but comes back without being resistant to that agent, or responds to treatment with an agent but comes back resistant to that agent.

"Single agent therapy" or "monotherapy" refers to using a single drug to treat a disease, i.e., using a hypoxia activated prodrug such as, for example, TH-4000 as the only chemical agent to treat a blood cancer. Administration of palliatives and/or vitamins and/or other agents that are administered for purposes other than to treat directly the disease can be administered in single agent therapy. A patient undergoing single agent therapy may also undergo radiation therapy and/or surgery.

"Standard chemotherapy" refers to treatment with drugs in accordance with FDA labeling instructions and/or good clinical practice. Standard chemotherapy is well known to those of skill in the medical arts.

As used herein, a "SNP nucleic acid" is a nucleic acid sequence, which comprises a nucleotide that is variable within an otherwise identical nucleotide sequence between individuals or groups of individuals, thus, existing as alleles. Such SNP nucleic acids are preferably from about 15 to about 500 nucleotides in length. The SNP nucleic acids may be part of a chromosome, or they may be an exact copy of a part of a chromosome, e.g., by amplification of such a part of a chromosome through PCR or through cloning. The SNP nucleic acids are referred to hereafter simply as "SNPs". The SNP probes according to the invention are oligonucleotides that are complementary to a SNP nucleic acid.

"Therapeutically effective amount" of a drug refers to an amount of a drug that, when administered to a patient with cancer or another hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or another hyperproliferative disease; diminishment of extent of disease; delay or slowing of disease progression; amelioration, palliation, or stabilization of the disease state; or other beneficial results.

"Unit dose" of a drug refers to a single dose of a therapeutically effective amount of a drug at a given time.

"Warm blooded animal" means any member of the mammalia class including, but not limited to humans, non-human primates such as chimpanzees and other apes and monkey species, farm animals such as cattle, horses, sheep, goats, and swine; domestic animals such as rabbits, dogs and cats; laboratory animals including rodents, such as rats, mice and guinea pigs, and the like.

Pharmaceutically Acceptable Formulations

In one aspect, the present invention relates to pharmaceutically acceptable formulations comprising the compound known as TH-4000, or a pharmaceutically acceptable salt thereof, with a pharmaceutically acceptable carrier, excipient, or diluent. TH-4000 is described in PCT Pat. App. Pub. No. WO 2011/028135. Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

In one embodiment, the pharmaceutically acceptable formulation comprises TH-4000 and, as an excipient, 2-hydroxylpropyl-β-cyclodextrin. Such a formulation of TH-4000 is described in Example 1 below.

In one embodiment, the unit dose of the pharmaceutically acceptable formulation comprises about 5 mg-about 700 mg or about 10 mg-about 180 mg or about 20 mg-about 150 mg of TH-4000. In one embodiment the unit dose comprises about 100 mg of TH-4000.

In another aspect, the present invention provides a method of treating cancer, by administering a therapeutically effective amount of TH-4000 in the range of about 9 mg/m$^2$-about 350 mg/m$^2$, about 10 mg/m$^2$-about 200 mg/m$^2$, about 15 mg/m$^2$-about 150 mg/m$^2$ about 40 mg/m$^2$-about 100 mg/m$^2$ to a patient in need of such treatment. In another embodiment, the present invention provides a method of treating cancer, by administering about 80 mg/m$^2$ TH-4000. In another embodiment, the present invention provides a method of treating cancer, by administering about 32 mg/m$^2$ TH-4000. In one embodiment, the present invention provides a method of treating cancer, by administering about 20 mg/m$^2$ TH-4000. Suitable unit dose pharmaceutically acceptable formulations of TH-4000 are described in the Examples below.

Treatment Methods

In one embodiment, the cancer treated is selected non-small cell lung cancer, esophageal cancer, pancreatic cancer, rectal cancer, squamous cell carcinoma of the head or neck, squamous cell cancer of the skin, glioblastoma, colon cancer, cervical cancer, bladder cancer, breast cancer, gastrointestinal stromal cancer (GIST), ovarian cancer, gastric cancer, endometrial cancer, uterine cancer and mesothelioma.

Therapeutic dosages of TH-4000 will likely be in the range of 1 mg to 3000 mg per day. The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

In another aspect, the present invention provides a method of treating cancer, by administering a therapeutically effective amount of TH-4000 in the range of about 9 mg/m$^2$-about 350 mg/m$^2$, about 10 mg/m$^2$-about 200 mg/m$^2$, about 15 mg/m$^2$-about 150 mg/m$^2$ about 40 mg/m$^2$-about 100 mg/m$^2$ to a patient in need of such treatment. In another embodiment, the present invention provides a method of treating cancer, by administering about 80 mg/m$^2$ TH-4000. In another embodiment, the present invention provides a method of treating cancer, by administering about 32 mg/m TH-4000. In one embodiment, the present invention provides a method of treating cancer, by administering about 20 mg/m$^2$ TH-4000. TH-4000 Animal studies showing therapeutically effective administration of TH-4000 with antitumor effect are described in the Examples below (e.g., Examples 1-4). A human clinical trial protocol is described in Example 5 below.

Administration

As used herein, the administration of an agent or drug to a subject or patient includes self-administration and the administration by another.

In one embodiment, TH-4000 compounds may be administered by injection in dosage unit formulations. The term 'administration by injection' includes intravenous, intramuscular, subcutaneous and parenteral injections, as well as use of infusion techniques. Effective i.v. administration of TH-4000 for treatment of cancer is described in the Examples. Efficient i.v. bioavailability of TH-4000 is described in Example 3. Typical injection periods are from 1 to about 6 hours.

In one embodiment, the therapeutically effective amount of TH-4000 is administered at a frequency of at least once per day, at least once per week, at least once per two weeks, up to once per month. In one embodiment, TH-4000 is administered for a period of 1-40 weeks, at least 1 week, at least 2 weeks or up to at least 40 weeks. In other embodiments, longer periods of administration are employed.

Various frequencies and periods of TH-4000 administration for effective cancer treatment according to the present methods are described, for example, in Examples 2-5 below.

In one embodiment, TH-4000 is administered in combination with another another anti-proliferative agents, such as those which modulate tyrosine kinase. Optional anti-proliferative agents which can also be administered include but are not limited to erlotinib, dacomitinib, AZD9291, CO-1686, afatinib, gefitinib, rociletinib, cetuximab, icotinib, AZD-8931, lapatinib, dacomitinib, neratinib, AP-26113, Poziotinib, ASP-8273. TAS-121, panitumumab, nimotuzumab, catumaxomab, duligotuzumab and patritumumab.

In particular embodiments the invention provides a method of treating a patient with the non-small cell lung cancer (NSCLC) by administering TH-4000 in an amount in the range of about 10 mg/m$^2$ to about 200 mg/m$^2$ to the patient. In one embodiment the patient is also treated with erlotinib. These and other aspects and embodiments are described in the figures and detailed description of the invention.

In one embodiment, the present invention provides methods for treating metastatic cancer by administering TH-4000 in an amount in the range of about 10 mg/m$^2$ to about 200 mg/m$^2$ to the patient. In one embodiment, the patient is also treated with AZD9291.

In one embodiment, the present invention provides methods for treating cancer administering pharmaceutically acceptable formulations of the present invention comprising hypoxia activated nitroimidazole prodrugs other than TH-4000, and those described in WO 2011/028135.

Diagnostic Methods' and Kits
Hypoxic Markers

The invention advantageously provides a way to determine whether a patient will experience drug resistance during drug treatment, prior to actually taking the drugs. The invention thus provides safer treatment regimens for patients by helping clinicians to (1) provide additional or alternative concomitant medication, (2) alter the dose of the drug or (3) choose not to prescribe that drug for that patient.

In various embodiments of the invention, a marker of hypoxia is used to select patients for treatment and/or to identify patients that are responding (or not responding) to therapy. Hypoxia markers have been developed in the course of studies showing that hypoxia promotes more aggressive solid tumor phenotypes and associates with resistance to radiation and many chemotherapies, as well as likelihood of tumor invasion and poor patient survival. In particular, cells at $pO_2$<10 mm Hg resist the ionizing effect of radiotherapy and cytotoxic effect of chemotherapy. Hypoxic necrotic foci with pseudopalisading tumor cells are one of the features that define glioblastoma (GBM), for example. Thus, a variety of methods have been devised to assess degree of hypoxia in xenografts and patient tumors, and, in accordance with the invention, these methods, suitably modified and practiced as described herein, are used in certain embodiments of the methods of the invention to select patients and assess response to therapy. In general, the invention provides methods for identifying patients suitable for therapy with a hypoxia activated prodrug in which a marker of hypoxia is used to identify that a patient's cancer is hypoxic and then the patient is treated with a hypoxia activated prodrug, i.e., the higher the degree of hypoxia, the more likely the patient will respond to therapy with a hypoxia activated prodrug. Those of skill in the art will appreciate, in view of this disclosure, that these methods are useful in all cancers, not just blood cancers.

Traditionally, the gold standard for measuring hypoxia has been the use of a polarographic oxygen-sensitive probe, which provides direct measurement of tissue oxygen tension. However, this method has limitations, such as its inability to differentiate between viable and necrotic foci, the inaccessibility of many tumor tissues, including those associated with hematologic malignancies of the bone marrow, and the lack of a practical means to apply the technique in large scale. Pimonidazole and EF5, both 2-nitroimidazole compounds, are hypoxia markers that, via immunohistochemical identification of pimonidazole or EF5 protein adducts, can give a reliable estimate of radio-biologically relevant hypoxia. Molecular oxygen competes with reducing equivalents in a manner such that pimonidazole (and EF5) binding is effectively inhibited at oxygen concentrations above 14 micromolar. This method reliably identifies viable hypoxic cells specifically (necrotic cells cannot metabolize pimonidazole or EF5).

Other hypoxic markers that have been identified in preclinical studies that are suitable for use in accordance with the methods of the invention include GLUT-1, HIF-la, CA-IX, LDH-A, osteopontin, microRNA markers, including but not limited to miR-210, and VEGF. Each of these proteins or RNAs is up-regulated in hypoxia, and they can be detected by tumor biopsy. More conveniently, however, some of these markers, i.e., CA-IX LDH-A, osteopontin, microRNA markers, including but not limited to miR-210, and VEGF, will be detectable in the blood, serum, or plasma of a patient, allowing a simple blood test, instead of a tumor biopsy, to be used to select patients for hypoxia activated prodrug therapy.

In addition, studies have examined the spatial relationship between tumor hypoxia assessed by immunohistochemistry and [18F]-FDG and [18F]-FMISO autoradiography and PET imaging, and these compounds and similar PET tracers, such as [18F]-EF5, [18F]-FAZA, and [18F]-HX4, can be employed in accordance with the methods of the invention. In addition to autoradiography and PET imaging, MRI imaging of hypoxia, in particular dynamic contrast-enhanced MRI (DCE-MRI), can be used to identify hypoxic cancers and thus identify patients ideal for treatment with hypoxia-activated prodrugs.

Hypoxyprobe™-1 (pimonidazole hydrochloride, marketed by Hypoxyprobe, Inc.) when administered, either IV or orally, is distributed to all tissues in the body including the brain but only forms adducts with proteins in those cells that have an oxygen concentration less than 14 micromolar (equivalent to a $pO_2$ of 10 mm Hg at 37 degrees Celsius). Hypoxyprobe-1MAb1 is a mouse IgG1 monoclonal antibody that detects protein adducts of Hypoxyprobe-1 in hypoxic cells. This reagent is typically added to each tissue sample. Chromogenic or fluorescent secondary antibody reagents are then used in accordance with the invention to reveal where Hypoxyprobe-1 adducts have formed in the hypoxic tissue.

In addition to these markers of hypoxia, there are other markers that can be used to select patients for hypoxia activated prodrug therapy. The hypoxia activated prodrugs of the invention are activated by reductases, so biopsies or blood tests that show a patient has higher levels of an activating reductase, such as POR (P450 oxido-reductase), MTRR (methionine synthase reductase), and/or NOS (nitric oxide synthase), demonstrate that a patient is more likely to respond to hypoxia activated prodrug therapy. Furthermore, the DNA damage induced by these hypoxia activated prodrugs is repaired by the HDR (also known as HR) system, and the lower the levels of the proteins in this system, including but not limited to BRCA, FANG, XPF (also known as ERCC4), XRCC2 and/or XRCC3, in the blood or tumor biopsy of a patient, the more likely the patient will respond to hypoxia activated prodrug therapy.

Relevant populations with wild type EGFR may be identified in clinical trials of TH-4000. Subjects with and without EGFR resistance are flagged and genotyped as described below.

The maximum tolerated dose (MTD) for a compound is determined using methods and materials known in the medical and pharmacological arts, for example through dose-escalation experiments. One or more patients is first treated with a low dose of the compound, typically 10% of the dose anticipated to be therapeutic based on results of in vitro cell culture experiments. The patients are observed for a period of time to determine the occurrence of toxicity. Toxicity is typically evidenced as the observation of one or more of the following symptoms: vomiting, diarrhoea, peripheral neuropathy, ataxia, neutropaenia, or elevation of liver enzymes. If no toxicity is observed, the dose is increased 2-fold, and the patients are again observed for evidence of toxicity. This cycle is repeated until a dose producing evidence of toxicity is reached. The dose immediately preceding the onset of unacceptable toxicity is taken as the MID. A determination of the MTD is provided above.

Individuals carrying wild type alleles may be detected at the DNA, the RNA, or the protein level using a variety of techniques that are well known in the art. Strategies for identification and detection are described in e.g. EP 730,663, EP 717,113, and PCT US97/02102. The identification of alleles containing wild type may involve the amplification of DNA from target samples. This can be accomplished by e.g., PCR. See generally PCR Technology: Principles and Applications for DNA Amplification, (ed. Erlich, Freeman Press, New York, N.Y., 1992); PCR Protocols: A Guide to Methods and Applications (eds. Innis, et al., Academic Press, San Diego, Calif., 1990). The detection of wild type in specific DNA sequences, can be accomplished by a variety of methods including, but not limited to, restriction-fragment-length-wild type detection based on allele-specific restriction-endonuclease cleavage (Kan & Dozy. Lancet 11:910-912 (1978)), hybridization with allele-specific oligonucleotide probes (Wallace et al, Nucl. Acids Res. 6:3543-3557 (1978)), including immobilized oligonucleotides (Saiki et al., Proc. Natl. Acad. Sci. USA, 86:6230-6234 (1969)) or oligonucleotide arrays (Maskos & Southern, Nucl. Acids Res. 21:2269-2270 (1993)), allele-specific PCR (Newton et al., Nucl. Acids Res. 17:2503-2516 (1989)), mismatch-repair detection (MRD) (Faham & Cox, Genome Res. 5:474-482 (1995)), binding of MutS protein (Wagner et al., Nucl. Acids Res. 23:3944-3948 (1995), denaturing-gradient gel electrophoresis (DGGE) (Fisher & Lerman, Proc. Natl. Acad. Sci. U.S.A. 80:1579-1583 (1983)), single-strand-conformation-wild type detection (Orita et al., Genomics 5:874-879 (1983)), RNAse cleavage at mismatched base-pairs (Myers et al., Science 230:1242 (1985)), chemical (Cotton et al., Proc. Natl. Acad. Sci. U.S.A., 8Z:4397-4401 (1988)) or enzymatic (Youil et al., Proc. Natl. Acad. Sci. U.S.A. 92:87-91 (1995)) cleavage of heteroduplex DNA, methods based on allele specific primer extension (Syvanen et al., Genomics 8:684-692 (1990)), genetic bit analysis (GBA) (Nikiforov et al., Nucl. Acids Res. 22:4167-4175 (1994)), the oligonucleotide-ligation assay (OLA) (Landegren et al., Science 241:1077 (1988)), the allele-specific ligation chain reaction (LCR) (Barrany. Proc. Natl. Acad. Sci. U.S.A. 88:189-193 (1991)), gap-LCR (Abravaya et al., Nucl. Acids Res. 23:675-682 (1995)), radioactive andior fluorescent DNA sequencing using standard procedures well known in the art, and peptide nucleic acid (PNA) assays (Orum et al., Nucl. Acids Res. 21:5332-5356 (1993); Thiede et al., Nucl. Acids Res. 24:983-984 (1996)). Additional guidance is provided by Sambrook J et al., Molecular Cloning: A Laboratory Manual, Third Edition (Cold Spring Harbor Press, Cold Spring Harbor, N.Y., 2000). In one embodiment, the technique for detecting gene expression includes the use of a gene chip. The construction and use of gene chips are well known in the art. See, U.S. Pat. Nos. 5,202,231; 5,445,934; 5,525,464; 5,695,940; 5,744,305; 5,795,716 and 5,800,992. See also, Johnston, M. Curr Biol 8:R171-174 (1998); Iyer V R et al., Science 283:83-87 (1999) and Elias P, "New human genome 'chip' is a revolution in the offing" Los Angeles Daily News (Oct. 3, 2003).

In a particularly preferred embodiment the detection of the genetic wild type can be accomplished by means of so called TAQMAN® SNP genotyping assays (available from Applied Biosystems, Foster City, Calif.).

It is preferred that the individuals included in the clinical population have been graded for the existence of the medical condition of interest. This grading of potential patients could employ a standard physical exam or one or more lab tests. Alternatively, grading of patients could use gene expression pattern for situations where there is a strong correlation between gene expression pattern and disease susceptibility or severity.

The therapeutic treatment of interest is administered to each individual in the trial population and each individual's response to the treatment is measured using one or more predetermined criteria. It is contemplated that in many cases, the trial population will exhibit a range of responses and that the investigator will choose the number of responder groups (e.g., low, medium, high) made up by the various responses.

After both the clinical and wild type data have been obtained, correlations between individual response and genotype or haplotype content are created. Correlations may be produced in several ways. In one method, individuals are grouped by their genotype or haplotype (or haplotype pair) (also referred to as a wild type group), and then the averages and standard deviations of clinical responses exhibited by the members of each wild type group are calculated.

Results are analyzed to determine if any observed variation in clinical response between wild type groups is statistically significant. Statistical analysis methods which may be used are described in L. D. Fisher & G. vanBelle. Biostatistics: A Methodology for the Health Sciences (Wiley-Interscience, New York, 1993).

A second method for finding correlations between gene expression pattern and clinical responses uses predictive models based on error-minimizing optimization algorithms. One of many possible optimization algorithms is a genetic algorithm (R. Judson, "Genetic Algorithms and Their Uses in Chemistry" in Reviews in Computational Chemistry, Vol. 10, pp. 1-73, K. B. Lipkowitz and D. B. Boyd, eds. (VCH Publishers, New York, 1997). Simulated annealing (Press et al., "Numerical Recipes in C: The Art of Scientific Computing", Cambridge University Press (Cambridge) 1992, Ch. 10), neural networks (E. Rich and K. Knight, "Artificial Intelligence", 2nd Edition McGraw-Hill, New York, 1991, Ch. 18), standard gradient descent methods (Press et al., supra Ch. 10), or other global or local optimization approaches (see discussion in Judson, supra) could also be used.

ANOVA is used to test hypotheses about whether a response variable is caused by or correlated with one or more traits or variables that can be measured (Fisher & vanBelle, supra, Ch. 10). For statistical methods for use in the methods of this invention, see: Statistical Methods in Biology, 3rd edition, Bailey N T J, (Cambridge Univ. Press, 1997); Introduction to Computational Biology, Waterman M S (CRC Press, 2000) and Bioinformatics, Baxevanis A D & Ouellette B F F editors (John Wiley & Sons, Inc., 2001).

From the analyses described above, a mathematical model may be readily constructed by the skilled artisan that predicts clinical response as a function of gene expression pattern.

The identification of an association between a clinical response and a genotype or haplotype (or haplotype pair) for the gene may be the basis for designing a diagnostic method to determine those individuals who will or will not respond to the treatment, or alternatively, will respond at a lower level and thus may require more treatment, i.e., a greater dose of a drug. The diagnostic method may take one of several forms: for example, a direct DNA test (i.e., of gene expression pattern), a serological test, or a physical exam measurement. The only requirement is that there be a good correlation between the diagnostic test results and the underlying genotype or haplotype that is in turn correlated with the clinical response. In a preferred embodiment, this diagnostic method uses the predictive haplotyping method described above.

A computer may implement any or all analytical and mathematical operations involved in practicing the methods of the present invention. In addition, the computer may execute a program that generates views (or screens) displayed on a display device and with which the user can interact to view and analyze large amounts of information relating to the gene and its genomic variation, including chromosome location, gene structure, and gene family, gene expression data, wild type data, genetic sequence data, and clinical data population data (e.g., data on ethnogeographic origin, clinical responses, genotypes, and haplotypes for one or more populations). The wild type data described herein may be stored as part of a relational database (e.g., an instance of an Oracle database or a set of ASCII flat files). These wild type data may be stored on the computer's hard drive or may, for example, be stored on a CD-ROM or on one or more other storage devices accessible by the computer. For example, the data may be stored on one or more databases in communication with the computer via a network.

In other embodiments, the invention provides methods, compositions, and kits for haplotyping and/or genotyping the gene in an individual. The compositions contain oligonucleotide probes and primers designed to specifically hybridize to one or more target regions containing, or that are adjacent to, a wild type site. The methods and compositions for establishing the genotype or haplotype of an individual at the wild type sites described herein are useful for studying the effect of the wild type in the etiology of diseases affected by the expression and function of the protein, studying the efficacy of drugs targeting, predicting individual susceptibility to diseases affected by the expression and function of the protein and predicting individual responsiveness to drugs targeting the gene product.

In yet another embodiment, the invention provides a method for identifying an association between a gene expression pattern and a trait. In preferred embodiments, the trait is susceptibility to a disease, severity of a disease, the staging of a disease or response to a drug. Such methods have applicability in developing diagnostic tests and therapeutic treatments for all pharmacogenetic applications where there is the potential for an association between a genotype and a treatment outcome including efficacy measurements, PK measurements and side effect measurements.

The invention also provides a computer system for storing and displaying wild type data determined for the gene. The computer system comprises a computer processing unit; a display; and a database containing the gene expression pattern data. The gene expression pattern data may include the gene expression pattern in a reference population. In a preferred embodiment, the computer system is capable of producing a display showing gene expression pattern organized according to their evolutionary relationships.

In practicing the present invention, many other conventional techniques in molecular biology, microbiology and recombinant DNA are used. These techniques are well-known and are explained in, e.g., "Current Protocols in Molecular Biology", Vols. 1-111, Ausubel, Ed. (1997); Sambrook et al., "Molecular Cloning: A Laboratory Manual", 2nd Ed., Cold Spring Harbor Laboratory Press, Cold Spring Harbor, N.Y. (1989): "DNA Cloning: A Practical Approach", Vols. I and II, Glover, Ed. (1985); "Oligonucleotide Synthesis", Gait, Ed. (1984); "Nucleic Acid Hybridization", Hames & Higgins, Eds. (1985); "Transcription and Translation", Hames & Higgins, Eds. (1984); "Animal Cell Culture", Freshney, Ed. (1986); "Immobilized Cells and Enzymes", IRL Press (1986); Perbal, "A Practical Guide to Molecular Cloning"; the series, Methods in Enzymol., Academic Press, Inc. (1984); "Gene Transfer Vectors for Mammalian Cells", Miller and Calos, Eds., Cold Spring Harbor Laboratory, N Y (1987); and Methods in Enzymology, Vols. 154 and 155, Wu & Grossman, and Wu, Eds., respectively.

The standard control levels of the gene expression product, thus determined in the different control groups, would then be compared with the measured level of an gene expression product in a given patient. This gene expression product could be the characteristic mRNA associated with that particular genotype group or the polypeptide gene expression product of that genotype group. The patient could then be classified or assigned to a particular genotype group based on how similar the measured levels were compared to the control levels for a given group.

As one of skill in the art will understand, there will be a certain degree of uncertainty involved in making this determination. Therefore, the standard deviations of the control group levels would be used to make a probabilistic determination and the methods of this invention would be applicable over a wide range of probability based genotype group determinations. Thus, for example and not by way of limitation, in one embodiment, if the measured level of the gene expression product falls within 2.5 standard deviations of the mean of any of the control groups, then that individual may be assigned to that genotype group. In another embodiment if the measured level of the gene expression product falls within 2.0 standard deviations of the mean of any of the control groups then that individual may be assigned to that genotype group. In still another embodiment, if the measured level of the gene expression product falls within 1.5 standard deviations of the mean of any of the control groups then that individual may be assigned to that genotype group. In yet another embodiment, if the measured level of the gene expression product is 1.0 or less standard deviations of the mean of any of the control groups levels then that individual may be assigned to that genotype group.

Thus this process will allow the determining, with various degrees of probability, which group a specific patient should be place in and such assignment to a genotype group would then determine the risk category into which the individual should be placed.

Methods to detect and measure mRNA levels and levels of polypeptide gene expression products are well known in the art and include the use of nucleotide microarrays and polypeptide detection methods involving mass spectrometers and/or antibody detection and quantification techniques. See also, Human Molecular Genetics, 2nd Edition. Tom Strachan & Andrew, Read (John Wiley and Sons, Inc. Publication, N Y, 1999).

The therapeutic treatment of interest is administered to each individual in the population and each individual's response to the treatment is measured using one or more predetermined criteria. It is contemplated that in many cases, the population will exhibit a range of responses and that the investigator will choose the number of responder groups, e.g., low, medium and high, made up by the various responses. In addition, the gene for each individual in the population is genotyped and/or haplotyped, which may be done before or after administering the treatment.

It is to be understood that the methods of the invention described herein generally may further comprise the use of a kit according to the invention. Generally, the diagnostic methods of the invention may be performed ex-vivo, and such ex-vivo methods are specifically contemplated by the present invention. Also, where a method of the invention may include steps that may be practiced on the human or animal body, methods that only comprise those steps which are not practiced on the human or animal body are specifically contemplated by the present invention. In a preferred embodiment, such kit may comprise a DNA sample collecting means.

Thus the invention also encompasses kits for detecting the presence of a polypeptide or nucleic acid corresponding to a marker of the invention in a biological sample, e.g., any body fluid including, but not limited to, serum, plasma, lymph, cystic fluid, urine, stool, csf, acitic fluid or blood and including biopsy samples of body tissue. For example, the kit can comprise a labelled compound or agent capable of detecting a polypeptide or an mRNA encoding a polypeptide corresponding to a marker of the invention in a biological sample and means for determining the amount of the polypeptide or mRNA in the sample, e.g., an antibody which binds the polypeptide or an oligonucleotide probe which binds to DNA or mRNA encoding the polypeptide. Kits can also include instructions for interpreting the results obtained using the kit.

For oligonucleotide-based kits, the kit can comprise, e.g., 1) an oligonucleotide, e.g., a detectably-labelled oligonucleotide, which hybridizes to a nucleic acid sequence encoding a polypeptide corresponding to a marker of the invention; or 2) a pair of primers useful for amplifying a nucleic acid molecule corresponding to a marker of the invention.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit.

The kits of the invention may contain a written product on or in the kit container. The written product describes how to use the reagents contained in the kit to determine whether a patient will experience hepatotoxicity during drug treatment. In several embodiments, the use of the reagents can be according to the methods of the invention. In one embodiment, the reagents are primer pairs for performing PCR analysis of genetic wild type.

The invention, having been described in summary and in detail, is illustrated but not limited by the Examples below that provide pharmaceutically acceptable formulation of TH-4000 of the present invention and demonstrate the efficacy of TH-4000 administration to treat cancer in accordance with the present methods.

EXAMPLES

General
Materials:

HCC827 cell lines are available from ATCC (CRL-2868). PC9 cell lines are available from RIKEN Bio Resource Center, Japan. TH-4000 can be synthesized and separated from unwanted reaction material as described in PCT Pat. App. Pub. No. WO 2011/028135 (incorporated herein by reference). Erlotinib (SN 31254) was provided by the Auckland Cancer Society Research Centre, Medicinal Chemistry Department. (2-hydroxylpropyl)-β-cyclodextrin is available from Sigma Aldrich (Cat#778966-500G). Poly(ethylene glycol) 400 (PEG-400) is available from Sigma Aldrich (Cat#P3265-1KG). Dimethyl Sulfoxide (DMSO) is available from ECP Ltd, New Zealand (Cat#2200.1-500 ml). Water for injection (WFI) is available from DEMO S.A. Pharmaceutical Industry, Greece Example 1. A Unit Dose Formulation of TH-4000

TH-4000 was formulated in ultra pure water purified by distillation or reverse osmosis "WFI" and 20% 2-hydroxylpropyl-β-cyclodextrin to yield a unit dose form of TH-4000.

Example 2. Demonstration of TH-4000's Efficacy in Killing Hypoxic Tumor Cells, Specifically EGFR Mutation-Positive Non-Small Cell Lung Cancer at Clinically Relevant Human Equivalent Doses HCC827 and PC9 cells are NSCLC cell lines which harbor an exon 19 deletion mutation in the tyrosine kinase domain of EGFR. HCC827 is homozygous with regards to the mutant EGFR (100% mutant alleles) whereas a proportion of alleles in PC9 cells contain wild-type EGFR (87% mutant and 13% wild type) and is thus heterozygous in this regard. This example assessed the relative efficacy of TH-4000 and erlotinib at clinically achievable dose levels in two genetic backgrounds using in vivo xenograft models of mutant EGFR driven lung cancer.

HCC827 and PC9 human non-small cell lung cancer (NSCLC) cells were prepared in medium. Then 10 million cells per inoculum were injected subcutaneously in 5-8 week old female NIH-III nude mice (18-24 g). HCC827 tumors were recruited at ~200 mm$^3$ and PC9 tumors were recruited at ~400 mm$^3$. When the tumors reached the desired volumes, the mice were randomly assigned to groups A-E and treated as detailed in Table 1 below:

TABLE 1

| Group | Treatment A | Schedule/route | N |
|---|---|---|---|
| A | Vehicle (β-cyclodextrin) | Q3dx8, i.p. | 5-6 |
| B | Erlotinib (10 mg/kg) | Qdx21, p.o. | 5-6 |
| C | TH-4000 (30 mg/kg) | Q3dx8, i.p. | 5-6 |
| D | TH-4000 (15 mg/kg) | Q3dx8, i.p. | 5-6 |
| E | TH-4000 (7.5 mg/kg) | Q3dx8, i.p. | 5-6 |

TH-4000 was formulated as in Example 1. Erlotinib was formulated in a solution of 5% DMSO, 40% PEG-400 in 40% 2-hydroxylpropyl-β-cyclodextrin. Body weight was recorded every 3 days or prior to dosing and the length and width of subcutaneous tumors were measured with electronic calipers every 3 days and volume calculated according to the formula for a prolate ellipsoid (π/6×length×width×width). All other clinical signs were recorded.

The results are described below. When mice bearing established subcutaneous tumors were treated with erlotinib (10 mg/kg, daily oral), which provides average blood exposure (AUC$_{inf}$ 20,000 ng*h/ml) equivalent to the FDA approved human dose (150 mg daily oral), only the homozygous EGFR mutant containing tumor can be successfully controlled (FIGS. 1-2, tables 2-4).

TABLE 2

(corresponding to HCC827 tumor in FIG. 1).

| Group | Median time to RTV4 | % TGD relative to control |
|---|---|---|
| Control | 45 days | — |
| Erlotinib | 114 days | 153% |
| TH-4000 (30 mg/kg) | >150 days | >233% |

TABLE 2-continued (corresponding to HCC827 tumor in FIG. 1).

| Group | Median time to RTV4 | % TGD relative to control |
|---|---|---|
| TH-4000 (15 mg/kg) | >150 days | >233% |
| TH-4000 (7.5 mg/kg) | 144 days | 220% |

TABLE 3

(corresponding to PC9 tumor in FIG. 2).

| Group | Median time to RTV4 | % TGD relative to control |
|---|---|---|
| Control | 30 days | — |
| Erlotinib | 39 days | 30% |
| TH-4000 (30 mg/kg) | 132 days | 340% |
| TH-4000 (15 mg/kg) | 99 days | 230% |
| TH-4000 (7.5 mg/kg) | 90 days | 200% |

TABLE 4

(corresponding to PC9 tumor in FIG. 2).

| Reference | Comparison | Log Rank test | Median Survival gain (days) |
|---|---|---|---|
| Control | 10 mg/kg Erlotinib | P = 0.07 | 9 |
| Control | 7.5 mg/kg TH-4000 | P = 0.007 | 60 |
| Control | 15 mg/kg TH-4000 | P = 0.0007 | 69 |
| Control | 30 mg/kg TH-4000 | P = 0.007 | 102 |
| Erlotinib | 7.5 mg/kg TH-4000 | P = 0.01 | 51 |
| Erlotinib | 15 mg/kg TH-4000 | P = 0.001 | 60 |
| Erlotinib | 30 mg/kg TH-4000 | P = 0.01 | 93 |

In contrast, TH-4000 is highly active in both the homozygous and heterozygous tumor setting, at plasma concentrations which are only 10%-20% of those obtained at the maximum safe dose of TH-4000 (150 mg/m$^2$) in phase I clinical trial. Growth delay of TH-4000 in HCC827 xenografts was evaluated at 3 doses—30, 15 and 7.5 mg/kg (q3d×8). The regression of all HCC827 tumors at both dose levels; CR of 100%. 92% of tumors failed to grow within 90 days. Only mild body weight loss observed in the two TH-4000-treated groups (1.1%-2.5%).

These results provide evidence that hypoxia-dependent metabolism provides tumor selective release of EGFR TKI in hypoxic tumor cells. The high local concentrations provide the necessary therapeutic index to silence wild type EGFR signaling in the hypoxic tumor compartment. These results also establish the efficacy of TH-4000 in a NSCLC model harboring an exon 19 deletion mutation. Thus, EGFR NSCLC and may overcome hypoxia-induced resistance to erlotinib at plasma exposures readily achieved in human subjects. TH-4000 exhibits greater activity compared with erlotinib and afatinib in a WT EGFR driven xenograft model and has good activity in a HER2-amplified xenograft model at plasma exposures readily achieved in human subjects.

Example 3. Demonstration of the Pharmacokinetic (PK) and Pharmacodynamic (PD) Profile of TH-4000 and TH-4000E in PC-9 Tumors Pharmacokinetic and pharmacodynamic studies were performed in NIH-III mice bearing PC-9 tumours, when dosed ip with 15 mg/kg of TH-4000. Mice were inoculated with PC-9 cells (~8×10$^6$ cells per mouse, 42 mice in total). TH-4000 was formulated as above and mice were euthanized and 3 tumors were excised at the following time points after TH-4000 administration: 0.5 hrs., 3 hrs., 12 hrs., 24 hrs., 48 hrs., 72 hrs., 96 hrs., 120 hrs., 144 hrs and 168 hrs. The whole tumors were snap frozen (with liquid nitrogen) and bio-pulverised. The tumors were measured every day until collection to correlate the growth kinetics of the tumor to target shutdown. Following bio-pulverisation, half of the bio-pulverised tumor was processed for measurement of TH-4000 and TH-4000E concentrations by LC-MS/MS. The other half of the tumor was processed for protein extraction and Western blotting to determine level of pEGFR and total protein (EGFR, α-tubulin).

For LC-MS/MS, 4 volumes of ice cold acetonitrile (containing 0.5 µM of D6-TH-4000 & TH-4000E) were added to the tumor samples. Samples were spun at 13,000 rpm for 5 min. and 40 µL of the supernatant was taken. To the supernant, 80 µL of 0.01% FA-Water was added and the sample was mixed. 10 µL of this sample was injected for analysis. Mass spectrometric detection was carried out using an Agilent 6410 triple quadrupole mass spectrometer equipped with a multimode ionization (MMI) source. The mass spectrometer was operated in electrospray positive ionization mode using multiple reaction monitoring (MRM). Agilent MassHunter software (v.4.04.00) was used for data acquisition and chromatographic peak integration.

For Western blotting of the tumor samples, the pulverized tissue was collected and quickly transferred to an Eppendorf tube embedded in dry ice. Once all samples were bio-pulverized, they were quickly weighed, making notes of the tissue weight while keeping the tube in dry ice. Under a fume hood, a volume of cold 1× Laemmli buffer+protease inhibitor (dil 1:100) corresponding to 10× the weight of the sample was added and the samples were transferred to wet ice. The samples were vortexed for 1 minute, checking that the disintegrated tissue was macroscopically solubilized. The sample was incubated for 10 minutes at 70° C. with shaking at 300 RPM in a EppendorfThermomixer Compact. Any residual undissolved tissue was sedimented by centrifugation at 13,000×g for 5 minutes at room temperature. A 20 ml aliquot was set aside for measuring the protein concentration using a Bio-Rad protein (Bradford) Assay. The rest of the sample was frozen at −20° C. The results are tabulated below.

TABLE 5

(corresponding to FIG. 3).

| PK parameter | TH-4000) ± SE | TH-4000-TKI ± SE |
|---|---|---|
| $C_{max\,obs}$ (ng/mL) | 11717 ± 1048 | 47 ± 3.6 |
| $C_{max\,pred}$ (ng/mL) | 29797 ± 74 | 50 |
| $AUC_{0-\infty}$ (ng*h/mL) | 15960 ± 13 | 106 |
| $T_{1/2}$ (h) | 0.37 ± 0.00 | 1.28 |

Western blotting was also used to detect inhibition of EGFR autophosphorylation (Y1068) by erlotinib (0.1-10 uM). HCC827 and PC9 cell cultures are set up from log-phase passage flasks. Cells are seeded into 6-well plates at a density of 1 million cells per well and left for 48 hours under normoxic or hypoxic (1% $O_2$) conditions. Erlotinib drug stock solutions are diluted in media to achieve final concentrations (as shown in the figure) in each well. Following 3 hours of drug exposure, cells are washed in ice-cold PBS and lysed on ice for 30 minutes with radioimmunoprecipitation assay (RIPA) buffer containing sodium orthovanadate and sodium fluoride at final concentrations of 1 mM each. Cell debris is pelleted out by centrifugation (13,000 rpm for 2 minutes). Protein concentrations in each sample are determined by a bicinchoninic acid (BCA) assay. Equivalent amounts of protein (10 pig) are denatured (98° C. for 5 minutes) and loaded onto 4-20% Tris-Glycine protein gels for protein separation. Following transfer to a nitrocellulose membrane, each membrane was blocked with 5% bovine serum albumin (in Tris-buffered saline) for 1 hour. Primary antibody (rabbit, polyclonal) against pEGFR (Y1068) was added overnight at a dilution of 1:2000 in 5% bovine serum albumin (with Tris-buffered saline). Excess primary antibody in each membrane was washed off with Tris-buffered saline. Secondary antibody (goat anti-rabbit) was added to each membrane at a dilution of 1:5000 for 2 hours. For protein detection, the membrane was washed in Tris-buffered saline to remove excess secondary antibody and chemiluminescent substrate added (Pierce Supersignal West Pico Chemiluminescent Substrate) for 5 minutes. The membrane was viewed using a Fujifilm LAS 4000 imager. This in vitro evidence indicated a role for hypoxia exposure (1% $O_2$) in the resistance to erlotinib in the heterozygous PC-9 cell line (see FIGS. 6 and 7).

Single-dose administration of 15 mg/kg TH-4000 in nude mice achieved a plasma AUC equivalent to 32 mg/m² in human subjects, one fifth of the maximum safe dose defined in Phase I trial (MTD=150 mg/m²/week; NCT01631279). TH-4000 cleared rapidly from mouse plasma (T½=0.37 h) but had durable residency in PC9 tumors (T/2=39 h), releasing TKI above efficacious levels for 7 days (T½β=84 h). Consistent with these PK properties, global shutdown of EGFR signaling was profound and durable, with no recovery by day 7. To confirm mechanism of action we prepared a chem-bio tool (CBT) that mirrored the physicochemical properties of TH-4000 but was designed not to release TKI following 1e-reduction. TH-4000 was metabolized efficiently under anoxia using a panel of human NSCLC cell lines (rate of TKI release 0.4-2.1 nmol/hr/$10^6$ cells), a process that was inhibited by O2 (TKI<0.002 nmol/hr/$10^6$ cells). CBT was metabolically inert under all conditions. Cellular anti-proliferative and receptor phosphorylation assays demonstrated a 14-80 fold deactivation of TH-4000 relative to parent TKI whilst CBT was deactivated irrespective of oxygen status. In vivo, hyperbaric 02 breathing suppressed PC9 tumor production of TKI from TH-4000 by >80% (538 vs 99 nmol/kg; p<0.01) whereas CBT failed to release significant TKI (<1%). Collectively these data indicate TH-4000 has a unique hypoxia-activated mechanism, is active in heterozygous models of mutant EGFR NSCLC and may overcome hypoxia induced resistance to erlotinib at plasma exposures readily achieved in human subjects.

Example 4. Demonstration of TH-4000 Efficacy for Treatment of Cancer in Combination with Erlotinib in PC-9 Xenografts To further examine the therapeutic advantage of TH-4000 in the heterozygous (mutant/wild type) tumor setting, PC9 xenografts were treated with erlotinib (10 mg/kg, daily oral), for 14 days before introduction of once weekly TH-4000 (15 mg/kg). In addition PC9 xenografts were treated with erlotinib (10 mg/kg, daily oral) as a single agent, or TH-4000 (3, 7.5 and 15 mg/kg, i.p.) as a single agent, or with erlotinib and TH-4000 in combination at the above stated doses and routes of administration.

TH-4000 and erlotinib were formulated as follows: TH-4000 in WFI containing 20% 2-hydroxylpropyl-β-cyclodextrin; Erlotinib in a solution of 5% DMSO, 40% PEG-400 in 40% 2-hydroxylpropyl-β-cyclodextrin. PC9 tumor cells were inoculated subcutaneously in 5-8 wk female NIH-III nude mice (17-22 g). Tumors were grown to ~400 mm³. When tumors were 400 mm³ mice were randomly assigned to groups A-J and treated as detailed below:

| Group | Treatment A | Schedule/route | Treatment B | Schedule/route | N |
|---|---|---|---|---|---|
| A | Vehicle | | | | 5 |
| B | Erlotinib (10 mg/kg) | Qdx21, p.o. | | | 5 |
| C | TH-4000 (15 mg/kg) | Qwx4, i.p. | | | 5 |
| D | TH-4000 (7.5 mg/kg) | Qwx4, i.p. | | | 5 |
| E | TH-4000 (3 mg/kg) | Qwx4, i.p. | | | 5 |
| F | Erlotinib (10 mg/kg) | Qdx21, p.o. | TH-4000 (15 mg/kg) | Qwx4, i.p. | 5 |
| G | Erlotinib (10 mg/kg) | Qdx21, p.o. | TH-4000 (7.5 mg/kg) | Qwx4, i.p. | 5 |
| H | Erlotinib (10 mg/kg) | Qdx21, p.o. | TH-4000 (3 mg/kg) | Qwx4, i.p. | 5 |
| J | Erlotinib (10 mg/kg) | Qdx21, p.o. | 14-days-TH-4000 (15 mg/kg) | Qwx3, i.p. | 5 |

The length and width of subcutaneous tumors were measured with electronic calipers every 3 days and volume calculated according to the formula for a prolate ellipsoid (π/6×length×width×width). Body weight was recorded every 3 days or prior to dosing. All other clinical signs were recorded.

Administration of TH-4000 provided immediate tumor shrinkage. In PC9 cells, the efficacy of TH-4000 across 3 doses (3, 7.5, & 15 mg/kg; qwx4) was demonstrated. Tumor regressions were seen for all mice dosed with 7.5 & 15 mg/kg of TH-4000 (FIG. 11-12). Stable disease was achieved for mice dosed with 3 mg/kg of TH-4000 (FIG. 13). The reduction in PC9 tumor volume beginning at day 14 following administration of 15 mg/kg of TH-4000 was not associated with any signs of toxicity as indicated by the absence of body weight loss in the murine host (FIG. 14). However, erlotinib only achieved stable disease over period of dosing (21 days). While not being bound by theory, these observations are consistent with the necessity to silence both wild type EGFR signaling in the hypoxic compartment of the tumor in concert with mutant EGFR signaling throughout the tumor. They also demonstrate the presence of a significant therapeutic index for TH-4000 in the heterozygous EGFR tumor setting.

In addition, Western blotting data (FIG. 6-8) comparing the activity of AZD9291 in either a homozygous or heterozygous cell line context under aerobic or hypoxic conditions is consistent with resistance to AZD9291 in the presence of tumor hypoxia in the heterozygous EGFR setting as was seen for erlotinib.

As shown above, TH-4000 provides marked regressions in erlotinib-resistant preclinical NSCLC models at doses readily achieved in human trials.

Example 5. Demonstration of TH-4000 Efficacy in Xenograft Model of HER2 Amplified Gastric Cancer Antitumor activity of erlotinib, afatinib and TH-4000 were compared in the WT EGFR expressing A431 xenograft at clinically relevant dose levels and schedules. NIH-III mice were administered 30 mg/kg TH-4000 (ip) to achieve an AUC of 60.2 ug*hr/mL, dose-equivalent to 104 mg/m2 in human subjects for unbound TH-4000. Daily oral erlotinib or afatinib were unable to prevent tumor progression. Only TH-4000 (30 mg/kg, ip) either once weekly (Qwx4) or twice weekly (Q3dx8) was able to control the WT EGFR driven A431 tumor xenografts, with 100% tumor regression. All treatments were well tolerated with <5% body weight change. As can be seen in FIGS. 15 and 16, TH-4000 is active against the HER2-positive NCI-N87 gastric tumor xenograft with minimal (<5%) body weight loss.

Example 6. Anti-Proliferative Assay of Various EGFR-Targeted Agents in FaDu Cells This study aimed to determine the sensitivity of FaDu cells to various EGFR-targeted agents following a five day exposure
Agents Evaluated
The agents evaluated in this study were as follows:

| Study number: Title | In vitro antiproliferalive activity of Cetuximab, Eriotinib, TH-4000 and TH-4000E under aerobic conditions using human hypopharnygeal FaDu cells |
|---|---|
| Agents evaluated | Cetuximab (IMC-C225)<br>TH-4000<br>TH-4000E<br>Erlotinib (OSI-774) |

Cell Line
This study focuses on the human hypopharnygeal cell line, FaDu (ATCC #HTB-43). FaDu cells were grown in αMEM culture medium supplemented with 5% FBS, without routine use of antibiotics (P/S). Cultures were re-established from authenticated frozen stocks in liquid nitrogen at either >24 passages or >90 days in culture (whichever came first). The frozen cell stocks were confirmed to be free of *mycoplasma* using a PCR-ELIZA kit (Roche Diagnostics GmbH, Mannheim, Germany).
Anti-Proliferative Assay
FaDu cells were seeded (1500 cells/well in αMEM culture media with 5% FCS) in 96 well plates and allowed to settle overnight at 21% $O_2$. Cells were then treated with ten serial dilutions (3-fold) of each test compound. Cells were left to grow in a humidified incubator (5% $CO_2$, 37° C.) for 5 days. Cells were then fixed with 40% trichloroacetic acid for 1 h at 4° C. Cells were then stained for Sulforhodamine B (SRB) expression. Cell density was determined by using the Biotek ELx808 Absorbance Microplate Reader. IC50 values were deduced by extrapolation of the value required to reduce the cell density by 50%.
TH-4000E is a 150-fold more dose-potent than cetuximab in a five day anti-proliferative assay. Therefore cetuximab-resistant Head/Neck cancer may retain sensitivity to TH-4000E. The anti-proliferative activity of erlotinib is modestly superior to cetuximab (IC50 values differ 2-fold). Therefore FaDu cells display a relative resistance to both cetuximab and erlotinib. TH-4000E displays an 80-fold lower IC50 value then erlotinib. Therefore, erlotinib-resistant cells may retain sensitivity to TH-4000E. The anti-proliferative activity of the prodrug TH-4000 was 13-fold less than TH-4000E (effector) in FaDu cells exposed continuously for 5 days indicating deactivation of the prodrug relative to the effector.

In FIG. 17, IC50 values represent concentration of agent required to reduce proliferation by 50% relative to untreated controls. IC50 values are mean±standard error of >3 independent experiments. FaDu cells as relatively resistant to the clinically approved EGFR inhibitors cetuximab and erlotinib. Despite resistance to cetuximab and erlotinib, FaDu cells display marked sensitivity to TH-4000E. The produg TH-4000 is deactivated relative to TH-4000E.

Example 7. Anti-Proliferative Assay of Various EGFR-Targeted Agents in Fadu Cells This study aimed to determine how anoxic exposure alters the sensitivity of FaDu cells to various EGFR-targeted agents.
Agents Evaluated
The agents evaluated in this study were as follows:

| Study number: Title | In vitro antiproliferative activity of Cetuximab, Erlotinib, TH-4000 and TH-4000E under aerobic and anoxic conditions using human hypopharnygeal FaDu cells |
|---|---|
| Agents evaluated | Cetuximab (IMC-C225)<br>TH-4000<br>TH-4000E<br>Erlotinib (OSI-774, SN31254) |

Cell Line
This study focuses on the human hypopharnygeal cell line, FaDu (ATCC #HTB-43). FaDu cells were grown in αMEM culture medium supplemented with 5% FBS, without routine use of antibiotics (P/S). Cultures were re-established from authenticated frozen stocks in liquid nitrogen at either >24 passages or >90 days in culture (whichever came first). The frozen cell stocks were confirmed to be free of *mycoplasma* using a PCR-ELIZA kit (Roche Diagnostics GmbH, Mannheim, Germany).
Anti-Proliferative Assay
Monolayers of FaDu cells were harvested by trypsinisation and counted using a hemocytometer. For the oxic assays, cells were seeded (1500 cells/well) in 96 well plates and allowed to settle for 2 hours in a humidified incubator (37 C/5% $CO_2$). Cells were then treated with ten serial dilutions (3-fold) of each test compound for 24 hours. For the anoxic plates, all supplies were pre-equilibrated for at least 72 hours in a $H_2$/palladium-catalyst anaerobic chamber (Bactron, Shellab) to remove any residual oxygen. On the experiment day, cells were centrifuged (1000 rpm, 5 min) to pellet cells. The media was aspirated. The pellet was then taken into the anaerobic chamber and diluted in anoxia-equilibrated media (αMEM culture media, 5% FCS, 0.2 mmol/L 2'-deoxycytidine, 10 mmol/L glucose) to achieve the appropriate cell density. Cells were seeded in identical conditions to the oxic plates. Once seeded, cells were left to settle in a humidified incubator (37 C) within the anaerobic chamber for 2 hours. Anoxic plates were similarly treated with ten serial dilutions (3-fold) of each test compound. Anoxic plates were removed from the anaerobic chamber four hours after drug addition, and placed into a humidified incubator (37 C/5% $CO_2$) for a further 20 hours. After a total of 24 hours of drug exposure, both the oxic and anoxic plates were washed three times in fresh media (αMEM+5% FCS+ P/S). Cells were left to grow for a total of 5 days. After which, cells were fixed with 40% trichloroacetic acid for 1 hour at 4° C. Plates were then stained for Sulforhodamine B (SRB) expression. Cell density was determined by using the Biotek ELx808 Absorbance Microplate Reader. IC50 values were deduced by interpolation of the value required to reduce the cell density by 50%.

Anoxic conditions reduced the cetuximab sensitivity of FaDu cells. The anoxic IC50 value was 4-fold higher than the oxic equivalent. Therefore anoxic exposure appears to promote cetuximab resistance in FaDu cells, possibly due to enhanced EGF receptor intracellular sequestration (membrane internalization). The anti-proliferative activity of erlotinib was modestly superior to cetuximab (3-fold more dose-potent by IC50 value) under aerobic exposure conditions. Erlotinib sensitivity of FaDu cells was unaffected by anoxia. Following a period of anoxic exposure, the erlotinib IC50 value was 13-fold lower than cetuximab, reflecting alterations in cetuximab sensitivity. Under anoxic exposure conditions, TH-4000 was 3000-fold more dose-potent than cetuximab (relative IC50 value). Therefore, Head/Neck cells rendered resistant to cetuximab through anoxia-dependent mechanisms may retain sensitivity to TH-4000. TH-4000E is an irreversible HER1/2/4 inhibitor that is released under hypoxic conditions from its cognate prodrug TH-4000. TH-4000E displays a 1400-fold greater dose-potency then erlotinib (as measured by IC50 value). Therefore, erlotinib-resistant cells may retain sensitivity to TH-4000E. Following a period of anoxic exposure, TH-4000 was 244-fold more dose-potent than erlotinib as determined by change in IC50 value. Therefore, erlotinib-resistant Head/Neck cells may retain sensitivity to TH-4000. TH-4000 is a hypoxia-activated prodrug of TH-4000E, an irreversible HER1/2/4 inhibitor. In air, the anti-proliferative activity of the effector (TH-4000E) was superior to the prodrug (TH-4000). Therefore the prodrug TH-4000 is deactivated 62-fold relative to its cognate effector TH-4000E. TH-4000 displayed hypoxia selective antiproliferative activity in FaDu cells, being 15-fold more active following 4 h of anoxia.

Figure 18:
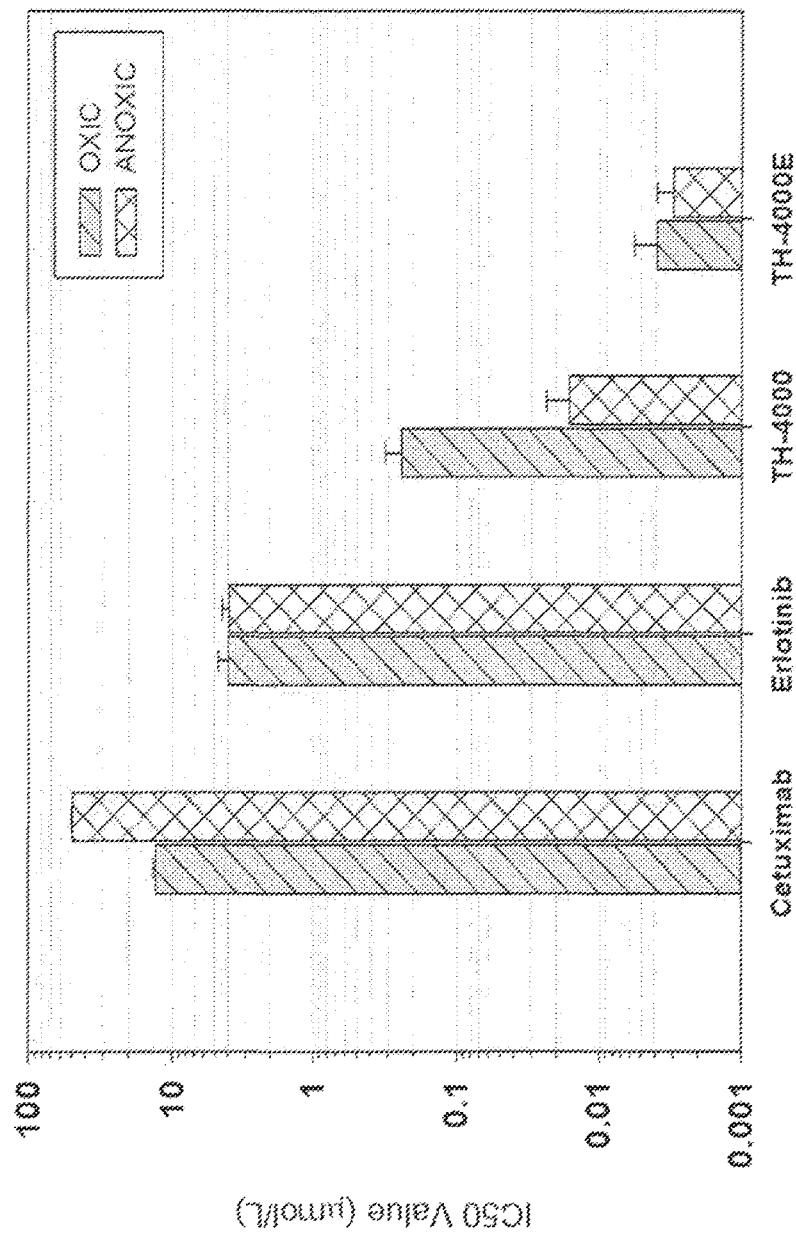
FIG. 18 shows antiproliferative activity of cetuximab, erlotinib, TH-4000 and TH-4000E in the human hypopharnygeal cell line FaDu.
Figure 19:
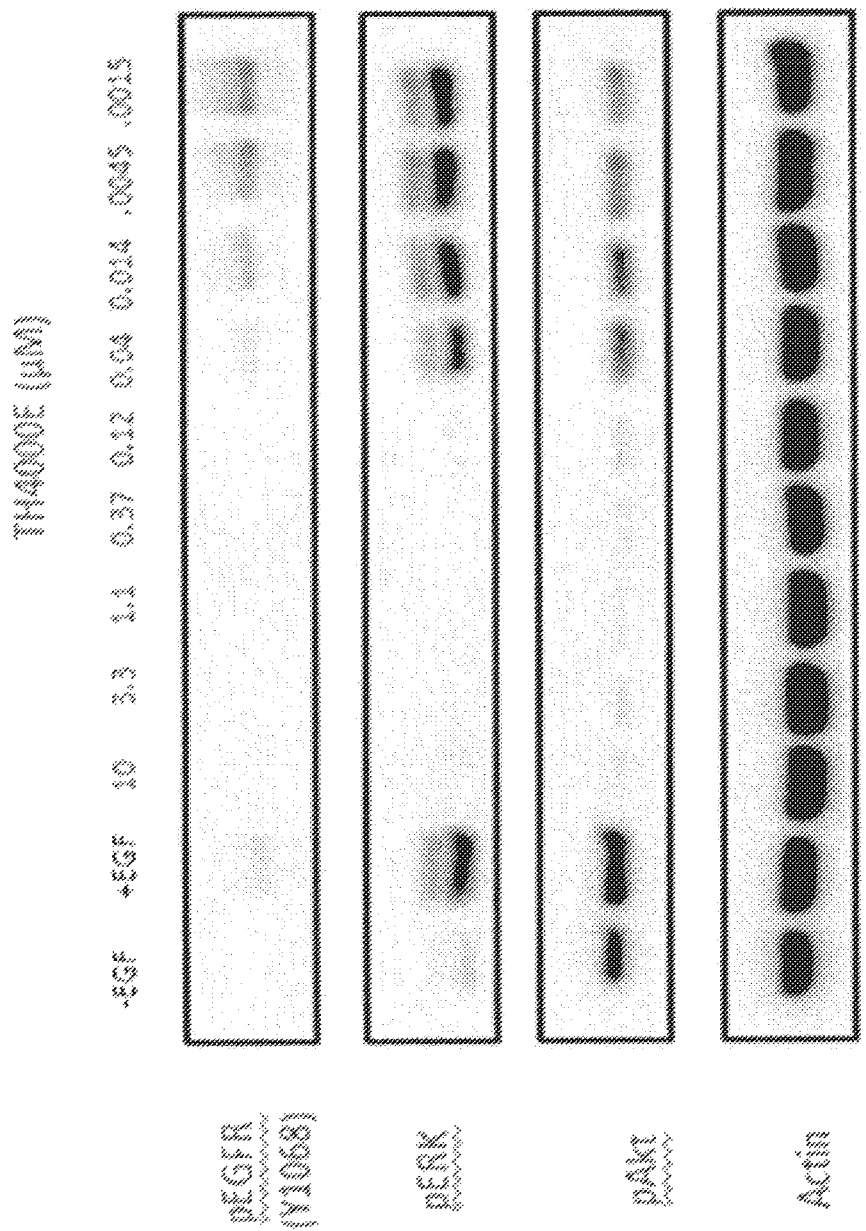
FIG. 19 shows expression of various members of the EGFR signaling axis following treatment with gradient TH-4000E concentrations.
Figure 20:
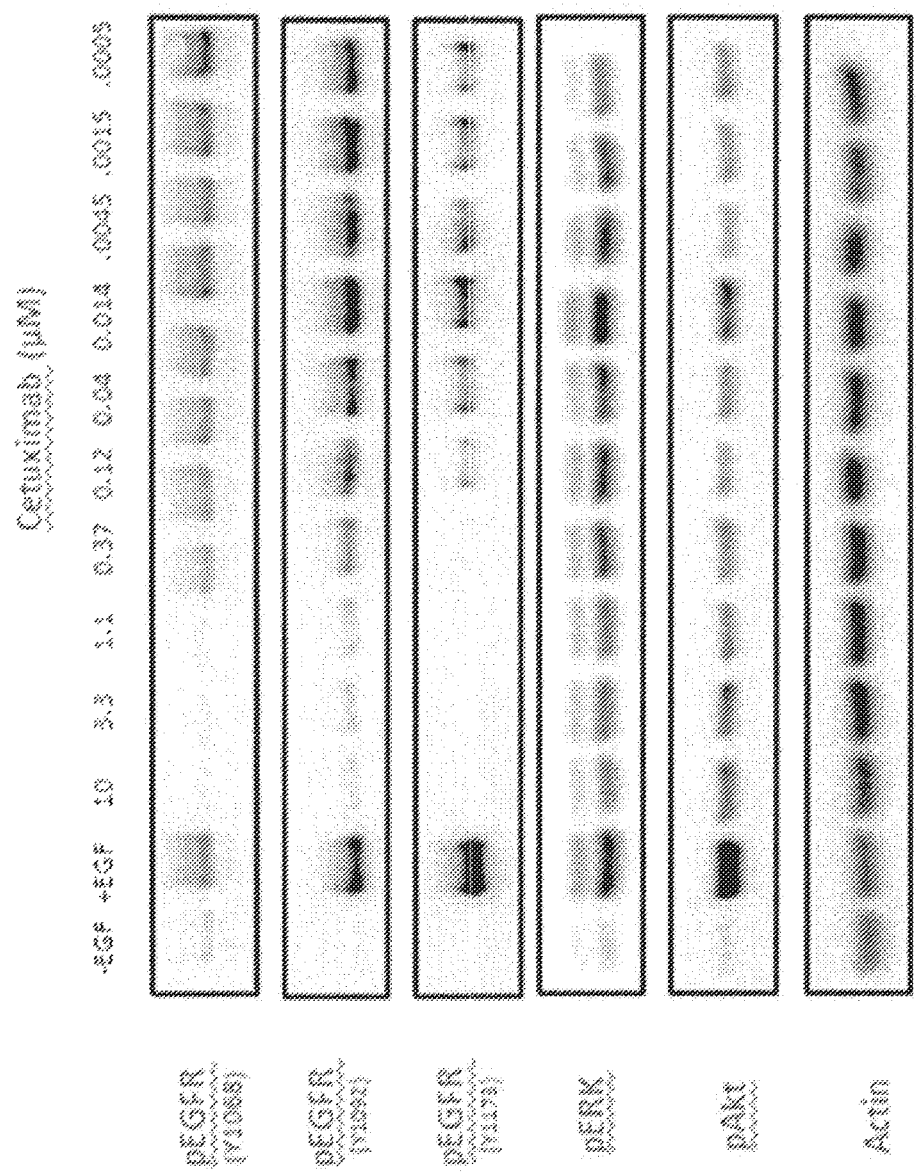
FIG. 20 shows expression of various members of the EGFR signaling axis following treatment with gradient cetuximab concentrations.
Figure 21:
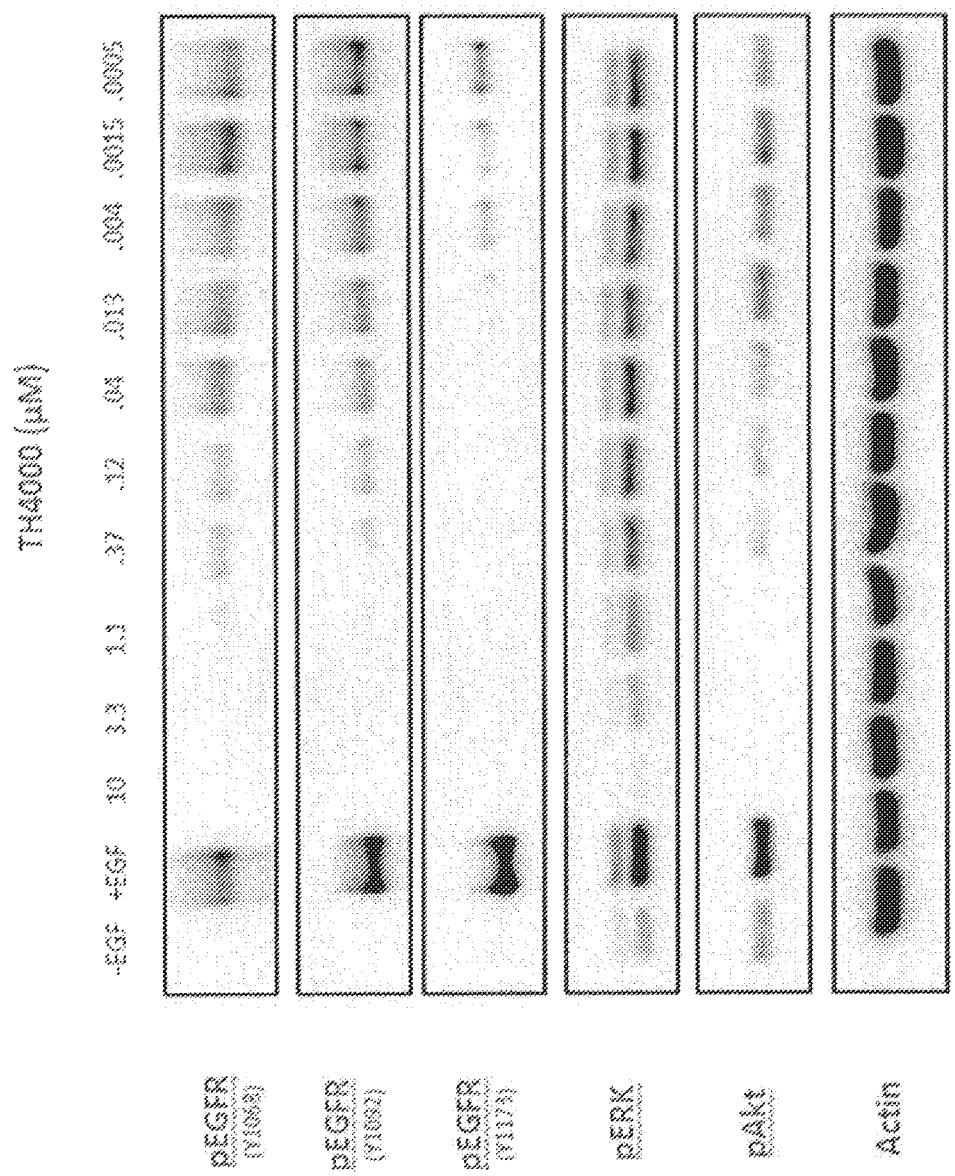
FIG. 21 shows expression of various members of the EGFR signaling axis following treatment with gradient TH-4000 concentrations.
Figure 22:
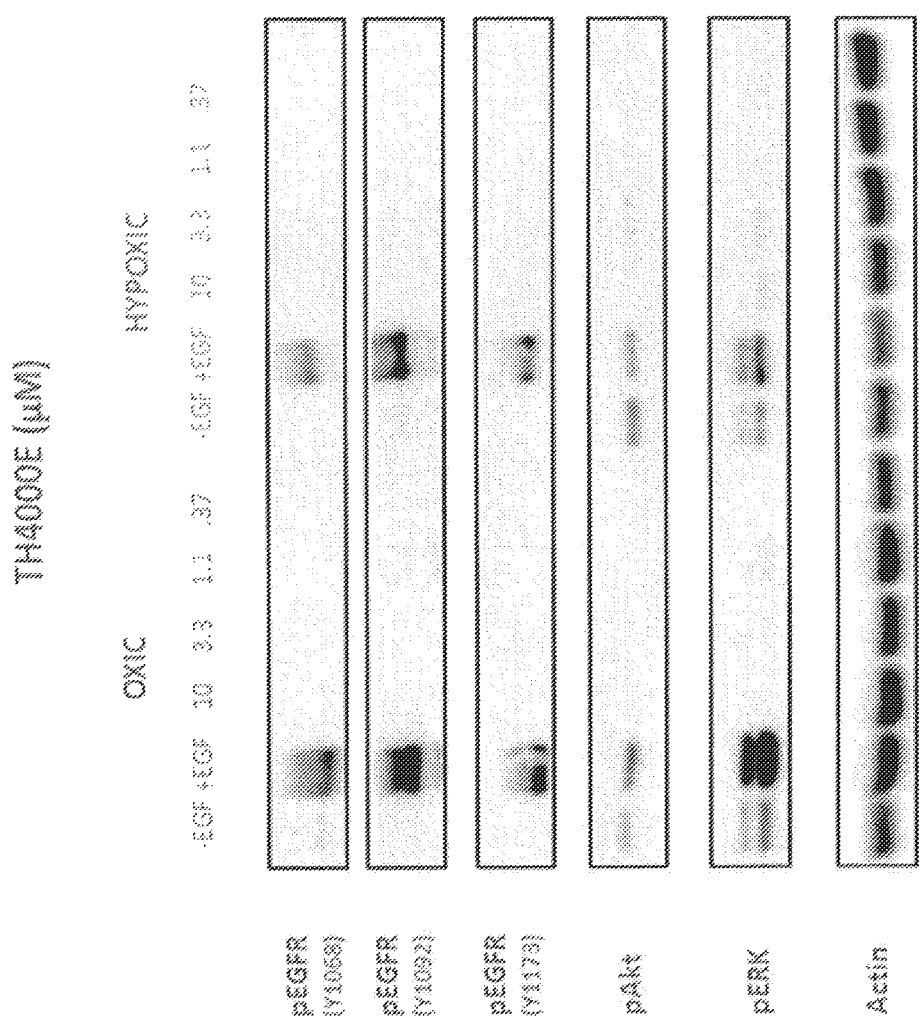
FIG. 22 shows EGFR expression following exposure to TH-4000E at various concentrations in oxia and hypoxia-preconditioned (48 h) FaDu cells.
Figure 23:
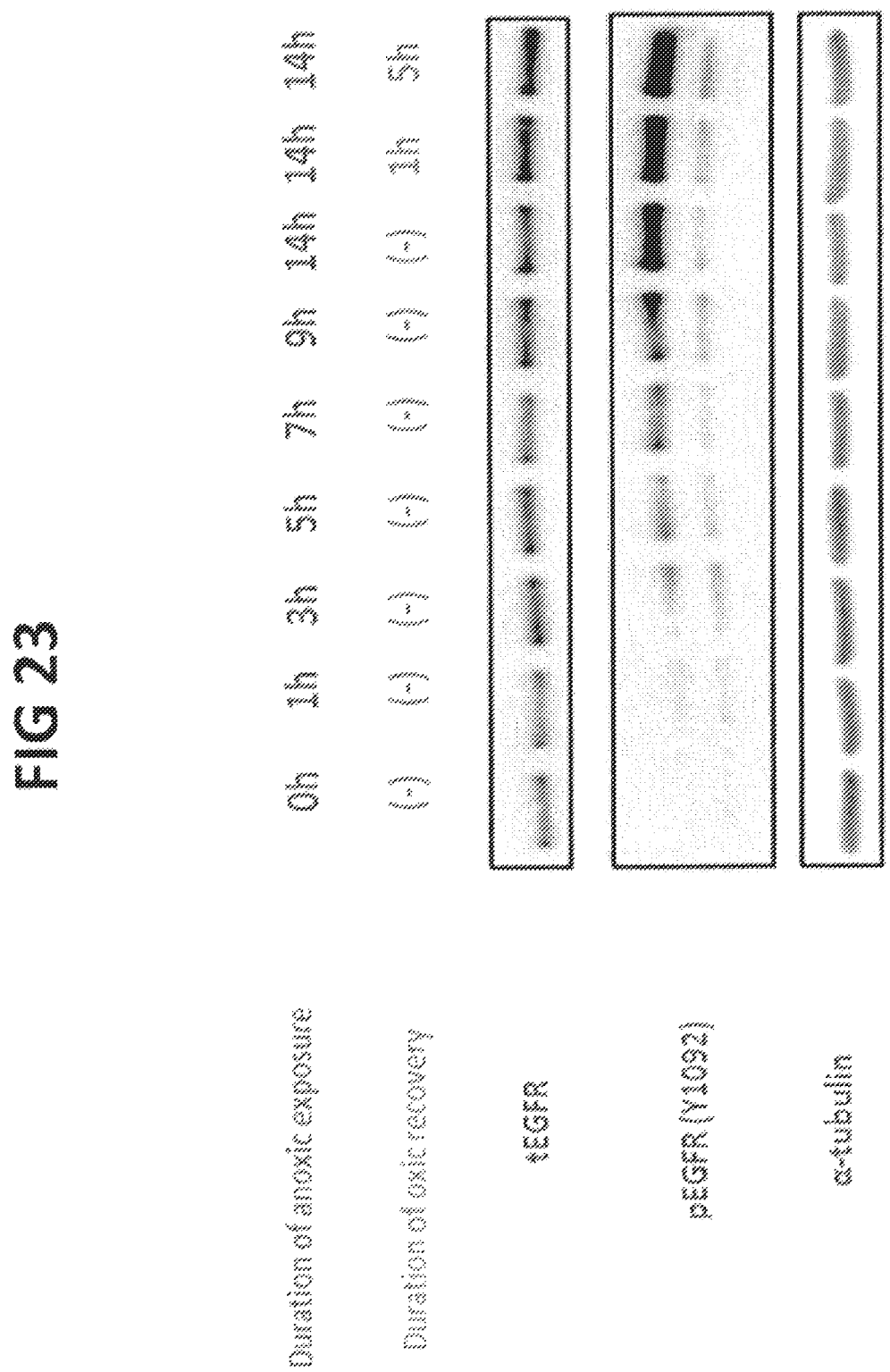
FIG. 23 shows EGFR expression following a duration of anoxic exposure with/without a period of oxic recovery.
Figure 24:
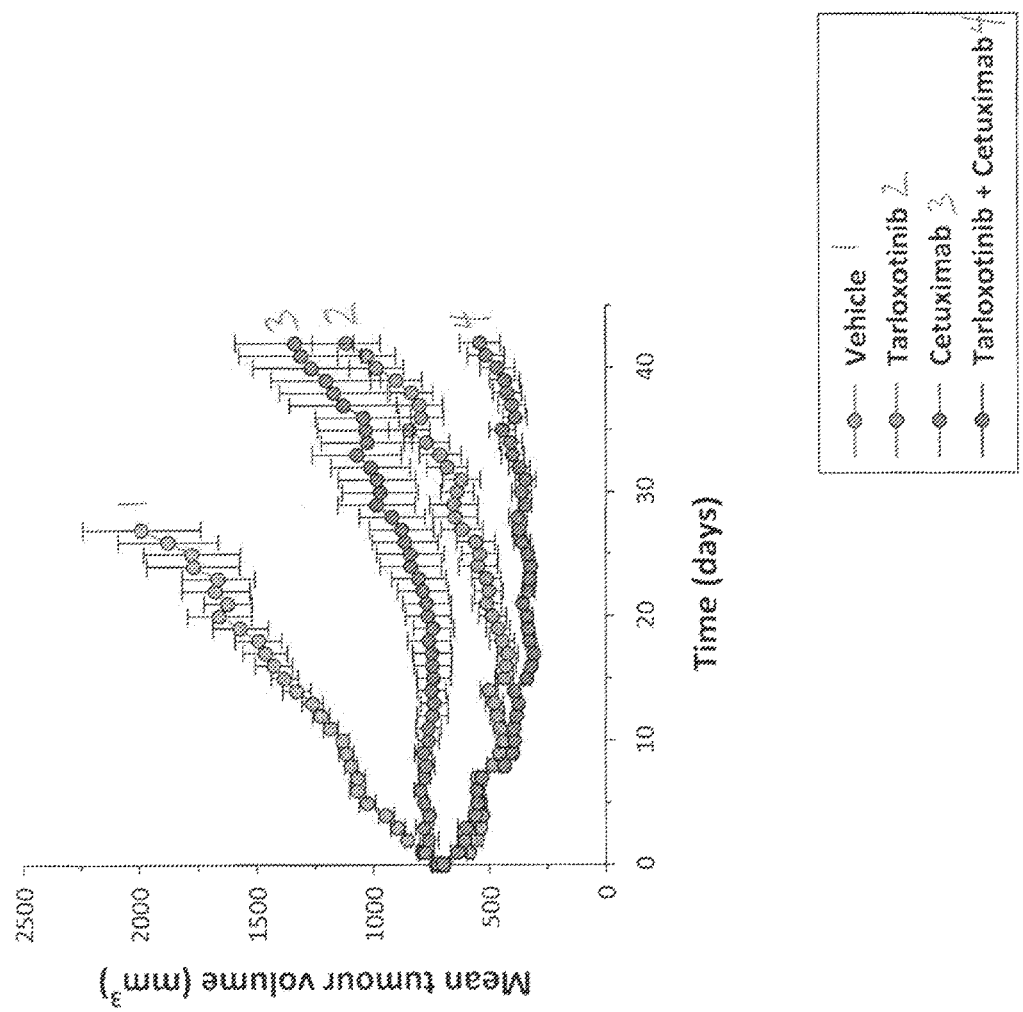
FIG. 24: Average tumor volume (±S.E.M.) of H125 tumors treated with vehicle control (qw×6), 48 mg/kg tarloxotinib (qw×6), 0.25 mg/mouse cetuximab (q3d×14) and the combination of tarloxotinib & cetuximab.
Figure 25:
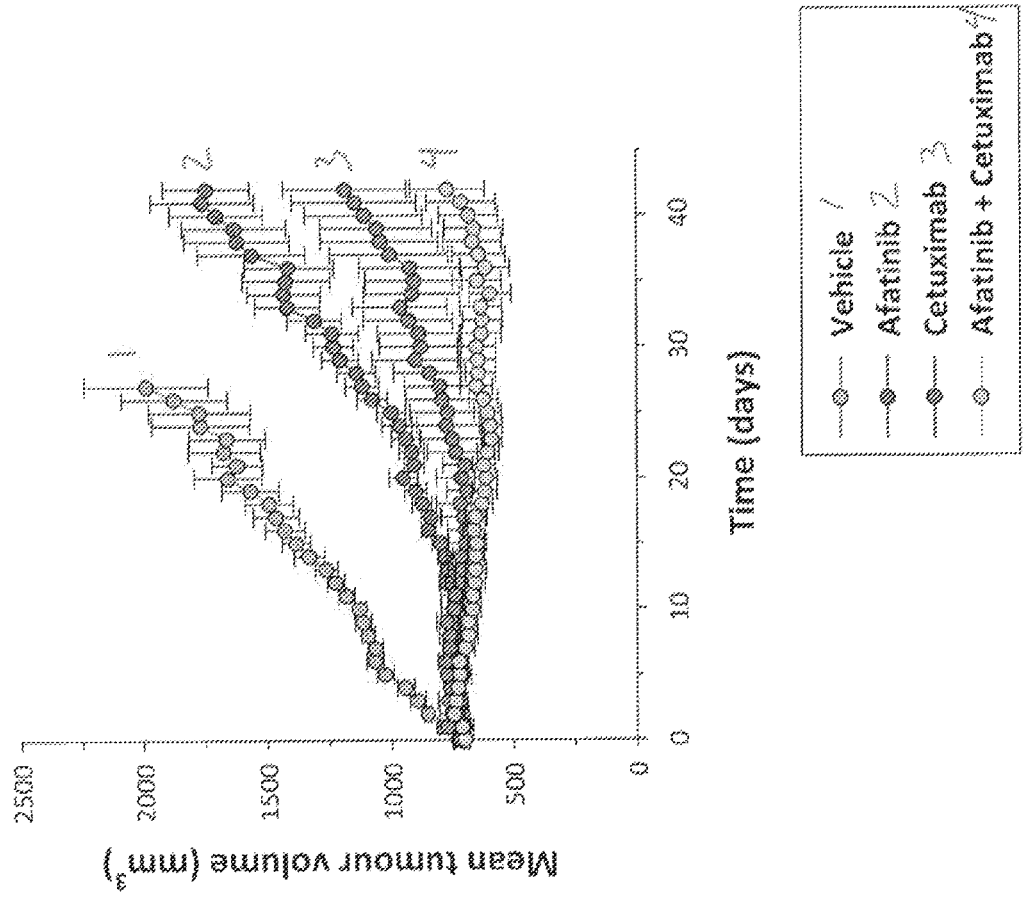
FIG. 25: Average tumor volume (±S.E.M.) of H125 tumors treated with vehicle control (qw×6), 6 mg/kg afatinib (qd×42), 0.25 mg/mouse cetuximab (q3d×14) and the combination of afatinib & cetuximab.
Figure 26:
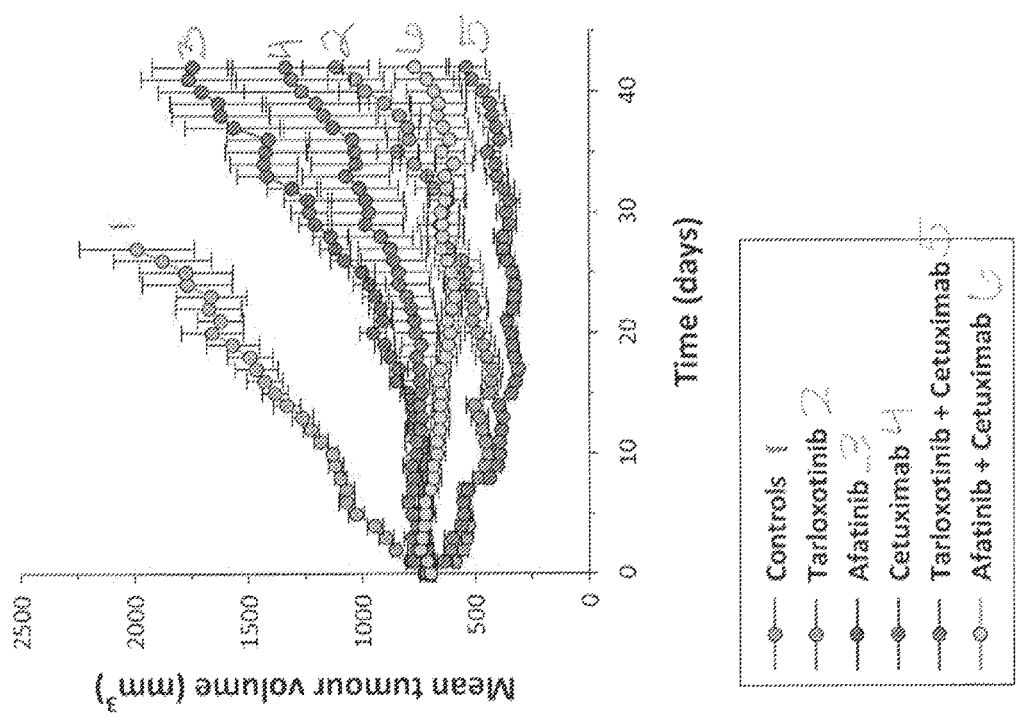
FIG. 26: Average tumor volume (±S.E.M.) of H125 tumors treated with vehicle control (qw×6), 48 mg/kg tarloxotinib (qw×6), 0.25 mg/mouse cetuximab (q3d×14), the combination of tarloxotinib & cetuximab, 6 mg/kg afatinib (qd×42) and the combination of afatinib & cetuximab.
Figure 27:
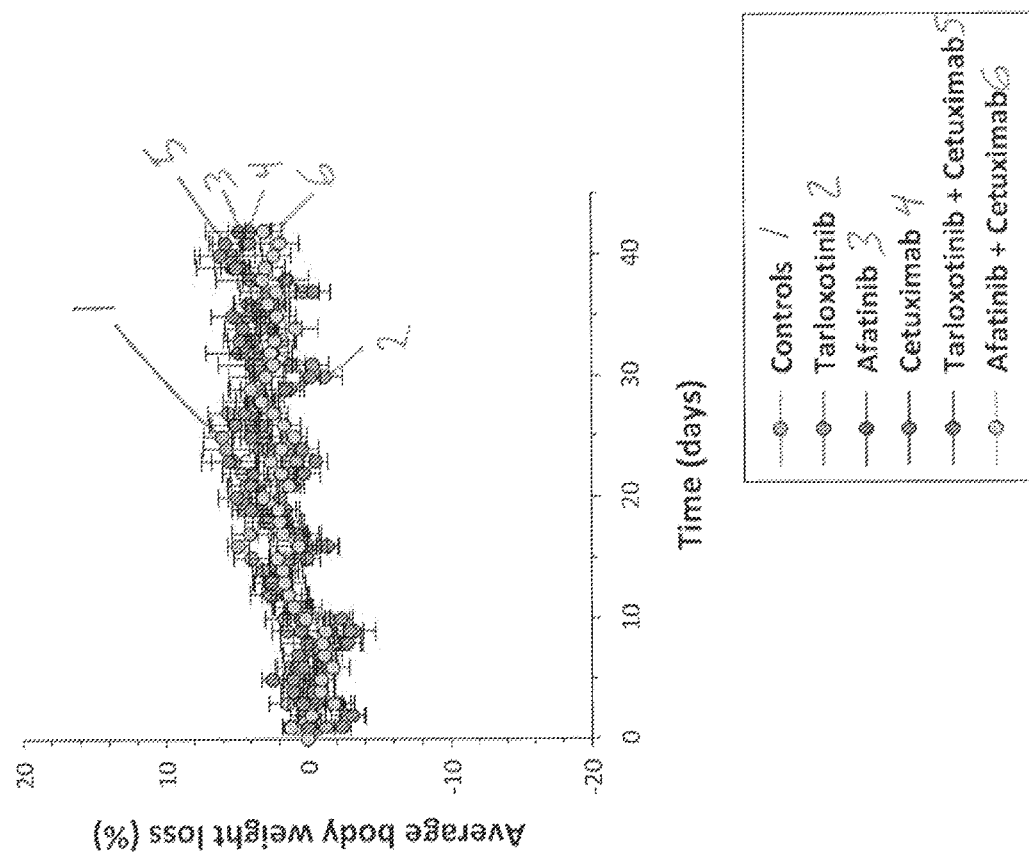
FIG. 27: Average body weight loss (±S.E.M.) in NIH-III mice bearing H125 tumors treated with vehicle control (qw×6), 48 mg/kg tarloxotinib (qw×6), 0.25 mg/mouse cetuximab (q3d×14), the combination of tarloxotinib & cetuximab, 6 mg/kg afatinib (qd×42) and the combination of afatinib & cetuximab.
Figure 28:
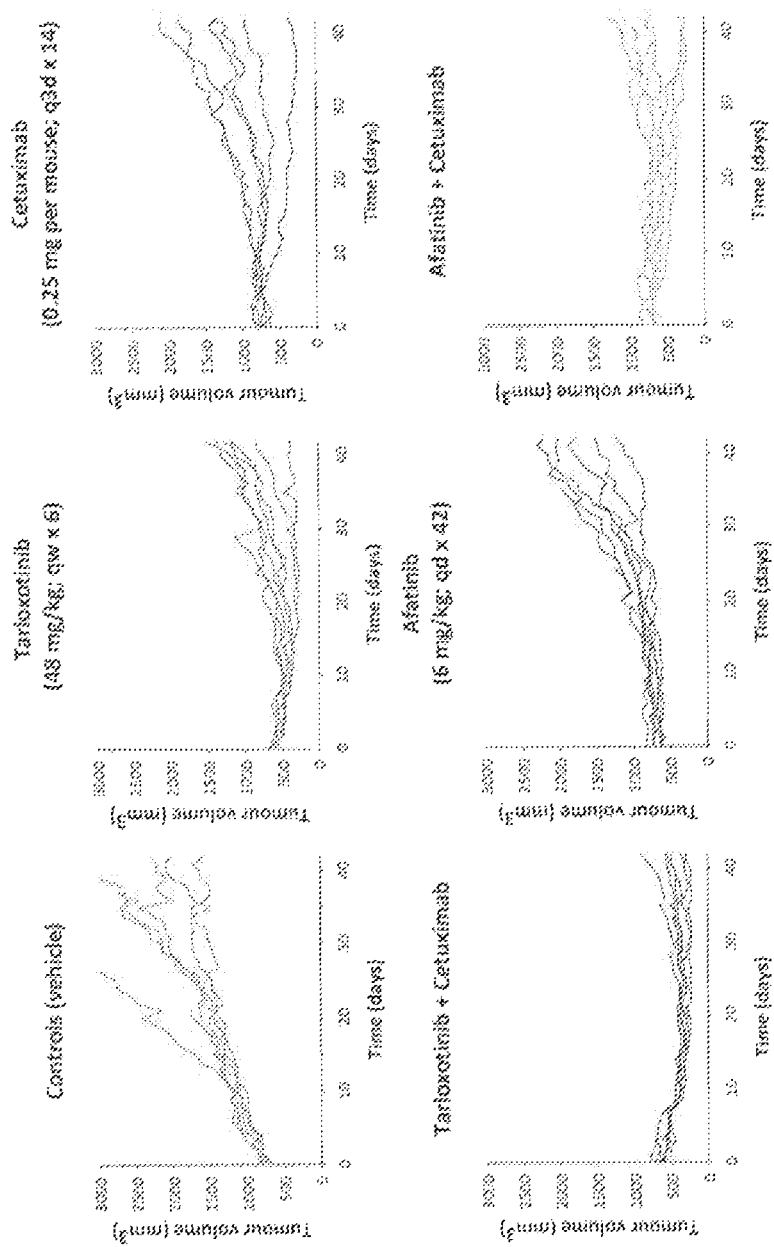
FIG. 28: Individual tumor volume of H125 tumors treated with vehicle control (qw×6), 48 mg/kg tarloxotinib (qw×6), 0.25 mg/mouse cetuximab (q3d×14), the combination of tarloxotinib & cetuximab, 6 mg/kg afatinib (qd×42) and the combination of afatinib & cetuximab.

For FIG. 18, anoxic experiments FaDu cells were seeded under anaerobic conditions. Four hours after drug addition, anoxic plates were removed from the anaerobic chamber and placed into a humidified incubator (37° C./5% CO2) for a further 20 hours. For oxic experiments FaDu cells were seeded and drug treated for 24 h in a humidified incubator (37° C./5% $CO_2$). IC50 values represent concentration of agent required to reduce proliferation by 50% relative to untreated controls. IC50 values are mean±standard error of >3 independent experiments.

Anoxic conditions significantly reduced the cetuximab sensitivity of FaDu cells. Anoxic conditions did not modify the sensitivity of FaDu cells to erlotinib exposure. Anoxic conditions significantly enhanced the TH-4000 sensitivity in FaDu cells. TH-4000E was substantially more dose potent than either cetuximab or erlotinib in FaDu cells. TH-4000 displayed a deactivation ratio of 62-fold relative to TH-4000E. TH-4000 was 15-fold more dose-potent against FaDu cells following 4 hours anoxia versus oxia.

Example 8. Target Modulation by Various EGFR-Targeted Agents in FaDu Cells

The objective of this study was to determine the concentration dependent relationship of various EGFR-targeted agents on the expression of EGFR and its downstream signal transducers, pAkt and pERK.

Cell Line

This study utilized the human hypopharnygeal cell line. FaDu (ATCC #HTB-43). FaDu cells were grown in αMEM culture medium supplemented with 5% FBS, without routine use of antibiotics (P/S). Cultures were re-established from authenticated frozen stocks in liquid nitrogen at either >24 passages or >90 days in culture (whichever came first). The frozen cell stocks were confirmed to be free of *mycoplasma* using a PCR-ELIZA kit (Roche Diagnostics GmbH, Mannheim, Germany).

Culture Conditions and Lysate Preparation

FaDu cells were seeded (700 k per well) in 6 well plates and left to settle overnight. Cells were then incubated with gradient concentrations of TH-4000, TH-4000E or cetuximab (3-fold dilutions) for 1 h. Cells were then stimulated with 50 ng/mL EGF (Sigma #E9644) for 15 mins.

Lysate Preparation for Western Blotting

Cells were washed once in ice-cold PBS. Lysates were prepared by incubating the cells with modified RIPA buffer (RIPA [50 mmol/L Tris-HCl, 1% NP-40, 0.25% Na-deoxycholate, 150 mmol/L NaCl, 1.0 mmol/L EDTA]+1.0 mmol/L $Na_3VO_4$+1.0 mmol/L NaF+1× protease inhibitor cocktail (Sigma #P8340)) on ice for 30 mins. After clarification, a BCA assay was performed to determine the protein concentration of the samples. Absorbance readings were performed at 550 nm.

Western Blotting

Cellular lysates were resolved by gel electrophoresis and immunoblotted for various members of the EGFR signaling axis. Each loading volume included 10 μg of protein and 25% SDS sample buffer (Life Technologies #NP0007). Samples were loaded onto NuPAGE 4-12% Bis-Tris 15 well gels (Life Technologies #NP0336) and run in MES running buffer (Life Technologies #NP0002) for approximately 2 h's at 120V or until the samples had run off the gel (whichever came first). Samples were then transferred (Transfer buffer: 25 mM Tris, 192 mM glycine, 20% methanol) for 80 mins at 100V onto nitrocellulose membranes. Blots were blocked in 5% BSA or 5% phosphoblocker (CellBiolabs #AKR-104) in TBS-T for at least 1 h. The primary and secondary antibodies utilized have been summarized in Tables 6 & 7. Briefly, blots were incubated with primary antibodies overnight at 4° C. After three 5 min washes in TBS-T, blots were then incubated with the appropriate HRP-conjugated secondary antibody for at least 2 hours at room temperature. In all instances, blots were imaged on the Fijifilm LAS 4000 system using Supersignal West Pico Chemiluminescent substrate (Life Technologies, #34080). As the target proteins (e.g. pERK and pAkt) were of similar band size to β-actin (control), the bound antibody was removed by incubating the blot with Restore Western blot stripping buffer (Thermofisher Scientific #21059) for 15 mins. After a single wash in TBS-T, the blots were then probed for β-actin or α-tubulin.

TABLE 6

Blocking Conditions and Primary Antibodies

| Primary Antibody | Source (Catalog No.) | Blocking agent | Species | Dilution |
| --- | --- | --- | --- | --- |
| pEGFR (Y1068) | Cell signalling (Lot #13, Cat # 2234S) | 5% BSA in TBS-T | Rabbit | 1:1500 |
| pEGFR (Y1092) | Sapphire Biosciences (Lot # GR149343, Cat # 120-40815) | 5% phosphoblocker in TBS-T | Rabbit | 1:1500 |

TABLE 6-continued

Blocking Conditions and Primary Antibodies

| Primary Antibody | Source (Catalog No.) | Blocking agent | Species | Dilution |
|---|---|---|---|---|
| pEGFR (1173) | Cell Signalling (Lot #6, Cat # 4407L) | 5% phosphoblocker in TBS-T | Rabbit | 1:1500 |
| pERK | Cell signalling (Lot 26; #9101S) | 5% BSA in TBS-T | Rabbit | 1:1500 |
| pAkt | Cell signalling (Lot 16; #4060S) | 5% BSA in TBS-T | Rabbit | 1:1500 |
| α-tubulin | Sigma (023M4813, T6074) | 5% BSA in TBS-T | Mouse | 1:5000 |
| Actin | Millipore (clone C4, Lot #2279536) | 5% BSA in TBS-T | Mouse | 1:5000 |

TABLE 7

Secondary Antibodies

| Secondary Antibody | Source (Catalog No.) | Dilution |
|---|---|---|
| Goat anti-mouse IgG-HRP | Santa Cruz (#J2212) | 1:5000 |
| Goat anti-rabbit IgG-HRP | Santa Cruz (#H2112) | 1:5000 |

TH-4000E was superior to cetuximab at inhibiting EGFR signaling. TH-4000E completely silenced pEGFR (Y1068) and pERK expression at concentrations of 0.12 μM or greater. Similarly, pAkt expression was largely silenced at concentrations above 0.12 μM. Cetuximab partially silenced pEGFR expression at concentrations of 1.1 μM or greater, but this had minimal impact on downstream signaling via pAkt and pERK. Exposure up to 10 μM cetuximab failed to silence pAkt and pERK activity. TH-4000E was at least 250-fold more dose potent than cetuximab as judged by inhibition of EGFR pathway signal transduction. TH-4000E (effector of TH-4000) was superior to TH-4000 (prodrug) at inhibiting EGFR signaling. TH-4000 completely silenced pEGFR expression up to 1.1 μM (comp. 0.041 μM for TH-4000E)

pAkt expression was completely silenced to 0.371 μM. TH-4000E was approximately 28-fold more dose potent than TH-4000 as judged by inhibition of EGFR pathway signal transduction.

TH-4000E was at least 250-fold more dose potent than cetuximab. TH-4000 was less efficient at inhibiting EGFR signaling than TH-400E, consistent with its mechanism of action.

Example 9. Influence of Hypoxia on TH-4000E Sensitivity in FaDu Cells

The objective of this study was to determine how hypoxia preconditioning alters TH-4000E sensitivity in FaDu cells.
Cell Line
This study utilized the human hypopharnygeal cell line, FaDu (ATCC #HTB-43). FaDu cells were grown in αMEM culture medium supplemented with 5% FBS, without routine use of antibiotics (P/S). Cultures were re-established from authenticated frozen stocks in liquid nitrogen at either >24 passages or >90 days in culture (whichever comes first). The frozen cell stocks were confirmed to be free of *mycoplasma* using a PCR-ELIZA kit (Roche Diagnostics GmbH, Mannheim, Germany).

Culture Conditions and Lysate Preparation
FaDu cells were seeded (500 k per well) in 6 well plates under both 0.1% $O_2$ and 21% $O_2$ for 48 hours. After 48 h of hypoxia preconditioning, cells were incubated with various concentrations of TH-4000E for 1 h. Cells were then stimulated with 50 ng/mL EGF (Sigma #E9644) for 15 mins.
Lysate Preparation for Western Blotting
After the designated period of anoxic exposure, cells were washed once in ice-cold PBS. Lysates were prepared by incubating the cells with modified RIPA buffer (RIPA [50 mmol/L Tris-HCl, 1% NP-40, 0.25% Na-deoxycholate, 150 mmol/L NaCl, 1.0 mmol/L EDTA]+1.0 mmol/L $Na_3VO_4$+ 1.0 mmol/L NaF+1×protease inhibitor cocktail (Sigma #P8340)) on ice for 30 mins. After clarification, a BCA assay was performed to determine the protein concentration of the samples. Absorbance readings were performed at 550 nm.
Western Blotting
Cellular lysates were resolved by gel electrophoresis and immunoblotted for various members of the EGFR signaling axis. Each loading volume included 10 μg of protein and 25% LDS sample buffer (Life Technologies #NP0007). Samples were loaded onto NuPAGE 4-12% Bis-Tris 15 well gels (Life Technologies #NP0336) and run in MES running buffer (Life Technologies #NP0002) for approximately 2 h's at 120V or until the samples had run off the gel (whichever came first). Samples were then transferred (Transfer buffer: 25 mM Tris, 192 mM glycine, 20% methanol) for 80 mins at 100V onto nitrocellulose membranes. Blots were blocked in 5% BSA or 5% phosphoblocker (CellBiolabs #AKR-104) in TBS-T for at least 1 h. The primary and secondary antibodies utilized have been summarized in Tables 8 & 9. Briefly, blots were incubated with primary antibodies overnight at 4° C. After three 5 min washes in TBS-T, blots were then incubated with the appropriate HRP-conjugated secondary antibody for at least 2 hours at room temperature. In all instances, blots were imaged on the Fijifilm LAS 4000 system using Supersignal West Pico Chemiluminescent substrate (Life Technologies, #34080). As the target proteins (e.g. pERK and pAkt) were of similar band size to actin (control), the bound antibody was removed by incubating the blot with Restore Western blot stripping buffer (Thermofisher Scientific #21059) for 15 mins. After a single wash in TBS-T, the blots were then probed for β-actin or α-tubulin.

TABLE 8

Blocking Conditions and Primary

| Primary Antibody | Source (Catalog No.) | Blocking agent | Species | Dilution |
|---|---|---|---|---|
| pEGFR (Y1068) | Cell signalling (Lot #13, Cat # 2234S) | 5% BSA in TBS-T | Rabbit | 1:1500 |
| pEGFR (Y1092) | Sapphire Biosciences (Lot #GR149343, Cat # 120-40815) | 5% phosphoblocker in TBS-T | Rabbit | 1:1500 |
| pEGFR (1173) | Cell Signalling (Lot #6, Cat # 4407L) | 5% phosphoblocker in TBS-T | Rabbit | 1:1500 |
| pERK | Cell signalling (Lot 26; #9101S) | 5% BSA in TBS-T | Rabbit | 1:1500 |
| pAkt | Cell signalling (Lot 16; #4060S) | 5% BSA in TBS-T | Rabbit | 1:1500 |
| α-tubulin | Sigma (023M4813, T6074) | 5% BSA in TBS-T | Mouse | 1:7000 |
| Actin | Millipore (clone C4, Lot #2279536) | 5% BSA in TBS-T | Mouse | 1:7000 |

TABLE 9

| Secondary Antibodies | | |
| --- | --- | --- |
| Secondary Antibody | Source (Catalog No.) | Dilution |
| Goat anti-mouse IgG-HRP | Santa Cruz (#J2212) | 1:5000 |
| Goat anti-rabbit IgG-HRP | Santa Cruz (#H2112) | 1:5000 |

TH-4000E sensitivity was comparable between the oxia- and hypoxia-preconditioned cells. Near complete silencing of EGFR signalling was observed across the concentration range of TH-4000E utilized (10.0-0.37 umol/L).

Hypoxia preconditioning does not alter TH-4000E sensitivity at the dilutions of TH-4000E utilized.

Example 10. Kinetics of EGFR Induction

The objective of this study was to determine how EGFR expression is altered by hypoxia in the hypopharyngeal cell line FaDu.

Cell Line

This study utilized the human hypopharnygeal cell line, FaDu (ATCC #HTB-43). FaDu cells were grown in αMEM culture medium supplemented with 5% FBS, without routine use of antibiotics (P/S). Cultures were re-established from authenticated frozen stocks in liquid nitrogen at either >24 passages or >90 days in culture (whichever comes first). The frozen cell stocks were confirmed to be free of *mycoplasma* using a PCR-ELIZA kit (Roche Diagnostics GmbH, Mannheim, Germany).

Culture Conditions

FaDu cells were seeded (700 k per) in T25 flasks and allowed to settle overnight at 21% $O_2$. The culture media (αMEM+5% FCS) was aspirated and flasks were taken into the $H_2$/palladium-catalyst anaerobic chamber (Bactron, Shellab). Fresh anoxia-equilibrated media (αMEM+5% FCS+P/S+1% additives) was added to each flask. Cells were exposed to anoxia for variable periods with and without oxic recovery (Table 10).

TABLE 10

| FaDu culture conditions | |
| --- | --- |
| Flask No. | Culture Conditions |
| 1 | Oxic control (Anoxia 0 h) |
| 2 | Anoxia for 1 h |
| 3 | Anoxia for 3 h |
| 4 | Anoxia for 5 h |
| 5 | Anoxia for 7 h |
| 6 | Anoxia for 9 h |
| 7 | Anoxia for 14 h with no (0 h) oxic recovery |
| 8 | Anoxia for 14 h with a 1 h oxic recovery |
| 9 | Anoxia for 14 h with a 5 h oxic recovery |

Lysate Preparation for Western Blotting

After the designated period of anoxic exposure, cells were washed once in ice-cold PBS. Lysates were prepared by incubating the cells with modified RIPA buffer (RIPA [50 mmol/L Tris-HCl, 1% NP-40, 0.25% Na-deoxycholate, 150 mmol/L NaCl. 1.0 mmol/L EDTA]+1.0 mmol/L $Na_3VO_4$+1.0 mmol/L NaF+1× protease inhibitor cocktail (Sigma #P8340)) on ice for 30 mins. After clarification, a BCA assay was performed to determine the protein concentration of the samples. Absorbance readings were performed at 550 nM.

Western Blotting

1 Cellular lysates were resolved by gel electrophoresis and immunoblotted for various members of the EGFR signaling axis. Each loading volume included 10 μg of protein and 25% LDS sample buffer (Life Technologies #NP0007). Samples were loaded onto NuPAGE 4-12% Bis-Tris 15 well gels (Life Technologies #NP0336) and run in MES running buffer (Life Technologies #NP0002) for approximately 2 h's at 120V or until the samples had run off the gel (whichever came first). Samples were then transferred (Transfer buffer: 25 mM Tris, 192 mM glycine, 20% methanol) for 80 mins at 100V onto nitrocellulose membranes. Blots were blocked in either 5% phosphoblocker (Cell Biolabs #AKR-104) or 5% BSA in TBS-T for at least 1 h. The primary and secondary antibodies utilized have been summarized in Tables 1 & 12. Briefly, blots were incubated with primary antibodies overnight at 4° C. After three 5 min washes in TBS-T, blots were then incubated with the appropriate HRP-conjugated secondary antibody for at least 2 hours at room temperature. In all instances, blots were imaged on the Fijifilm LAS 4000 system using Supersignal West Pico Chemiluminescent substrate (Life Technologies, #34080). As the target proteins (e.g. pERK and pAkt) were of similar band size to actin (control), the bound antibody was removed by incubating the blot with 0.2M NaOH for 5 mins. After reblocking for at least 1 h in 5% BSA in TBS-T, the blots were then probed for actin.

TABLE 11

| Blocking Conditions and Primary Antibodies | | | | |
| --- | --- | --- | --- | --- |
| Primary Antibody | Source (Catalog No.) | Blocking agent | Species | Dilution |
| tEGFR | Cell signalling (09/2013) Lot # 15 Product No. 2232L | 5% BSA in TBS-T | Rabbit | 1:500 |
| pEGFR (Y1092) | Sapphire Biosciences (Lot # GR149343, Cat # 120-40815) | 5% phosphoblocker in TBS-T | Rabbit | 1:500 |
| Actin | Millipore (clone C4, Lot #2279536) | 5% BSA in TBS-T | Mouse | 1:5000 |

TABLE 12

| Secondary Antibodies | | |
| --- | --- | --- |
| Secondary Antibody | Source (Catalog No.) | Dilution |
| Goat anti-mouse IgG-HRP | Santa Cruz (#J2212) | 1:5000 |
| Goat anti-rabbit IgG-HRP | Santa Cruz (#H2112) | 1:5000 |

TABLE 13

| Gel running order: | | |
| --- | --- | --- |
| Well | Sample | Loading vol |
| 1 | Ladder | |
| 2 | Oxic control | 20 |
| 3 | Anoxic 1 h | 20 |
| 4 | Anoxic 3 h | 20 |
| 5 | Anoxic 5 h | 20 |
| 6 | Anoxic 7 h | 20 |
| 7 | Anoxic 9 h | 20 |

TABLE 13-continued

Gel running order:

| Well | Sample | Loading vol |
|---|---|---|
| 8 | Anoxic 14 h | 20 |
| 9 | Anoxic 14 h + 1 h recovery | 20 |
| 10 | Anoxic 14 h + 5 h recovery | 20 |

Total EGFR (tEGFR) expression was unaltered by 14 hours of anoxia. Phospho-EGFR (Y1092) levels increased in FaDu cells with duration of anoxia. Phospho-EGFR (Y1092) levels remained elevated in FaDu cells five hours after re-exposure to normoxia.

Temporal induction of pEGFR (Y1092) in FaDu cells were observed under anoxic culture conditions, pEGFR (Y1092) levels were sustainable for at least 5 hours following re-exposure to normoxia.

Example 11: TH-4000 in Combination with Cetuximab Vs Afatinib in Combination with Cetuximab in the Wild Type EGFR Driven H125 Non-Small Cell Lung Cancer Xenograft The primary objectives of this example was to compare the efficacy of weekly single agent tarloxotinib to the tarloxotinib/cetuximab combination in H125 xenografts and to compare the efficacy of tarloxotinib/cetuximab to afatinib/cetuximab in H125 xenografts as well as assess the toxicity of the tarloxotinib/cetuximab combination in comparison to afatinib/cetuximab.

All agents were dosed at human PK equivalence. The combination of tarloxotinib plus cetuximab was significantly more efficacious than afatinib plus cetuximab in WT EGFR driven H125 xenografts (ORR of 67% and 37%, respectively). Single agent ORR were 29%, 17% and 0% for tarloxotinib, cetuximab and afatinib, respectively (Table 3). Analysis of tumour growth inhibition (TGI %; day 27) demonstrated that the combination of tarloxotinib/cetuximab was the most active (TGI=81%) followed by tarloxotinib alone (TGI=69%). The combination of afatinib/cetuximab displayed intermediate activity (TGI=67%). Afatinib and cetuximab single agent treatment groups had inferior outcomes (Table 1). Non-significant body weight loss was recorded in all treatment groups.

| | Experimental parameters |
|---|---|
| Gender | Female |
| Mouse strain | NIH-III; Crl:NIH Lyst$^{bg}$ Foxn1$^{nu}$ Btk$^{xid}$ |
| Tumour injection site | Subcutaneous |
| Cell line | H125 |
| Cells per inoculation | 1.0 × 10$^7$ cells |
| Drug solutions | Tarloxotinib and afatinib in WFI containing 20% 2-hydroxylpropyl-β-cyclodextrin<br>Cetuximab 5 mg/mL infusion vials diluted in saline immediately prior to administration |
| Injection volume | 10 ml/kg (0.01 ml/g) for tarloxotinib & afatinib; 0.25 mL/injection for cetuximab |
| Drug administration route | Tarloxotimb - intraperitoneal (i.p.)<br>Cetuximab - intraperitoneal (i.p.)<br>Afatinib - oral gavage (p.o.) |
| Tumour volume at start | Range: 621-845 mm$^3$, Mean ± S.D: 707 mm$^3$ ± 57 mm$^3$ |
| Treatment dates | Mice were randomly assigned into treatment groups on days between 7$^{th}$ Oct. 2015 and 17$^{th}$ Oct. 2015 and drug administration for each animal began on day of assignment. |
| Evaluations | Tumour size and bodyweight were measured every day. |
| Criteria for culling mice | Volume of the tumour exceeded four-times the initial (day 0) volume (RTV4) (endpoint)<br>Mean tumour diameter exceeds 20 mm (ethical criteria)<br>Body weight change reached 20% below the day 0 measurement (ethical criteria)<br>Evidence of metastasis or extensive tumor ulceration (ethical criteria) |
| Endpoints | Tumour diameter exceeds 20 mm<br>Median RTV$^4$ (defined as time to reach tumour volume 4X larger than day 0)<br>Weight loss nadir |

Methods

H125 tumour bearing NIH-III mice were randomized to one of the following treatment groups:

Group A: Vehicle (WFI containing 20% 2-hydroxylpropyl-β-cyclodextrin), i.p, qw×6

Group B: Tarloxotinib, 48 mg/kg, qw×6

Group C: Cetuximab, 0.25 mg/mouse, q3d×14

Group D: Tarloxotinib, 48 mg/kg, qw×6 in combination with cetuximab, 0.25 mg/mouse, q3d×14

Group E: Afatinib, 6 mg/kg, qd×42

Group F: Afatinib, 6 mg/kg, qd×42 in combination with cetuximab, 0.25 mg/mouse, q3d×14

All doses and treatment schedules were based on best available information with regards to clinically relevant doses and schedules for each agent. The human equivalent doses of tarloxotinib and afatinib in NIH-III nude mice were determined in-house after adjusting for plasma protein binding in both species. The murine (NIH-III) tarloxotinib dose of 48 mg/kg is generates plasma exposures of free drug equivalent to 150 mg/m$^2$ in humans (Investigator's Brochure TH-CR-601, Threshold Pharmaceuticals, INC) and was administered once weekly. The murine dose of 6 mg/kg for afatinib was found to be equivalent to 40 mg/kg in humans (Wind et al, 2013, Clin Pharmacokinet; 52:1101-1109) and was dosed daily oral. The dose of cetuximab used was based on the findings by Luo et al (2005, Cancer Chemother Pharmacol; 56[5]:455) where a dose of 0.25 mg per mouse was equivalent to a clinically achievable dose of cetuximab (with target saturation observed). Administration in mice was q3d to correct for shorter elimination half-life in murine versus human subjects (40-42 vs 114 hr, respectively).

The combination of tarloxotinib and cetuximab was more efficacious than either treatment as single agents. This combination led to the most robust antitumor activity in comparison to all other treatment groups with 4/6 (67%) evaluable tumours achieving PR and 2/6 SD.

The afatinib/cetuximab combination was more active than either afatinib or cetuximab alone. 3/8 tumours (38%) treated with the afatinib/cetuximab combination achieved PR while none achieved SD or PR with single agent afatinib.

The tarloxotinib/cetuximab combination led to a tumour growth inhibition (TGI %, day 27) of 81% relative to vehicle treated controls, whereas the afatinib/cetuximab combination led to a TGI of 67%.

Body weight loss in all treatment groups was <5%. No other signs of toxicity were observed except for a single case of diarrhoea in one mouse (day 13) treated with the combination of afatinib/cetuximab which resolved within 48 hours.

The phase 1b evaluation of afatinib and cetuximab in EGFR-mutation positive NSCLC patients with acquired resistance to first line TKIs demonstrated that the dose intensity achieved with the dual inhibition of EGFR by afatinib/cetuximab was associated with on-mechanism grade ¾ toxicities such as diarrhea and skin rash (Janjigian et al, 2014, *Can Discov*, 4:10). It is hypothesized that in this setting, the combination of tarloxotinib and cetuximab is likely to provide the dose intensity required for sufficient inhibition of ErbB signaling while maintaining a therapeutic window. This study was undertaken to evaluate the therapeutic potential of tarloxotinib plus cetuximab relative to the combination of afatinib and cetuximab in a model of wild-type (WT) EGFR driven NSCLC.

The combination of tarloxotinib/cetuximab was significantly more efficacious than the afatinib/cetuximab combination in WT EGFR driven H125 xenografts. The combination of tarloxotinib and cetuximab was well tolerated and were not associated with any significant toxicities.

TABLE 14

Tumor groth inhibition (compared to controls of H125 tumors on day 27 following treatment with 48 mg/kg tarloxotinib (qw), 0.25 mg/mouse cetuximab (q3d), the combination of tarloxotinib & cetuximab, 6 mg/kg afatinib (qd) and the combination of afatinib & cetuximab

| Group | Mean tumor volume on day 27* ($mm^3$) ± SEM | TGI (%) relative to controls on day 27 | One-way ANOVA with Dunnett's post test |
|---|---|---|---|
| Control | 1989 ± 253 | — | — |
| Tarloxotinib | 615 ± 89 | 69 | $P < 0.05$ |
| Cetuximab | 874 ± 140 | 56 | $P < 0.05$ |
| Tarloxotinib + Cetuximab | 372 ± 31 | 81 | $P < 0.05$ |
| Afatinib | 1117 ± 67 | 44 | $P < 0.05$ |
| Afatinib + Cetuximab | 647 ± 65 | 67 | $P < 0.05$ |

TABLE 15

Study outcomes

| Group | Drug | Dose (mg/kg/dose) | Schedule | Animal number | Deaths due to drug toxicity | Deaths independent of drug toxicity | Day of Death (includes all deaths) | Reason for Death | Average Weight Loss Nadir (+/−SEM) [Day] |
|---|---|---|---|---|---|---|---|---|---|
| A | Vehicle (20% CDW) | — | qw x 6 | 7 | — | — | — | — | −0.8 ± 1.1 [day 5] |
| B | Tarloxotinib | 48 | qw x 6 | 7 | — | — | — | — | −3.3 ± 1.5 [day 9] |
| C | Cetuximab | 0.25 mg/mouse | q3d x 14 | 6 | — | — | — | — | −0.1 ± 0.6 [day 2] |
| D | Tarloxotinib + Cetuximab | 48 / 0.25 mg/mouse | qw x 6 / q3d x 14 | 7 | — | 1 | 24 | h | −3.1 ± 0.9 [day 9] |
| E | Afatinib | 6 | qd x 42 | 7 | — | 2 | 33, 35 | f | −1.6 ± 0.9 [day 9] |
| F | Afatinib + Cetuximab | 6 / 0.25 mg/mouse | qd x 42 / q3d x 14 | 8 | — | — | — | — | −1.8 ± 1.2 [day 6] |

Notes/abbreviations:

Vehicle 20% 2-hydroxylpropyl-β-cyclodextrin (Sigma Aldricli, lot MKBG9088V), dissolved in water for injection (DEMO S.A. Pharmaceutical Industry, lot 105467)

Deaths independent Excludes mice culled prior to endpoint that had already reached $RTV^4$ (e.g. mice culled early due to grade II ulceration) of drug toxicity Reasons for Death: Drug toxicity related: a—Found dead, b—Evidence of morbidity, c—Evidence of treatment-related adverse effect, d—Excessive weight loss (>20% from starting size)

Independent of drug toxicity: e—Irregular tumor growth, f—Tumor ulceration grade III, g—Tumor metastasis, h—Dosing aberration, i—Treatment-independent sickness, j—Animal husbandry concern

TABLE 16

Tumor growth response measured by RECIST criteria

| Group | Drug | Dose | Schedule | n* | PD | SD | PR | CR | R % |
|---|---|---|---|---|---|---|---|---|---|
| A | Vehicle (20% CDW) | — | qw x 6 | 7 | 7 | | | | 0% |
| B | Tarloxotinib | 48 | qw x 6 | 7 | | 5 | 2 | z | 29% |
| C | Cetuximab | 0.25 mg/mouse | q3d x 14 | 6 | 4 | 1 | 1 | | 17% |
| D | Tarloxotinib + Cetuximab | 48 / 0.25 mg/mouse | qw x 6 / q3d x 14 | 6 | | 2 | 4 | | 67% |

TABLE 16-continued

Tumor growth response measured by RECIST criteria

| Group | Drug | Dose | Schedule | n* | PD | SD | PR | CR | R % |
|---|---|---|---|---|---|---|---|---|---|
| E | Afatinib | 6 | qd x 42 | 5 | 5 | | | | 0% |
| F | Afatinib + Cetuximab | 6 0.25 mg/mouse | qd x 42 q3d x 14 | 8 | 3 | 2 | 3 | | 38% |

Notes/abbreviations:
PD—Progressive Disease: <50% regression from initial volume during entire study and >25% increase in initial volume at the conclusion of dosing
SD—Stable Disease: <50% regression from initial volume during entire study and ≤25% increase in initial volume at the conclusion of dosing
PR—Partial Response: ≥50% regression from initial volume for any one time point during entire study, but with measurable tumor (≥25 mm$^3$)
CR—Complete Response: Disappearance of measurable tumor volume (<25 mm$^3$) for any one time point during entire study.
R %—Response Rate: Percentage of evaluable tumors that have partial (PR) or complete (CR) responses.
*The sample size evaluable for tumor response includes all mice that completed the dosing schedule or reached tumor endpoint prior to the completion of dosing. All mice that were culled due to drug toxicity, tumor ulceration or dosing aberrations prior to the completion of dosing were excluded from tumor response analysis.

Example 12. Phase I Clinical Trial of TH-4000 in Human Patients

This Example describes an open-label and multi-center Phase I trial administering TH-4000 to cancer patients.
Formulation and Administration of TH-4000

TH-4000 for infusion was prepared in glass vials and administered intravenously over 1 hour via an infusion pump. The starting (Level 1) dose was 10 mg/m$^2$ weekly×8. A modified accelerated titration design was used (Simon et al., JNCI, 89:1138-47, incorporated herein by reference). 27 patients were enrolled at the initial dose levels. Until the first dose limiting toxicity (DLT) or Grade 2 toxicity that is clearly not related to disease progression, intercurrent illness, concomitant medications or other non-drug intervention occur during Cycle 1, the dose is increased 100% through successive levels. A DLT was defined as:
Grade 4 QTc interval prolongation in patient at 200 mg/m2 (DLT)
Grade 3 facial pain in patient at 200 mg/m2 (DLT)
Grade 3 Vestibular disturbance in patient at 200 mg/m2

Before proceeding to the next dose level, the medical monitor and the principal investigators reviewed and discussed the available relevant safety and PK data.
Study Population 27 patients with advanced solid tumors were (all comers) were enrolled in this study. The primary objective of the study was to determine MTD and DLTs. The secondary objectives include PK, safety and efficacy studies. The MTD was established as 150 mg/m$^2$/w.
Treatment Period:

For the treatment, patients were injected with a starting dose of 10 mg/m$^2$ through IV over 1 hour, once every week. The assessment of disease was done at week 6 and then every 8 weeks. The PK analysis of TH-4000 and TH-4000E was assessed in cycles 1 and 2.
Dose Escalation A traditional 3+3 dose escalation design (<100%) was implemented. Successive cohorts of participants (4-6 participants/cohort) were each started on a fixed dose. Real time PK was studied for the first 2 cohorts.
Results TH-4000 administration of 80 mg/m$^2$ (1 h infusion) in 15 patients resulted in no dermatitis acneiform or pruritus (0/15); and a low incidence of grade ½ maculo-papular rash (4/15 patients) and diarrhea (1/15 patients). Plasma exposure at a 80 mg/m$^2$ dose gave a AUC0-inf≈5 weeks continuous daily compared with afatinib which is dosed at 40 mg/d. Systemic TH-4000-E exposure was <1% of TH-4000 (median 0.88%; range 0.29%-2.4%). This toxicokinetic relationship is consistent with the systemic deactivation of TH-4000 in humans.

TH-4000 exhibited a tumor-selective dose intensification of TH-4000E (e.g. an >8-fold increase in AUC) with a tumor half-life of z 2.5 days and a p-EGFR shutdown for greater than 4 days, which is better than afatinib, which has a p-EGFR shutdown of less than 6 h. Thus, TH-4000 was shown to have the advantage of irreversibly inhibiting both HIF2α-driven wild type EGFR and wild type EGFR sequestered in endocytic vesicles in a hypoxic environment over other therapies.

Example 13: TH-4000 in Patients with EGFR-Mutant, T790M-Negative. Advanced Non-Small Cell Lung Cancer Progressing on an EGFR Tyrosine Kinase Inhibitor This Example describes a single-arm, open-label, multi-center, two-stage, Phase 11 trial administering TH-4000 to in patients with EGFR-Mutant, T790M-Negative, Advanced Non-Small Cell Lung Cancer.
Formulation and Administration of TH-4000

TH-4000 was supplied frozen (−20±5° C.) in 20 mL vials containing a minimum of 120 mg TH-4000 in at least 10 mL of a sterile, preservative-free solution containing 40% 2-hydroxypropyl-beta-cyclodextrin, 20 mM citrate, at a pH of 3-4. The concentration of TH-4000 was 12 mg/mL. TH-4000 vials were thawed on a shelf at room temperature prior to use. Once thawed, TH-4000 vials were diluted into 5% Dextrose in Water (D5W) within 12 hours. D5W for dilution of TH-4000 was obtained from a commercial source and was stored at room temperature. The final TH-4000 concentration of the prepared TH-4000/DSW solution was about 1 mg/mL.

TH-4000 for infusion was prepared in glass vials and administered intravenously over 1 hour via an infusion pump. The starting dose was 150 mg/m2 administered on Days 1, 8, 15, and 22 of each 28-day cycle until progressive disease (PD) or unacceptable toxicity. The study utilized an optimal Simon two-stage design (Simon et al., JNCI, 89:1138-47, incorporated herein by reference). Dose modification rules were followed for toxicities that were considered possibly related to TH-4000. Prior to administration of a subsequent dose of TH-4000, a patient who had experienced one of the following treatment-related toxicities with the previous dose must meet the following criteria:
QTcF interval prolongation of Grade 1 or less;
Skin rash of Grade 2 or less; and
Gastrointestinal (GI) toxicity of Grade 2 or less.
Any other clinically significant TH-4000-related toxicity must return to at least Grade 1.

In the event that the administration of TH-4000 was delayed for TH-4000-related toxicity, the patient may have received subsequent administrations of TH-4000 at a 25% to 50% dose reduction from the prior dose.

Study Population

Up to 37 patients with epidermal growth factor (EGFR)-mutant, T790M-negative, advanced non-small cell lung cancer (NSCLC) (all comers) were enrolled in this study. The primary objective of the study was to evaluate the antitumor activity of TH-4000 as determined by response rate in patients with EGFR-mutant, T790M-negative, advanced NSCLC progressing on an EGFR TKI. The secondary objectives included assessing the safety and tolerability of TH-4000 in this study population; evaluating further measures of antitumor activity of TH-4000 including duration of response (DOR), progression-free survival (PFS), and overall survival (OS); investigating the pharmacokinetics (PK) of TH-4000 (prodrug) and TH-4000E (TKI effector) in this study population and to explore potential PK/pharmacodynamic relationships; and evaluate whether there is an association between plasma exposure to TH-4000 and its active metabolite. TH-4000E, and effects on cardiac repolarization.

Duration of Study:

This trial entailed the following three phases: Screening, treatment, and follow-up. The estimated total duration of the active part of the study for each patient was approximately 30 weeks, as follows:

Screening Phase: −28 Days

Screening and baseline procedures may be up to 28 days prior to first planned dose.

Treatment Phase: Weeks 1-26 (26 Weeks)

An average of six 28-day treatment periods (24 weeks) was followed by study treatment termination visit 2 weeks after last dose of study medication. Patients were allowed to continue treatment on study until they have evidence of significant treatment-related toxicity or progressive disease. The accrual period was about 12 months.

Treatment Period:

For the treatment, patients were injected with a starting dose of 150 mg/m$^2$ through IV over 1 hour, administered on Days 1, 8, 15, and 22 of each 28-day cycle until progressive disease (PD) or unacceptable toxicity. Potential predictors of clinical activity of TH-4000 was evaluated based on hypoxia PET imaging (e.g., hypoxic tumor volume and hypoxic fraction at sites where available only) and analyses from tumor tissue, circulating tumor cells or plasma (e.g., WT:Mutant EGFR allele ratios; EGFR/pEGFR and HER2/pHER2 protein expression; EGFR and HER2 copy number gains; Veristrat plasma assay for likelihood of response to EGFR TKI; and/or identification of other known molecular abnormalities associated with TKI resistance (such as MET amplification or KRAS mutation).

Pharmacokinetic sampling for plasma TH-4000 and TH-4000E was collected for patients on Cycle 1 Day 1 predose, 30 minutes after start of infusion, end of infusion, 30 minutes after end of infusion, and 1 hour (h), 2 h, 3 h, 5 h and 24 h after the end of infusion. Concentrations of TH-4000 and TH-4000E was reported along with the following parameters: maximum observed time to peak plasma concentration (Tmax); plasma concentrations (Cmax), time to maximum); the magnitude of slope of linear regression of log concentration (Tmax), elimination constant vs time profile during terminal phase (Kel); terminal half-life (T½); area under the concentration-time curve (AUC), area under the curve from HrO through last quantifiable concentration time (AUClast); area under the curve (AUC); clearance (CL), volume of distribution of the post-distribution phase and (cl); volume of distribution at steady state (Vss); apparent volume of distribution in the post distributive phase (VB) exploratory.

Follow-Up: Up to 1 Year after First Dose

Patients will be contacted for survival and post-study treatment information approximately every 3 months for up to 12 months after their first dose until death, lost to follow-up, or study closure.

Example 14: TH-4000 in Patients with Recurrent or Metastatic Squamous Cell Carcinoma of the Head and Neck or Skin This Example describes an open-label, multi-center, two-stage, Phase II trial administering TH-4000 to in patients with recurrent or metastatic squamous cell carcinoma of the head and neck or skin.

Formulation and Administration of TH-4000

TH-4000 was supplied frozen (−20-5° C.) in 20 mL vials containing a minimum of 120 to 150 mg TH-4000 in at least 10 mL of a sterile, preservative-free solution containing 40% 2-hydroxypropyl-beta-cyclodextrin. 20 mM citrate, at a pH of 3-4. The concentration of TH-4000 was 12 mg/mL. TH-4000 vials were thawed on a shelf at room temperature prior to use. Once thawed, TH-4000 vials were diluted into 5% Dextrose in Water (D5W) within 12 hours. D5W for dilution of TH-4000 was obtained from a commercial source and was stored at room temperature. The final TH-4000 concentration of the prepared TH-4000/DSW solution was about 1 mg/mL.

TH-4000 for infusion was prepared in glass vials and administered intravenously over 1 hour via an infusion pump. The starting dose was 150 mg/m$^2$ administered on Days 1, 8, 15, and 22 of each 28-day cycle until progressive disease (PD) or unacceptable toxicity. The study utilized an optimal Simon two-stage design (Simon et al., JNCI, 89:1138-47, incorporated herein by reference). Dose modification rules were followed for toxicities that were considered possibly related to TH-4000. Prior to administration of a subsequent dose of TH-4000, a patient who had experienced one of the following treatment-related toxicities with the previous dose must have met the following criteria:
QTcF interval prolongation of Grade 1 or less
Skin rash of Grade 2 or less
Gastrointestinal (GI) toxicity of Grade 2 or less
Any other clinically significant TH-4000-related toxicity had to return to at least Grade 1.

In the event that the administration of TH-4000 was delayed for TH-4000-related toxicity, the patient may have received subsequent administrations of TH-4000 at a 25%-50% dose reduction from the prior dose.

Study Population 30 patients with recurrent or metastatic squamous cell carcinoma of the head and neck or skin were enrolled in this study. The primary objective of the study was to evaluate the antitumor activity of TH-4000 as determined by response rate in patients with recurrent and/or metastatic squamous cell carcinoma of the head and neck or skin. The secondary objectives include assessing the safety and tolerability of TH-4000 in this study population; evaluating further measures of antitumor activity of TH-4000 including duration of response (DOR), progression-free survival (PFS), and overall survival (OS); investigating the pharmacokinetics (PK) of TH-4000 (prodrug) and TH-4000E (TKI effector) in this study population and to explore potential PK/pharmacodynamic relationships; and evaluating whether there is an association between plasma exposure to TH-4000 and its active metabolite, TH-4000E, and effects on cardiac repolarization.

Duration of Study:

This trial entailed the following three phases: Screening, treatment, and follow-up. The estimated total duration of the active part of the study for each patient was approximately 30 weeks, as follows:

Screening Phase: −28 Days

Screening and baseline procedures were up to 28 days prior to first planned dose.

Treatment Phase: Weeks 1-26 (26 weeks)

An average of six 28-day treatment periods (24 weeks) followed by study treatment termination visit 2 weeks after last dose of study medication. Patients were allowed to continue treatment on study until they had evidence of significant treatment-related toxicity or progressive disease. The accrual period was about 12 months.

Treatment Period:

For the treatment, patients were injected with a starting dose of 150 mg/m$^2$ through IV over 1 hour, administered on Days 1, 8, 15, and 22 of each 28-day cycle until progressive disease (PD) or unacceptable toxicity. Potential predictors of clinical activity of TH-4000 were evaluated based on hypoxia PET imaging (e.g., hypoxic tumor volume and hypoxic fraction at sites where available only) and analyses from tumor tissue, circulating tumor cells or plasma (e.g., WT:Mutant EGFR allele ratios: EGFR/pEGFR and HER2/pHER2 protein expression; EGFR and HER2 copy number gains; Veristrat plasma assay for likelihood of response to EGFR TKI; and/or identification of other known molecular abnormalities associated with TKI resistance (such as MET amplification or KRAS mutation).

Pharmacokinetic sampling for plasma TH-4000 and TH-4000E was collected for patients on Cycle 1 Day 1 predose, 30 minutes after start of infusion, end of infusion. 30 minutes after end of infusion, and 1 hour (h), 2 h, 3 h, 5 h and 24 h after the end of infusion. Concentrations of TH-4000 and TH-4000E was reported along with the following parameters: maximum observed time to peak plasma concentration (Tmax); plasma concentrations (Cmax), time to maximum); the magnitude of slope of linear regression of log concentration (Tmax), elimination constant vs time profile during terminal phase (Kel); terminal half-life (T½); area under the concentration-time curve (AUC), area under the curve from HrO through last quantifiable concentration time (AUClast); area under the curve (AUC); clearance (CL), volume of distribution of the post-distribution phase and (cl); volume of distribution at steady state (Vss); apparent volume of distribution in the post distributive phase (VB) Exploratory.

Follow-Up: Up to 1 Year after First Dose

Patients were contacted for survival and post-study treatment information approximately every 3 months for up to 12 months after their first dose until death, lost to follow-up, or study closure.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

What is claimed is:

1. A method of treating cancer in a subject in need thereof, said method comprising administering to the subject a therapeutically effective amount of a compound, [(E)-4-[[4-(3-bromo-4-chloroanilino)pyrido[3,4-d]pyrimidin-6-yl]amino]-4-oxobut-2-enyl]-dimethyl-[(3-methyl-5-nitroimidazol-4-yl)methyl]azanium bromide,
wherein said cancer is characterized by wild-type activity of the EGFR protein.

2. The method of claim 1, wherein the amount of the compound administered is in the range of about 20 mg/m$^2$ to about 150 mg/m$^2$.

3. The method of claim 1, wherein the compound is administered intravenously.

4. The method of claim 1, wherein the compound is administered at a frequency in the range of at least once per day to once per month.

5. The method of claim 1, wherein the compound is administered at a frequency of about once every three days.

6. The method of claim 1, wherein the compound is administered for a period of about 1 to about 60 weeks.

7. The method of claim 5, wherein the compound is administered about once every three days for about 24 days.

8. The method of claim 1, wherein the compound is administered over an infusion period of about 1 to about 6 hours.

9. The method of claim 1, wherein the cancer is relapsed or refractory or the patient is unsuitable for standard chemotherapy.

10. The method of claim 1, wherein the patient is also treated with erlotinib and/or cetuximab.

11. The method of claim 1, wherein the cancer treated is non-small cell lung cancer.

12. The method of claim 1, wherein the cancer treated is squamous cell cancer of the head and neck or skin.

13. The method of claim 1, wherein the compound is administered in a dosage unit comprising a pharmaceutically acceptable formulation of the compound.

14. The method of claim 13, wherein the pharmaceutically acceptable formulation comprises the compound or a pharmaceutically acceptable salt or solvate thereof and 2-hydroxylpropyl-3-cyclodextrin.

15. The method of claim 14, wherein the dosage unit comprises about 75 to about 150 mg of the compound.

16. The method of claim 1, wherein the compound is administered in a dose of about 150 mg/m$^2$.

17. The method of claim 1, wherein the cancer is heterozygous for the EGFR protein.

18. The method of claim 17, wherein the cancer is characterized by a genotype comprising one mutant EGFR allele and one wild-type EGFR allele.

19. The method of claim 1, wherein the cancer is homozygous for wild-type activity of the EGFR protein.

20. The method of claim 1, wherein the activity of the wild-type EGFR protein is overexpressed or upregulated.

21. The method of claim 1, wherein the expressed EGFR protein has a wild-type active site.

22. The method of claim 21, wherein the cancer is characterized by at least one copy of Exon 19 of the EGFR gene.

23. The method of claim 1, wherein the compound is administered in a dose of about 32 mg/m$^2$.

24. The method of claim 1, wherein the compound is administered in a dose of about 20 mg/m$^2$.

* * * * *

UNITED STATES PATENT AND TRADEMARK OFFICE
CERTIFICATE OF CORRECTION

PATENT NO. : 10,507,210 B2
APPLICATION NO. : 15/531677
DATED : December 17, 2019
INVENTOR(S) : Adam Vorn Patterson et al.

Page 1 of 1

It is certified that error appears in the above-identified patent and that said Letters Patent is hereby corrected as shown below:

On the Title Page

Page 2, item [56]:

"Felip et al., "A Phase Ii Pharmacodynamic Study of Erlotinib in"
Should read:
-- Felip et al., "A Phase II Pharmacodynamic Study of Erlotinib in --

"Kan et al., "Antenatal diagnosis of sickle-cell anxmia by DNA"
Should read:
-- Kan et al., "Antenatal diagnosis of sickle-cell anaemia by DNA --

"Sharma et al., ""Oncogenic Shock": Explaining Oncogene Addiction through Differential Signal Attenuation" , Clin Cancer Res., 12(14 Pt 2):43925-43955 (2006)."
Should read:
-- Sharma et al., ""Oncogenic Shock": Explaining Oncogene Addiction through Differential Signal Attenuation" , Clin Cancer Res., 12(14 Pt 2):4392s-4395s (2006). --

In the Claims

Column 42, Claim number 14, Line number 56:
"2-hydroxylpropyl-3-cyclodextrin"
Should read:
-- 2-hydroxylpropyl-β-cyclodextrin --

Signed and Sealed this
Twenty-fifth Day of February, 2020

Andrei Iancu
*Director of the United States Patent and Trademark Office*